United States Patent
Neyts et al.

(10) Patent No.: US 12,286,423 B2
(45) Date of Patent: Apr. 29, 2025

(54) ANTIVIRAL 1,3-DI-OXO-INDENE COMPOUNDS

(71) Applicants: Novartis AG, Basel (CH); Katholieke Universiteit Leuven, Leuven (BE); Korea Research Institute of Chemical Technology, Daejeon (KR)

(72) Inventors: Johan Neyts, Kessel-Lo (BE); Daniel Poon, Piedmont, CA (US); Keith Bruce Pfister, Emeryville, CA (US); Young-Sik Jung, Daejeon (KR); Soo Bong Han, Daejeon (KR); Yashwardhan R. Malpani, Daejeon (KR); Prashant Chakrasali, Daejeon (KR); Bishyajit Kumar Biswas, Daejeon (KR); Chong-Kyo Lee, Daejeon (KR); Chonsaeng Kim, Daejeon (KR); Jin Soo Shin, Daejeon (KR); Hae Soo Kim, Daejeon (KR)

(73) Assignees: Novartis AG, Basel (CH); Katholieke Universiteit Leuven, Keuven (BE); Korea Research Institute of Chemical Technology, Daejeon (KR)

( * ) Notice: Subject to any disclaimer, the term of this patent is extended or adjusted under 35 U.S.C. 154(b) by 166 days.

(21) Appl. No.: 17/235,120

(22) Filed: Apr. 20, 2021

(65) Prior Publication Data
US 2021/0323947 A1    Oct. 21, 2021

Related U.S. Application Data

(60) Provisional application No. 63/012,780, filed on Apr. 20, 2020.

(51) Int. Cl.
| | |
|---|---|
| *C07D 405/12* | (2006.01) |
| *A61K 45/06* | (2006.01) |
| *A61P 31/14* | (2006.01) |
| *C07D 307/93* | (2006.01) |
| *C07D 405/14* | (2006.01) |

(52) U.S. Cl.
CPC ............ *C07D 405/12* (2013.01); *A61K 45/06* (2013.01); *A61P 31/14* (2018.01); *C07D 307/93* (2013.01); *C07D 405/14* (2013.01)

(58) Field of Classification Search
CPC ... C07D 405/12; C07D 405/14; C07D 307/93
See application file for complete search history.

(56) References Cited

U.S. PATENT DOCUMENTS

| | | | |
|---|---|---|---|
| 3,892,807 A | 7/1975 | Sahm | |
| 3,984,552 A | 10/1976 | Cragoe et al. | |
| 4,569,945 A | 2/1986 | Campbell et al. | |
| 9,346,749 B2 | 5/2016 | Jung et al. | |
| 9,464,067 B2 | 10/2016 | Jung et al. | |
| 9,790,197 B2 | 10/2017 | Jung et al. | |
| 9,833,423 B2 | 12/2017 | Jung et al. | |
| 9,890,133 B2 | 2/2018 | Jung et al. | |
| 9,951,058 B2 | 4/2018 | Jung et al. | |
| 2002/0091261 A1 | 7/2002 | Bold et al. | |
| 2010/0133117 A1 | 6/2010 | Gao | |
| 2010/0261706 A1 | 10/2010 | Jagtap et al. | |
| 2014/0114068 A1 | 4/2014 | Jung et al. | |
| 2021/0322362 A1 | 10/2021 | Neyts et al. | |
| 2021/0323947 A1 | 10/2021 | Neyts et al. | |

FOREIGN PATENT DOCUMENTS

| | | | | |
|---|---|---|---|---|
| CN | 103764140 B | 5/2017 | | |
| EP | 0481708 A1 | 4/1992 | | |
| EP | 409410 B1 | 3/1996 | | |
| EP | 1081138 B1 | 9/2004 | | |
| EP | 2722042 A2 * | 4/2014 | ........... | A61K 31/343 |
| EP | 2324820 B1 | 3/2016 | | |
| EP | 2722042 B1 | 5/2019 | | |
| FR | 2392951 A2 | 12/1978 | | |
| GB | 1425295 A | 2/1976 | | |
| GB | 1533388 A | 11/1978 | | |

(Continued)

OTHER PUBLICATIONS

Blood et al., "The preparation of 4 : 4'-Bistetrahydropyranyl and of Ethane-1 : 1 : 2 : 2-tetra-acetic Acid," Journal of the Chemical Society, 1952, pp. 2268-2272.
Cheng et al., "N-Heterocyclic Carbene Catalyzed Reaction of Phthalaldehydes: Controllable Stereoselective Synthesis of Polyhydroxylated Spiro- and Fused Indenones Dictated by the Structure of NHC Catalysts," The Journal of Organic Chemistry, 2011, vol. 76, No. 6, pp. 1844-1851.
Aleman, J. et al., "Organocatalytic Highly Enantioselective ἀ -Arylation of β-Ketoesters", Angewandte Chemie International Edition, 2007, vol. 46, pp. 5515-5519.
Almog, Joseph et al., "The reaction between phloroglucinol and vic polycarbonyl compounds: extension and mechanistic elucidation of Kim's synthesis for bipolarofacial bowl-shaped compounds", Tetrahedron 65, (2009), pp. 7954-7962.

(Continued)

*Primary Examiner* — Kortney L. Klinkel
*Assistant Examiner* — Mikhail O'Donnel Robinson
(74) *Attorney, Agent, or Firm* — Sheppard Mullin Richter & Hampton LLP

(57) ABSTRACT

The invention provides compounds of Formula (I):

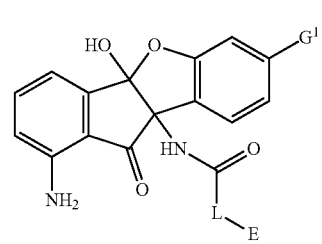

as described herein, along with pharmaceutically acceptable salts, pharmaceutical compositions containing such compounds, and methods to use these compounds, salts and compositions for treating viral infections.

4 Claims, No Drawings

(56) References Cited

FOREIGN PATENT DOCUMENTS

| JP | 60109541 A | 6/1985 |
|---|---|---|
| JP | 2001089455 A | 4/2001 |
| JP | 2014523417 | 9/2014 |
| JP | 2016504321 | 2/2016 |
| RU | 2207132 C2 | 6/2003 |
| SU | 725559 A1 | 3/1980 |
| UA | 79834 C2 | 7/2007 |
| WO | 2003082265 A2 | 10/2003 |
| WO | 2004041201 A2 | 5/2004 |
| WO | 2004041812 A1 | 5/2004 |
| WO | 2004087153 A2 | 10/2004 |
| WO | 2010003023 A2 | 1/2010 |

OTHER PUBLICATIONS

Arens, A., et al., "2-Amino derivatives of 4,5-and 5,6-dimethoxy-2-phenylindan-1,3-diones," Latvijas PSR Zinatnu Akademijas Vestis, Kimijas, 1966, vol. 3, pp. 342-346.
Arens, A., et al., "Amino derivatives of 2-piperonyl-1,3-idandione," Zhurnal Obshchei Khimii, 1964, vol. 34, No. 2, pp. 442-445.
Arens, A., et al., "Isomerization of 2-amino-2-substituted 1,3-indandiones," Latvijas PSR Zinatnu Akademijas Vestis, Kimijas Serija, 1980, vol. 6, pp. 677-691.
Arens, Augusts, et al., "2-Amino-2-halophenyl-1,3-indandiones," Latvijas PSR Zinatnu Akademijas Vestis, Kimijas Serija, 1969, vol. 4, pp. 446-451.
Arens, Augusts, et al., "Reduction of aminodicarboxylic compounds. III. 2-Alkylamino-2-phenyl-3-indanon-1-ol and 2-alkylamino-2-phenyl-1,3-indandiol," Journal of Organic Chemistry of the USSR, 1969, vol. 5, No. 9, pp. 2094-2097.
Benders, J. et al., "Esr spectra of semidiones derived from indandione -1,3," Journal of Molecular Structure, vol. 19, (Dec. 1, 1973), pp. 431-440.
Bite, Dz., et al., "Substituted thiourea β-dicarbonyl compounds. IX. Spectroscopic study of 2-substituted N-[1, 3-Indandion-2-yl] thiourea and 2-(2-iminothiazolidin-3-yl]-2-substituted 1, 3-indandiounes," Latvijas PSR Zinatnu Akademijas Vestis Kimijas Serija, 1969, vol. 1, pp. 109-112.
Black, D.S.C., et al., "Reactions of Ninhydrin with Activated Anilines: Formation of Indole Derivatives", Tetrahedron, (1994), vol. 50, No. 37, pp. 10983-10994.
Briede, V., et al., "4,5-Dimethoxy-2-β-naphthyl-1,3-indandione," Latvijas PSR Zinatnu Akademijas Vestis, Kimijas Serija, 1967, vol. 3, pp. 329-333.
Bullington, J.L. et al., "Synthesis of Spiro[2H-indole]-3,3'-diones and Spiro[benzofuran-2,1'-isobenzofuran]-3,3'-diones via Transannular Reactions of Eight Membered Ring Intermediates", Journal of Heterocyclic Chemistry, vol. 35 (Mar.-Apr. 1998), pp. 397-403.
Bullington, James L., et al., "Synthesis of tetrahydroineno[1,2-b] indol-10-ones and Their rearrangement to [2] Benzopyrano[4,3-b]indol-5-ones", Journal of Organic Chemistry, vol. 58, No. 18, (1993), pp. 4833-4836.
Butera, John A., "Synthesis and Potassium Channel Opening Activity of Substituted 10H-Benzo[4,5]furo[3,2-b] Indole- and 5, 10-Dihydroindeno[1,2-b] indole-1-carboxylic Acids", Bioorganic & Medicinal Chemistry Letters, 2001, vol. 11, pp. 2093-2094.
Courant, J. et al., "1,3-Indandiones VIII. 2-Hydroxy-2-indolyl-1, 3-indandiones, 2-(indol-3-ylmethylene indandione and derivatives: search for anti-inflammatory activity," European Journal of Medicinal Chemistry, Editions Scientifique Elsevier, Paris, FR., vol. 24, No. 2, (Mar. 1, 1989), pp. 145-154.
Das, S. et al., "A Facile Synthesis of Benzofuroisocoumarins from C-2 Arylated 1,3-Indanediones", Synlett, 2006, vol. 2, pp. 207-210.
Das, Suven et al., "A simple synthesis of 4-substituted 2,3-benzoxazinones from C-2 arylated 1,3-indanediones", Tetrahedron Letters, vol. 52, No. 25, (Apr. 27, 2011) pp. 3243-3246.

Diana, Guy D. "Inhibitors of Picornavirus Replication", Current Medicinal Chemistry-Anti-Infective Agents, vol. 2. No. 1. (Mar. 2003), pp. 1-12.
Eckstein, Zygmunt, et al., "Infrared absorption spectra of 2-nitroindandione derivatives," Bulletin de l'Academie Polonaise des Sciences, Serie des Sciences Chimiques, 1960, vol. 8, No. 10, pp. 579-586.
Extended European Search Report for EP 12799827.6, mailed Nov. 19, 2014.
Extended European Search Report for EP 12800577.4, mailed Mar. 24, 2015.
Grinsteins, V., et al., "Synthesis and study of thioureas. Infrared spectra of 2-aryl-2-thiocarbamido-1,3-indandiones," Latvijas PSR Zinatnu Akademijas Vestis, Kimijas Serija, 1972, vol. 4, pp. 441-444.
Groarke, James M. et al. "Attenuated Virulence of Pleconaril-Resistant Coxsackievirus B3 Variants", The Journal of Infectious Diseases, (Jun. 1999), vol. 179(6); pp. 1538-1541.
Gudriniece, E., et al., "2-Azido-2-substituted indan-1,3-dione," Doklady Akademii Nauk SSSR, 1966, vol. 171, No. 4, pp. 869-871.
Hark, Richard R. et al. "Synthetic studies of novel ninhydrin analogs", Can. J. Chem., vol. 79, (2001); pp. 1632-1654.
Hashimoto, Suzumi et al., "Dynamic behavior of cyclic hemiacetals of 2-Hydroxy-2-(2-hydroxyphenyl)-1,3-indandione derivatives", Chemistry Letters, vol. 37, No. 7, (2008), pp. 696-697.
Heffner, Robert J., et al., "A Synthesis of Two Novel Benzo[f]Ninhydrin Analogs: 6-Methoxybenzo[f]Ninhydrin and Thieno[f]Ninhydrin", Synthietic Communications, 21(8&9), (1991), pp. 1055-1069.
Heffner, Robert J., et al., "Synthetic Routes To Ninhydrines, Preparation of Ninhydrin, 5-Methoxyninhydrin, and 5-(Methylthio)Ninhydrin," Synthetic Communications, 21(21), (1991), pp. 2231-2256.
Heinz, Beverly A. et al., "The Antiviral Compound Enviroxime Targets the 3A Coding Region of Rhinovirus and Poliovirus", Journal of Virology, vol. 6, No. 7, (Jul. 1995), pp. 4189-4197.
International Search Report and Written Opinion of the International Searching Authority for PCT/KR2012/004804, mailed Dec. 28, 2012.
International Search Report and Written Opinion of the International Searching Authority for PCT/KR2012/004806, mailed Dec. 6, 2012.
International Search Report for Application No. PCT/KR2013/011668, dated Mar. 31, 2014.
International Search Report, issued in PCT/EP2021/060263, dated Jun. 4, 2021.
International Search Report, issued in PCT/EP2021/060271, dated Jul. 23, 2021.
Jasinskas, L., et al., "Synthesis of secondary amines of 4-methyl-2-phenylindandione," Lietuvos TSR Aukstuju Mokyklu Mokslo Darbai, Chem. Ir Chem. Technol., 1965, vol. 7, pp. 77-80.
Jeyachandran, Malaichamy et al., "Synthesis, Antimicrobial, and Anticoagulant Activities of 2-(Arylsulfonyl) indane-1,3-diones", Organic Chemistry International, vol. 2, No. 4, (Jan. 1, 2011), pp. 175-179.
Kapoor, Mona et al., "Stereoselective Synthesis of Z-3-alkoxy-2-[(4'-methoxyphenyl)methylidene]-1(3H)-isobenzofuranones", Tetrahedron Letters, vol. 59, No. 27, pp. 5027-5031, (Jun. 30, 2003).
King, Med. Chem: Principle and Practice (1994), pp. 206-208.
Kundu, Sandip Kumar et al., "6-(alpha-Hydroxy-alpha-aryl/naphthyl)methyl-3,4-dihydro-2,5-benzodiazocin-1(2H)-ones and diphenylmethanes from C-2 arylated 1,3-indanediones", Journal of Chemical Research, vol. 11, (2004), pp. 781-783.
Kundu, Sandip Kumar et al., "Theoretical studies of the acid-catalyzed condensation of ninhydrin with aromatic compounds", Indian Journal of Chemistry, Section B: Organic Chemistry, vol. 43B, No. 10, (2004), pp. 2212-2216.
Kuprava et al., Soobshcheniya Akademii Nauk Gruzinskoi SSR (1964), Vo. 36(3), pp. 573-577.
Ledford, Rebecca M. et al., "VP1 Sequencing of All Human Rhinovirus Serotypes: Insights into Genus Phylogeny and Susceptibility to Antiviral Capsid-Binding Compounds", Journal of Virology, vol. 78, No. 7, (Apr. 2004), pp. 3663-3674.

(56) References Cited

OTHER PUBLICATIONS

Letcher, Roy M., "First Synthesis of Spiro[benzofuran-2,1'-isobenzofuran]-3,3'-dione and its X-Ray Crystal Structure", J.Chem. Soc.Perkin Trans. 1, 1992, pp. 1769-1771.
Leuchs, H. et al. "New reactions of indolenines and inolinols", Justus Liebigs Annalen der Chemie, (1928), vol. 461, pp. 27-46, structures therefrom via Caplus.
Leuchs, Hermann, Wulkow, Gerhard, and Gerland, Heinz, "Indolenines V. Addition of Acid Halides to Indolenines", Caplus, (1932), vol. 151, pp. 1586-1592.
Liu, Yaya et al., "Investigating the Origin of the Slow-Binding Inhibition of HCV NS3 Serine Protease by a Novel Substrate Based inhibitor", BioChemistry, vol. 42, No. 29, (Jul. 1, 2003), pp. 8862-8869.
Lombardino, J.G. et al., "Anti inflammatory 2-Aryl-1,3-indandiones", Journal of Medicinal Chemistry, (1968), vol. 11, No. 6, pp. 342-347.
McKinlay, Mark A. et al., "Treatment of The Picornavirus Common Cold By Inhibitors of Viral Uncoating and Attachment", Annual Review of Microbiology, (Oct. 1992), vol. 46. pp. 635-654.
Mehdi, Sayed Hansan, "Synthesis, characterization, antimicrobial and enzymatic activity of 4b,9b-dihydroxy-7,8-dihydro-4bH-indeno[1,2-b]benzofuran-9, 10(6H,9bH)-dione", Journal of Molecular Structure, 2011, vol. 1006, pp. 318-323.
Miller, F. Dewolfe et al., "Controlled Trial of Enviroxime Against Natural Rhinovirus Infections in a Community", Antimicrobial Agents and Chemotherapy, (Jan. 1985), vol. 27. No. 1, pp. 102-106.
Mosher, William A. et al., "Reactions of some methylene ketones with dimethyl phthalate. New route to 2-substituted 1,3-indandiones", The Journal of Organic Chemistry, vol. 36, No. 11, (Jun. 1, 1971), pp. 1561-1563.
Mudiganti, N.V.S., et al., "Ytterbium triflate-catalyzed conjugate addition of B-ketoesters to activated 1,4-naphthoquinones", Tetrahedron Letters, vol. 65, (2009), pp. 1716-1723.
Na, J. E. et al., "Serendipitous one-pot synthesis of brand-new, bowl-shaped molecular architecture from bhloroglucinol and ninhydrin", Tetrahedron Letters, vol. 46, No. 26, (Jun. 27, 2005), pp. 4505-4508.
Na, Jeong Eun et al., "Selective methylation of the Ninhydrin-phenol adducts with I2 in MeOH", Bulletin of the Korean Chemical Society, vol. 25, No. 4, (2004), pp. 569-572.
Na, Jeong Eun et al., "Synthesis of benzo[b]indeno [2,1-d]furanone skeleton from ninhydrin and cyclohexane-1, 3-dione derivatives", Bulletin of the Korean Chemical Society, vol. 24, No. 12, (2003), pp. 1725-1726.
Neiland, L.E. et al., "2-Aryl-4-azaindain-1, 3-diones", Chemistry of Heterocyclic Compounds, vol. 3, No. 1, (Jan. 1, 1969), pp. 81-83.
Doyama, Yousuke, "Molecular design of novel non-planar heteropolycyclic fluorophores with bulky substituents: convenient synthesis and solid-state fluorescence characterization", Organic & Biomolecular Chemistry, 2006, vol. 4, pp. 3406-3409.
Ozola, A. Ua et al., "A new method of synthesizing 4-azaidan-1, 3-dione derivatives", Chemistry of Heterocyclic Compounds, vol. 9, No. 8, (Aug. 1, 1973), pp. 1062.
Ozola, A. Ya et al., "4-Azaindane-1, 3-dione derivatives. III. Reactivities and prototropic transformations of new 4-azaindane-1,3-diones", Chemistry of Heterocyclic Compounds, vol. 12, No. 2, (Feb. 1, 1976), pp. 220-226.
Patick, A.K., et al., "In Vitro Antiviral Activity of AG7088, a Potent Inhibtor of Human Rhinovirus 3C Protease", Antimicrobial Agents and Chemotherapy, Oct. 1999, vol. 43, No. 10, pp. 2444-2450.
Pevear, Daniel C. et al., "Activity of Pleconaril against Enteroviruses", Antimicrobial Agents and Chemotherapy, (Sep. 1999), vol. 43, No. 9, pp. 2109-2115.
Poupelin, J.P. et al., "Derives de 1 'hydroy-2 Indanedione-1, 3.II. Produits de condensation de la ninhydrine avec les polyphenols et leurs derives 0-methyles//2-hydroxy-1,3-indanedione derivatives. II. (Condensation of ninhydrin with polyphenols and their 3-methylated derivatives)", European Journal of Medicinal Chemistry, Editions Scientifique, vol. 15, No. 3, (Jan. 1, 1980), pp. 253-262.

Poupelin, Jean Pierre et al., "Synthese Et Proprietes Pharmalogiques De Derives De L'Hydroxy-2 Indanedione-1,3; I. Produits De Condensation De La Ninhydrine Avec Les Phenols C-Alkyles", Eur. J. Med. Chem.—Chimica Therapeutique, March-April, vol. 14, No. 2, (Jan. 1, 1979), pp. 171-179 (including English abstract).
Prabhakar, et al., "Identification and evaluation of antioxidant, analgesic/anti-inflammatory activity of the most active ninhydrin-phenol adducts synthesized", Bioorganic & Medicinal Chemistry, vol. 14, No. 21, (Nov. 1, 2006), pp. 7113-7120.
Registry 908828-65-9 (Sep. 27, 2006); 907954-66-9 (Sep. 20, 2006); 408315-53-7 (Apr. 26, 2002).
Rotbergs, J., et al., "Condensation of dicarboxylic acid anhydrides with compounds containing active methylene groups. XXVII. 2-Aryl-1,3-indandiones containing methyl groups," Latvijas PSR Zinatnu Akademijas Vestis, Kimijas Serija, 1974, vol. 1, pp. 75-78.
Roth, H.J., et al., "Reaktionen mit Dimethoxyanilinen und reaktiven Aromaten", Archiv der Pharmazie, (1976), vol. 32, pp. 81-91.
Schmitt, Gerard et al., "A New and Mild Synthesis of Substituted Salicylic Acids", Synthesis, vol. 1984, No. 09 (Jan. 1, 1984), pp. 758-760.
Solomek, T., et al., "Photoenolization-Induced Oxirane Ring Opening in 2,5-Dimethylbenzoyl Oxiranes To Form Pharmaceutically Promising Indanone Derivatives", J. Org. Chem. Vo. 75, No. 21, 2010, pp. 7300-7309.
Song Hyun Nam, et al., "The Reaction of Ninhydrin with Polymethylbenzenes in the Presence of Acid Catalyst: Formation of 2-aryl-1,3-indanedione and Indenoindanone Derivative", Bull. Korean Chem. Soc. vol. 20, No. 10, pp. 1229-1231, Oct. 20, 1999.
Song, H.N. et al., "Formation of Benzo[b]Indeno [2,1-d]Furanone Ring System During Alkylation of 2-(2-Hydroxyaryl)-2-Hydroxy-1,3-Indanedione Derivatives", Synthetic Communications, (1999), vol. 29, No. 16, pp. 2759-2767.
Song, Hyun Nam et al., "A Study on the Friedel-Crafts Type Reaction of Ninhydrin with Arenes", Synthetic Communications, 28(10), pp. 1865-1870, (1998).
Song, Hyun Nam et al., "Difference in Reactivity during Alkylation of 2-(2-Hydroxyaryl)-1,3-indanedione and N-(2-Hydroxyphenyl)phthalimide", Bull. Korean Chem. Soc., (1999); vol. 20, No. 6, pp. 631-632.
Song, Hyun Nam et al., "Friedel-Crafts Type Reactions of Some Activated Cyclic Ketones with Phenol Derivatives", Synthetic Communications, 29(19), pp. 3303-3311, (1999).
Song, Hyun Nam et al., "The Reaction of Ninhydrin with Trimethylbenzenes Under Friedel-Crafts Reaction Conditions", Synthetic Communications, 30(6), pp. 1057-1066, (2000).
Stadlbauer, W. et al. DN, "Thermal Cyclization of 3-Azido-2-phenyl-indan-1-one to 5H-Indeno[1,2-b]indol-10-one", Journal of Heterocyclic Chemistry, (2002) 39(1), pp. 131-135 (Abstract).
Sun, Fang-Gang, et al., "N-Heterocyclic carbine-catalyzed [4 + 1] annulation of phthalaldehyde and imines," Organic & Biomolecular Chemistry, vol. 9, No. 10, May 21, 2011, pp. 3573-3635.
Suzuki, Masaya, et al., "Photorearrangements in spiro-conjoined cyclohexa-2,5-dien-1-one", Tetrahedron vol. 67, pp. 5500-5506, Available online May 14, 2011.
The Merck Index, 2001, Thirteenth Edition, p. 674, 1380, 2432, 7314.
Thibaut et al., "A novel class of highly potent small molecule inhibitors of entero/rhinovirus replication with an excellent safety and pharmacokinetic profile are highly effective against enterovirus infections in mice.", Poster presented at 26th International Conference on Antiviral Research, San Francisco, CA, (May 11-15, 2013).
Thibaut et al., "A novel class of highly potent small molecule inhibitors of entero/rhinovirus replication that target the non-structural protein 2C", Poster presented at 26th International Conference on Antiviral Research, San Francisco, CA (May 11-15, 2013).
Timtcheva et al., "Luminescence Properties of Some 4- or 5-Aminosubstituted Indan-1,3-diones," Z. Naturforsch, (1987), vol. 42a, pp. 289-292.
Vasilev, G., et al., "Synthesis, chemical structure, and biological activity of certain N-substituted 2-ureido-or hioureido-2-phenyl-1,3-indandiones," Doklady Bolgarskoi Akademii Nauk, 1986, vol. 39, No. 2, pp. 93-96.

(56) References Cited

OTHER PUBLICATIONS

Vegnere, V., et al., "Adsorptive capacity of 2-amino-substituted indans on a mercury electrode," Latvijas PSR Zinatnu Akademijas Vestis, Kimijas Serija, 1973, vol. 4, pp. 446-451.

Yin-Murphy, Marguerite and Almond, Jeffrey W., "Chapter 53Picornaviruses", Medical Microbiology, 4th Ed., Galveston (TX): Univ. of Texas Medical Branch at Galveston, (1996), pp. 1-18.

Zalukaev, L.P., et al., "Synthesis of new α-nitro-α-arylmethylenephthalides," Izvestiya Vysshikh Uchebnykh Zavedenii, Khimiya I Khimicheskaya Tekhnologiya, 1970, vol. 13, No. 10, pp. 1453-1456.

Zalukaev, L.P., et al., "Synthesis of α-nitromethylpyridine and its derivatives," Khimiya Geterotsiklicheskikh Soedinenii, 1967, vol. 3, pp. 515-517.

Zalukaievs, L., et al., "Preparation of 2-nitromethylquinoline and its derivatives," Zhurnal Obshchei Khimii, 1956, vol. 26, pp. 2639-2642.

Zalukajevs, L., et al., "Nitration of phthalones," Zhurnal Obshchei Khimii, 1957, vol. 27, pp. 3278-3282.

\* cited by examiner

ANTIVIRAL 1,3-DI-OXO-INDENE COMPOUNDS

CROSS REFERENCE TO RELATED APPLICATIONS

This application claims priority to U.S. Provisional Application No. 63/012,780, filed Apr. 20, 2020, the disclosure of which is hereby incorporated by reference in its entirety for all purposes.

FIELD OF THE INVENTION

The present invention relates to novel 1,3-dioxoindene compounds that are inhibitors of picornaviruses including coxsackie-, entero-, echo-, polio-, and rhinoviruses, and are thus useful to treat viral infections, including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media. The invention provides novel tetracyclic pyridone compounds as disclosed herein, pharmaceutical compositions containing such compounds, and methods of using these compounds and compositions in the treatment and prevention of viral diseases.

BACKGROUND

Picornaviruses are non-enveloped, positive single-stranded RNA viruses with an RNA genome 7.2-8.5 Kb long. These viruses are very small and globular in shape with a size of about 22~30 nm, and were first identified a long time ago. Among the viruses belonging to the family Picornaviridae are enteroviruses including rhinovirus, poliovirus, coxsackievirus A, coxsackievirus B, and echovirus, and hepatitis A virus.

The diseases that picornaviruses cause are varied, ranging from respiratory diseases to digestive diseases, to circulatory diseases and to dermal diseases, examples of which include poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, and foot-and-mouth disease. However, there are no therapeutics for curing these diseases. Most of the drugs under development are uncoating inhibitors. Viruses belonging to the family Picornaviridae cause various diseases including the aforementioned respiratory diseases, which evoke hygienic, social and economic issues. Picornaviruses are the main causative agents of waterborne diseases. Being very stable and difficult to disinfect, the RNA viruses incessantly cause related diseases.

Human rhinoviruses (hRV) have been recently associated with the majority of asthma exacerbations, and are known to exist even in bronchial tissues of many stable asthma patients. Comparison of respective bronchial mucosa biopsy specimens taken from asthma and non-asthma patients showed significantly higher frequencies of detection of human rhinoviruses in the lower respiratory tract of asthma patients, compared to non-asthma patients. It has also been reported that there is correlation between the presence of human rhinovirus and the clinical severity of asthma. In addition, rhinoviruses cause chronic obstructive pulmonary disease, pneumonia, sinusitis, and otitis media as well as asthma.

Rhinoviruses are the main causative of the common cold while enterovirus-induced diseases include meningitis, respiratory tract infection, etc. Extensive effort to provide vaccination against poliovirus has significantly reduced the onset of poliomyelitis worldwide, but there are still reports of cases of the disease in Niger, Nigeria, Egypt, India, Pakistan, and Afghanistan. Hepatitis A is now possible to control to some degree thanks to vaccines for hepatitis A viruses. However, no vaccines for coxsackieviruses, echoviruses, or rhinoviruses have been developed, thus far.

Particularly, coxsackievirus B is a main cause of myocarditis, which may develop, in serious cases, into idiopathic dilated cardiomyopathy, which requires heart transplantation Enviroxime derivatives are considered the most promising candidate with a broad anti-enterovirus- and anti-rhinovirus activity. Enviroxime interferes with the synthesis of plus-strand RNA by binding to the virus protein 3A that is required for the formation of RNA intermediates in the virus reproduction (Heinz B A and Vance L M: J Virol, 1995, 69(7), 4189-97). In clinical studies, however, the compound was observed to have insignificant or few therapeutic effects, with the concomitant detection of bad pharmacokinetics and unwanted side effects (Miller F D et al.: Antimicrob Agents Chemother, 1985, 27(1), 102-6).

The protease inhibitor AG 7088 has been developed on the basis of the knowledge about the fine structure and function of the viral protease 2C. In the cell culture in the nanomolar concentration range. AG 7088 has an effect against 48 rhinovirus types and coxsackievirus A21, B3, enterovirus 70 and echovirus 11 (Pattick A K et al.: Antimicrobila Agents Chemother, 1999, 43(10), 2444-50).

Thanks to the clarification of the molecular structure of the viral capsids, the preconditions for a purposeful design of capsid blockers, the "WIN substances", have been obtained (Diana G D: Curr Med Chem 2003, 2, 1-12). They inhibit the adsorption and/or the uncoating of rhinoviruses and enteroviruses. Some of the WIN substances have a highly specific effect only against individual genera or virus types of the picornaviruses. Other derivatives inhibit the replication both of rhinoviruses and enteroviruses. Arildone, disoxaril and pirodavir belong, for example, to the WIN substances. These compounds showed very good antiviral effects in the cell culture. However, a poor solubility (arildone), low bioavailability (arildone and disoxaril), a rapid metabolization and excretion (disoxaril and WIN 54954) as well as side effects, such as skin rash (WIN 54954), made a clinical application impossible.

Pleconaril, a kind of WIN substance, has a very good oral bioavailability and after its binding to the hydrophobe pocket in the viruscapsid, it inhibits the penetration of rhino-, echo- and coxsackieviruses (Pevear D C et al.: Antimicrob Agents Chemother 1999, 43(9), 2109-15; McKinlay M A et al.: Annu Rev Microbiol 1992, 46, 635-54). Therefore, pleconaril is potentially effective against a broad spectrum of virus diseases, ranging from the common cold to the viral meningitis or myocarditis. Resistances were observed for rhinoviruses, enterovirus 71 and coxsackievirus B3 (Ledford R M et al.: J Virol 2004, 78(7), 3663-74; Groarke J M et al.: J Infect Dis 1999, 179(6), 1538-41). However, the proven therapeutic effect was not sufficient for the registration of pleconaril (Picovir, Viropharma, USA) as an agent for the treatment of rhinovirus infections in the USA. In March 2002, a corresponding application was refused by the Food and Drug Administration (FDA) because therapy success was too low and side effects were observed.

BTA-798 was found to have higher antiviral activity than pleconaril, as evaluated in vitro and in vivo with rhinoviruses, and is now being under a clinical test (Ryan, J. et al. Antiviral Res [18th Intl Conf Antiviral Res (April 11-14. Barcelona) 2005] 2005, 65(3): Abst LB-11).

However, no antiviral drugs that have gained approval for use in the treatment of entero- or rhinoviruses have been developed, so far. There remains a need for new treatments and therapies against entero- or rhinoviruses.

Leading to the present invention, intensive and thorough research into effective virustatics against picornaviruses including coxsackie-, entero-, echo-, polio-, and rhinoviruses, culminated in the finding that novel 1,3-Dioxoindene derivatives exhibit highly inhibitory activity against picornaviruses including coxsackie-, entero-, echo-, polio-, and rhinoviruses.

SUMMARY

The present invention provides novel compounds with potent antiviral activity in vitro. The invention also provides pharmaceutical compositions containing the novel compounds as well as methods to use the compounds and compositions to inhibit virus replication or reactivation, and to treat disease conditions associated with or caused by viruses. Further objects of this invention are described in the following description and the examples.

In one aspect, the invention provides compounds of Formula (I): or a pharmaceutically acceptable salt thereof:

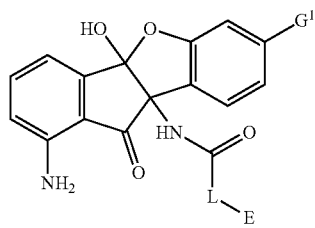

[I]

wherein, $G^1$ is selected from linear or branched $C_1$-$C_4$ alkyl $C_3$-$C_4$ cycloalkyl, or linear or branched $C_1$-$C_4$ alkoxy; wherein the $C_1$-$C_4$ alkyl, $C_3$-$C_4$ cycloalkyl, and $C_1$-$C_4$ alkoxy may be substituted with one, two, or three substituents independently selected from cyclopropyl and linear or branched $C_1$-$C_3$ alkyl;

L is a bond or $CH_2$;

E is
a) —CH(CHOHCH$_3$)(NMe$_2$); or
b) a monocyclic 4-6 membered heterocyclyl containing one or two nitrogen atoms or a 5-6 membered heteroaryl containing one nitrogen atom, wherein the 4-6 membered heterocyclyl and the 5-6 membered heteroaryl is optionally substituted with one to three substituents independently selected from the group consisting of linear or branched $C_1$-$C_3$alkyl, —OH, =O, —SO$_2$R; where in each R is independently selected from linear or branched $C_1$-$C_3$alkyl, monocyclic 5-6 membered heterocyclyl containing one or two nitrogen atoms, and NR$^1$R$^2$; wherein the monocyclic 5-6 membered heterocyclyl is optionally substituted with a $C_1$-$C_3$alkyl or NR$^3$R$^4$;

each R$^1$ and R$^2$ is independently selected from H and $C_1$-$C_3$ alkyl, wherein the $C_1$-$C_3$ alkyl is optionally substituted with NR$^3$R$^4$; and each R$^3$ and R$^4$ is independently selected from H or methyl. In another aspect, the invention provides a pharmaceutical composition comprising a therapeutically effective amount of a compound of the present invention and one or more pharmaceutically acceptable carriers. In another aspect, the invention provides a combination, in particular a pharmaceutical combination, comprising a therapeutically effective amount of compound of the present invention and one or more therapeutically active agents.

DETAILED DESCRIPTION

For purposes of interpreting this specification, the following definitions will apply, and whenever appropriate, terms used in the singular will also include the plural.

Terms used in the specification have the following meanings unless the context clearly indicates otherwise:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject. As used herein, a subject is "in need of" a treatment if such subject would benefit biologically, medically or in quality of life from such treatment.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

"Optionally substituted" means the group referred to can be substituted at one or more positions by any one or any combination of the radicals listed thereafter. The number, placement and selection of substituents is understood to encompass only those substitutions that a skilled chemist would expect to be reasonably stable; thus 'oxo' would not be a substituent on an aryl or heteroaryl ring, for example, and a single carbon atom would not have three hydroxy or amino substituents. Unless otherwise specified, optional substituents are typically up to four groups selected from halo, oxo, CN, amino, hydroxy, —C$_{1-3}$ alkyl, —OR*, —NR*$_2$, —SR*, —SO$_2$R*, —COOR*, and —CONR*$_2$, where each R* is independently H or C$_{1-3}$ alkyl.

"Aryl" as used herein refers to a phenyl or naphthyl group unless otherwise specified. Aryl groups unless otherwise specified may be optionally substituted with up to four groups selected from halo, CN, amino, hydroxy, C$_{1-3}$ alkyl, —OR*, —NR*$_2$, —SR*, —SO$_2$R*, —COOR*, and —CONR*$_2$, where each R* is independently H or C$_{1-3}$ alkyl.

"Halo" or "halogen", as used herein, may be fluorine, chlorine, bromine or iodine.

"C$_{1-6}$alkyl" or "C$_1$-C$_6$ alkyl", as used herein, denotes straight chain or branched alkyl having 1-6 carbon atoms. If a different number of carbon atoms is specified, such as C$_4$ or C$_3$, then the definition is to be amended accordingly, such as "C$_{1-4}$ alkyl" will represent methyl, ethyl, propyl, isopropyl, butyl, isobutyl, sec-butyl and tert-butyl.

"C$_{1-6}$ alkoxy", as used herein, denotes straight chain or branched alkoxy (—O-Alkyl) having 1-6 carbon atoms. If a different number of carbon atoms is specified, such as C$_4$ or C$_3$, then the definition is to be amended accordingly, such as "C$_{1-4}$ alkoxy" will represent methoxy, ethoxy, propoxy, isopropoxy, butoxy, isobutoxy, sec-butoxy and tert-butoxy.

"C$_{1-4}$ Haloalkyl" or "C$_1$-C$_4$ haloalkyl" as used herein, denotes straight chain or branched alkyl having 1-4 carbon atoms wherein at least one hydrogen has been replaced with a halogen. The number of halogen replacements can be from one up to the number of hydrogen atoms on the unsubstituted alkyl group. If a different number of carbon atoms is specified, such as C$_6$ or C$_3$, then the definition is to be amended accordingly. Thus "C$_{1-4}$ haloalkyl" will represent methyl, ethyl, propyl, isopropyl, butyl, isobutyl, sec-butyl and tert-butyl that have at least one hydrogen substituted with halogen, such as where the halogen is fluorine: CF$_3$CF$_2$—, (CF$_3$)$_2$CH—, CH$_3$—CF$_2$—, CF$_3$CF$_2$—, CF$_3$, CF$_2$H—, CF$_3$CF$_2$CH(CF$_3$)— or CF$_3$CF$_2$CF$_2$CF$_2$—.

"C$_{3-8}$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as C$_3$-C$_6$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings; unless otherwise specified, such rings contain 1 to 7, 1 to 5, or 1 to 3 heteroatoms selected from the group consisting of nitrogen, oxygen and sulfur as ring members, and the rings may be saturated, or partially saturated but not aromatic. The heterocyclic group can be attached to another group at a nitrogen or a carbon atom. The term "heterocyclyl" includes single ring groups, fused ring groups and bridged groups. Examples of such heterocyclyl include, but are not limited to pyrrolidine, piperidine, piperazine, pyrrolidinone, morpholine, tetrahydrofuran, tetrahydrothiophene, tetrahydrothiopyran, tetrahydropyran, 1,4-dioxane, 1,4-oxathiane, 8-azabicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane, azetidine, ethylenedioxo, oxetane or thiazole. In certain embodiments, if not otherwise specified, heterocyclic groups have 1-2 heteroatoms selected from N, O and S as ring members, and 4-7 ring atoms, and are optionally substituted with up to four groups selected from halo, oxo, CN, amino, hydroxy, C$_{1-3}$ alkyl, —OR*, —NR*$_2$, —SR*, —SO$_2$R*, —COOR*, and —CONR*$_2$, where each R* is independently H or C$_{1-3}$ alkyl. In particular, heterocyclic groups containing a sulfur atom are optionally substituted with one or two oxo groups on the sulfur.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring or ring system (e.g., 5-7 membered monocyclic group or an 8-10 membered bicyclic group), often a 5-6 membered ring containing up to four heteroatoms selected from N, O and S, though often a heteroaryl ring contains no more than one divalent O or S in the ring. Typical heteroaryl groups include furan, isothiazole, thiadiazole, oxadiazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2,3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl. Heteroaryl groups are and are optionally substituted with up to four groups selected from halo, CN, amino, hydroxy, C$_{1-3}$ alkyl, —OR*, —NR*$_2$, —SR*, —SO$_2$R*, —COOR*, and —CONR*$_2$, where each R* is independently H or C$_{1-3}$ alkyl.

The term "hydroxy" or "hydroxyl" refers to the group —OH.

Various embodiments of the invention are described herein. It will be recognized that features specified in each embodiment may be combined with other specified features to provide further embodiments. The following enumerated embodiments are representative of the invention:

Embodiment 1. A compound of formula (I): or a pharmaceutically acceptable salt thereof:

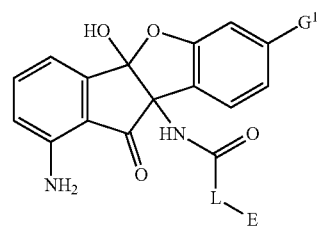

[I]

wherein,

G$^1$ is selected from linear or branched C$_1$-C$_4$ alkyl C$_3$-C$_4$ cycloalkyl, or linear or branched C$_1$-C$_4$ alkoxy; wherein the C$_1$-C$_4$ alkyl, C$_3$-C$_4$ cycloalkyl, and C$_1$-C$_4$ alkoxy may be substituted with one, two, or three substituents independently selected from cyclopropyl and linear or branched C$_1$-C$_3$ alkyl;

L is a bond or C$_1$-C$_4$ straight chain or branched alkylene linker;

E is
a) —CH(CHOHCH$_3$)(NMe$_2$); or
b) a monocyclic 4-6 membered heterocyclyl containing one or two nitrogen atoms or a 5-6 membered heteroaryl containing one nitrogen atom, wherein the 4-6 membered heterocyclyl and the 5-6 membered heteroaryl is optionally substituted with one to three substituents independently selected from the group consisting of linear or branched $C_1$-$C_3$alkyl, —OH, =O, —$SO_2$R; where in each R is independently selected from linear or branched $C_1$-$C_3$alkyl, monocyclic 5-6 membered heterocyclyl containing one or two nitrogen atoms, and $NR^1R^2$; wherein the monocyclic 5-6 membered heterocyclyl is optionally substituted with a $C_1$-$C_3$alkyl or $NR^3R^4$;

each $R^1$ and $R^2$ is independently selected from H and $C_1$-$C_3$ alkyl, wherein the $C_1$-$C_3$ alkyl is optionally substituted with $NR^3R^4$; and each $R^3$ and $R^4$ is independently selected from H or methyl.

Embodiment 2. The compound of embodiment 1, having Formula (II), or a pharmaceutically acceptable salt thereof:

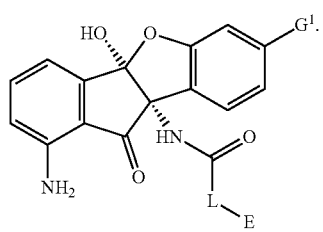

[II]

Embodiment 3. The compound of Embodiment 1, having Formula (III), or a pharmaceutically acceptable salt thereof:

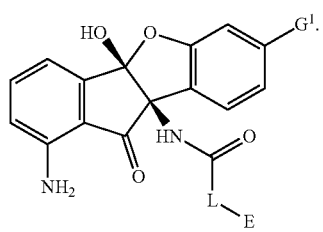

[III]

Embodiment 4. A compound according to any one of the preceding embodiments, or a pharmaceutically acceptable salt thereof, wherein $G^1$ is linear or branched $C_1$-$C_4$ alkyl.

Embodiment 5. A compound according to any one of the preceding embodiments, or a pharmaceutically acceptable salt thereof, wherein $G^1$ is $C_3$-$C_4$ cycloalkyl.

Embodiment 6. A compound according to any one of the preceding embodiments, or a pharmaceutically acceptable salt thereof, wherein $G^1$ is linear or branched $C_1$-$C_4$ alkoxy.

Embodiment 7. A compound according to any one of the preceding embodiments, or a pharmaceutically acceptable salt thereof, wherein the $C_1$-$C_4$ alkyl, $C_3$-$C_4$ cycloalkyl, and $C_1$-$C_4$ alkoxy may be substituted with one, two, or three substituents.

Embodiment 8. A compound according to any one of the preceding embodiments, or a pharmaceutically acceptable salt thereof, wherein the substituents are independently selected from cyclopropyl and linear or branched $C_1$-$C_3$ alkyl.

Embodiment 9. A compound according to any one of the preceding embodiments, or a pharmaceutically acceptable salt thereof, wherein L is a bond. A compound according to any one of the preceding embodiments, or a pharmaceutically acceptable salt thereof, wherein L is a $C_1$-$C_4$ straight chain or branched alkylene linker. A compound according to any one of the preceding embodiments, or a pharmaceutically acceptable salt thereof, wherein L is $CH_2$.

Embodiment 10. A compound according to any one of the preceding embodiments, or a pharmaceutically acceptable salt thereof, wherein E is —C(CHOHCH$_3$)(NMe$_2$).

Embodiment 11. A compound according to any one of the preceding embodiments, or a pharmaceutically acceptable salt thereof, wherein E is a monocyclic 4-6 membered heterocyclyl.

Embodiment 12. A compound according to any one of the preceding embodiments, or a pharmaceutically acceptable salt thereof, wherein E is a monocyclic 4-6 membered heteroaryl.

Embodiment 13. A compound according to any one of the preceding embodiments, or a pharmaceutically acceptable salt thereof, wherein the monocyclic 4-6 membered heterocyclyl contains one or two nitrogen atoms.

Embodiment 14. A compound according to any one of the preceding embodiments, or a pharmaceutically acceptable salt thereof, wherein the 5-6 membered heteroaryl contains one nitrogen atom.

Embodiment 15. A compound according to any one of the preceding embodiments, or a pharmaceutically acceptable salt thereof, wherein the 4-6 membered heterocyclyl and the 5-6 membered heteroaryl is optionally substituted with one two, or three substituents.

Embodiment 16. A compound according to any one of the preceding embodiments, or a pharmaceutically acceptable salt thereof, wherein the substituents are independently selected from the group consisting of linear or branched $C_1$-$C_3$alkyl, —OH, =O, —$SO_2$R.

Embodiment 17. A compound according to any one of the preceding embodiments, or a pharmaceutically acceptable salt thereof, wherein R is independently selected from linear or branched $C_1$-$C_3$alkyl, monocyclic 5-6 membered heterocyclyl and $NR^1R^2$.

Embodiment 18. A compound according to any one of the preceding embodiments, or a pharmaceutically acceptable salt thereof, wherein the monocyclic 5-6 membered heterocyclyl is optionally substituted with a $C_1$-$C_3$alkyl or $NR^3R^4$.

Embodiment 19. A compound according to any one of the preceding embodiments, or a pharmaceutically acceptable salt thereof, wherein $R^1$ and $R^2$ is independently selected from H and $C_1$-$C_3$ alkyl. A compound according to any one of the preceding embodiments, or a pharmaceutically acceptable salt thereof, wherein $C_1$-$C_3$ alkyl is optionally substituted with $NR^3R^4$.

Embodiment 20. A compound according to any one of the preceding embodiments, or a pharmaceutically acceptable salt thereof, wherein each $R^3$ and $R^4$ is independently selected from H or methyl.

Embodiment 21. The compound according to any one of the preceding embodiments, or a pharmaceutically acceptable salt thereof, wherein $G^1$ is linear or branched $C_1$-$C_4$ alkyl optionally substituted with one, two, or three substituents independently selected from cyclopropyl and linear or branched $C_1$-$C_3$ alkyl.

Embodiment 22. The compound according to any one of the preceding embodiments, or a pharmaceutically acceptable salt thereof, wherein $G^1$ is $C_3$-$C_4$ cycloalkyl optionally substituted with one, two, or three substituents independently selected from and linear or branched $C_1$-$C_3$ alkyl.

Embodiment 23. The compound according to any one of the preceding embodiments, or a pharmaceutically acceptable salt thereof, wherein $G^1$ is linear or branched $C_1$-$C_4$ alkoxy optionally substituted with one, two, or three substituents independently selected from cyclopropyl and linear or branched $C_1$-$C_3$ alkyl.

Embodiment 24. The compound of embodiment 1, having Formula (Ia), or a pharmaceutically acceptable salt thereof:

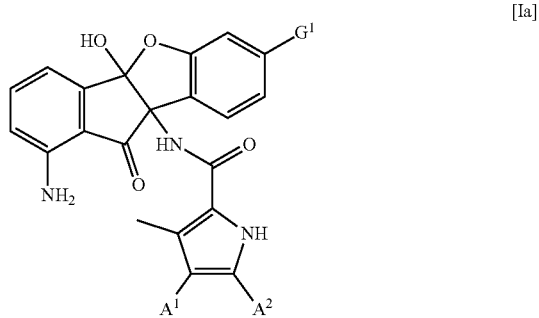

[Ia]

wherein $A^1$ is selected from the group consisting of H, linear or branched $C_1$-$C_3$ alkyl, and $SO_2R$; and $A^2$ is selected from the group consisting of H and $SO_2R$.

Embodiment 25. The compound of the preceding embodiment, wherein $A^1$ is methyl or $SO_2CH_3$.

Embodiment 26. The compound of the preceding embodiments, wherein $A^2$ is $SO_2R$, and R is selected from the group consisting of $CH_3$; monocyclic 5-6 membered heterocyclyl containing one or two nitrogen atoms and substituted with $CH_3$ or $N(CH_3)_2$; and $NR^1R^2$.

Embodiment 27. The compound of embodiment 1, having Formula (Ib), or a pharmaceutically acceptable salt thereof:

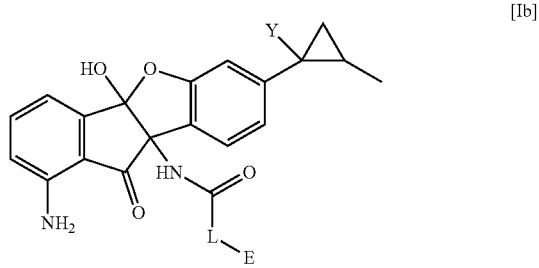

[Ib]

wherein Y is H or $CH_3$.

Embodiment 28. The compound of embodiment 1, having Formula (Ic), or a pharmaceutically acceptable salt thereof:

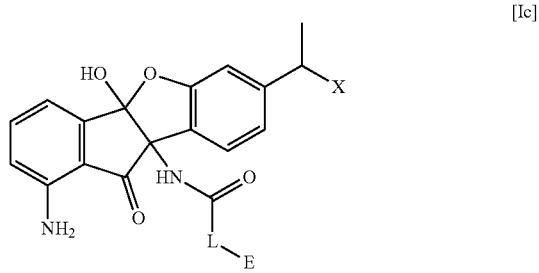

[Ic]

wherein X is selected from the group consisting of: methyl, ethyl, and cyclopropyl Embodiment 29. The compound of any of the preceding embodiments of any of Examples or a pharmaceutically acceptable salt thereof selected from the group consisting of: N-((4bR,9bR)-1-amino-4b-hydroxy-7-((1R,2R)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide; N-((4bR,9bR)-1-amino-4b-hydroxy-7-((1S, 2R)-2-methylcyclopropyl)-10-oxo-4b,10-dihydro-9bH-indeno[1,2-b]benzofuran-9b-yl)-2-(azetidin-1-yl) acetamide; N-((4bR,9bR)-1-amino-7-((S)-1-cyclopropylethyl)-4b-hydroxy-10-oxo-4b,10-dihydro-9bH-indeno[1,2-b]benzofuran-9b-yl)-6-hydroxypicolinamide; N-(1-amino-4b-hydroxy-7-isopropyl-10-oxo-4b,10-dihydro-9bH-indeno[1,2-b]benzofuran-9b-yl)-5-(N-(2-(dimethylamino)ethyl)sulfamoyl)-3,4-dimethyl-1H-pyrrole-2-carboxamide; N-((4bR,9bR)-1-amino-7-((S)-1-cyclopropylethyl)-4b-hydroxy-10-oxo-4b,10-dihydro-9bH-indeno[1,2-b]benzofuran-9b-yl)-2-(azetidin-1-yl) acetamide; N-(1-amino-7-((1R,2S)-1,2-dimethylcyclopropyl)-4b-hydroxy-10-oxo-4b,10-dihydro-9bH-indeno[1,2-b]benzofuran-9b-yl)-3-methyl-4-(methylsulfonyl)-1H-pyrrole-2-carboxamide; N-(1-amino-4b-hydroxy-7-(2-methylcyclobutyl)-10-oxo-4b,10-dihydro-9bH-indeno[1,2-b]benzofuran-9b-yl)-3-methyl-4-(methylsulfonyl)-1H-pyrrole-2-carboxamide; N-((4bR,9bR)-1-amino-7-((R)-1-cyclopropylethyl)-4b-hydroxy-10-oxo-4b,10-dihydro-9bH-indeno[1,2-b]benzofuran-9b-yl)-6-hydroxypicolinamide; N-(1-Amino-4b-hydroxy-7-((trans)-2-methylcyclopropyl)-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide; (2S,3S)—N-(1-amino-7-((R)-1-cyclopropylethyl)-4b-hydroxy-10-oxo-4b, 10-dihydro-9bH-indeno[1,2-b]benzofuran-9b-yl)-2-(dimethylamino)-3-hydroxybutanamide; N-(1-amino-4b-hydroxy-7-((1S,2S)-2-methylcyclopropyl)-10-oxo-4b,10-dihydro-9bH-indeno[1,2-b]benzofuran-9b-yl)-5-(((S)-3-(dimethylamino)pyrrolidin-1-yl)sulfonyl)-3-methyl-1H-pyrrole-2-carboxamide; N-((4bR,9bR)-1-amino-4b-hydroxy-7-((trans)-2-methylcyclopropyl)-10-oxo-4b,10-dihydro-9bH-indeno[1,2-b]benzofuran-9b-yl)-3,4-dimethyl-5-((4-methylpiperazin-1-yl)sulfonyl)-1H-pyrrole-2-carboxamide; N-(1-amino-4b-hydroxy-7-isopropyl-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide; N-((4bR,9bR)-1-amino-4b-hydroxy-7-((1S,2S)-2-methylcyclopropyl)-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide; (2S,3S)—N-((4bR,9bR)-1-amino-7-((S)-1-cyclopropylethyl)-4b-hydroxy-10-oxo-4b,10-dihydro-9bH-indeno[1,2-b]benzofuran-9b-yl)-2-(dimethylamino)-3-hydroxybutanamide; N-(1-amino-4b-hydroxy-7-((1R,2S)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide; N-((4bR,9bR)-1-amino-7-((R)-1-cyclopropylethyl)-4b-hydroxy-10-oxo-4b,10-dihydro-9bH-indeno[1,2-b]benzofuran-9b-yl)-2-(azetidin-1-yl) acetamide; N-((4bR,9bR)-1-amino-7-((S)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide; N-((4bR,9bR)-1-amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide; N-((4bS,9bS)-1-amino-4b-hydroxy-7-isopropoxy-10-oxo- 4b,10-dihydro-9bH-indeno[1,2-b]benzofuran-9b-yl)-3-methyl-5-((4-methylpiperazin-1-yl)sulfonyl)-1H-pyrrole-2-carboxamide; N-(1-amino-4b-hydroxy-7-((1S,2R)-2-methylcyclopropyl)-10-oxo-4b,10-dihydro-9bH-indeno[1,2-b]benzofuran-9b-yl)-3-methyl-5-(methylsulfonyl)-1H-pyrrole-2-carboxamide; N-((4bR,9bR)-1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide; N-(1-amino-7-(sec-butyl)-4b-hydroxy-10-oxo-4b,10-dihydro-9bH-indeno[1,2-b]benzofuran-9b-yl)-3-methyl-4-(methylsulfonyl)-1H-pyrrole-2-carboxamide; N-(1-amino-4b-hydroxy-7-((1S,2R)-2-methylcyclopropyl)-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide; N-(1-amino-4b-hydroxy-7-isopropyl-10-oxo-4b,10-dihydro-9bH-indeno[1,2-b]benzofuran-9b-yl)-3,5-dimethyl-4-sulfamoyl-1H-pyrrole-2-carboxamide; N-(1-amino-4b-hydroxy-7-((1R,2S)-2-methylcyclopropyl)-10-oxo-4b,10-dihydro-9bH-indeno[1,2-b]benzofuran-9b-yl)-3-methyl-5-(methylsulfonyl)-1H-pyrrole-2-carboxamide; N-(1-amino-4b-hydroxy-7-((1S,2R)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide and N-((4bR,9bR)-1-amino-4b-hydroxy-7-((1S,2S)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide. This embodiment includes each of the Examples represented in the Table of Bioactivity Data herein.

Embodiment 30. A compound including each or any of the Examples represented in the Table of Bioactivity Data herein.

Embodiment 31. A compound of Chemical Formula I to III or of any one of the embodiments herein, a pharmaceutically acceptable salt thereof or optical isomer thereof for prevention or treatment of a viral disease.

Embodiment 32. A pharmaceutical composition for prevention or treatment of a viral disease, comprising the compound of Chemical Formula I to III or of any one of the embodiments herein, a pharmaceutically acceptable salt thereof or optical isomer thereof and a pharmaceutically acceptable diluent or excipient.

Embodiment 33. The compound set forth in the embodiments herein, the pharmaceutically acceptable salt thereof or optical isomer thereof or the pharmaceutical composition as set forth in the embodiments herein, wherein the viral disease is caused by coxsackievirus. The compound set forth in the embodiments herein, a pharmaceutically acceptable salt thereof or optical isomer thereof or the pharmaceutical composition as set forth in the embodiments herein, wherein the viral disease is caused by poliovirus. The compound set forth in the embodiments herein, a pharmaceutically acceptable salt thereof or optical isomer thereof or the pharmaceutical composition as set forth in the embodiments herein, wherein the viral disease is caused by echovirus. The compound set forth in the embodiments herein, a pharmaceutically acceptable salt thereof or optical isomer thereof or the pharmaceutical composition as set forth in the embodiments herein, wherein the viral disease is caused by enterovirus. The compound set forth in the embodiments herein, a pharmaceutically acceptable salt thereof or optical isomer thereof or the pharmaceutical composition as set forth in the embodiments herein, wherein the viral disease is caused by rhinovirus. The compound set forth in the embodiments herein, a pharmaceutically acceptable salt thereof or optical isomer thereof or the pharmaceutical composition as set forth in the embodiments herein, wherein the viral disease is caused by picornavirus. The compound set forth in the embodiments herein, a pharmaceutically acceptable salt thereof or optical isomer thereof or the pharmaceutical composition as set forth in the embodiments herein, wherein the viral disease is poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

Embodiment 34. Use of a compound of Chemical Formula 1 to III or of any one of the embodiments herein, or a pharmaceutically acceptable salt thereof or optical isomer thereof for the prevention or treatment of a viral disease.

Embodiment 35. The use of the embodiments herein, wherein the viral disease is caused by coxsackievirus.

Embodiment 36. The use of the embodiments herein, wherein the viral disease is caused by poliovirus.

Embodiment 37. The use of the embodiments herein, wherein the viral disease is caused by echorovirus.

Embodiment 38. The use of the embodiments herein, wherein the viral disease is caused by enterovirus.

Embodiment 39. The use of the embodiments herein, wherein the viral disease is caused by rhinovirus.

Embodiment 40. The use of the embodiments herein, wherein the viral disease is caused by picornavirus.

Embodiment 41. The use of the embodiments herein, wherein the viral disease is poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

These compounds are novel and useful as intermediates for preparation of the compounds of Formula (I)-(III) described herein.

Another embodiment of the invention provides a compound as described above, or a pharmaceutically acceptable salt thereof, as a medicament.

Also within the scope of this invention is the use of a compound of formula (I), or a pharmaceutically acceptable salt thereof, for the manufacture of a medicament for the treatment or prevention of a viral disease and/or infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a viral infection or other virus in a human being having or at risk of having the infection.

The invention also provides the use of a pharmaceutical composition as described hereinabove for the treatment of viral disease or other virus infection in a human being having or at risk of having the disease.

Another aspect of the invention involves a method of treating or preventing a virus disease and/or infection in a human being by administering to the human being an antivirally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat a herpesvirus disease and/or infection; and packaging material comprising a label which indicates that the composition can be used to treat disease and/or infection by a virus; wherein the composition comprises a compound of formula (I) according to this invention or a pharmaceutically acceptable salt thereof.

Still another aspect of this invention relates to a method of inhibiting the replication of a virus, comprising exposing the virus to an effective amount of the compound of formula (I), or a salt thereof, under conditions where replication of the virus is inhibited. This method can be practiced in vitro or in vivo.

Further included in the scope of the invention is the use of a compound of formula (I), or a salt thereof, to inhibit the replication of a virus.

In one embodiment, the invention provides a pharmaceutical composition comprising a compound of the present invention and another therapeutic agent(s). Optionally, the pharmaceutical composition may comprise a pharmaceutically acceptable carrier, as described above. In some embodiments, the compound of Formula (I) is co-administered with at least one additional agent selected from: including another virus inhibitor.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, e.g. from 0.1 to 50 mg/kg of body weight. Each dosage unit may conveniently contain from 5% to 95% active compound (w/w). Sometimes such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and sometimes between about 10 and 80% of the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being.

Many compounds of the invention contain one or more chiral centers. These compounds may be made and used as single isomers or as mixtures of isomers. Methods for separating the isomers, including diastereomers and enantiomers, are known in the art, and examples of suitable methods are described herein. In certain embodiments, the compounds of the invention are used as a single substantially pure isomer, meaning at least 90% of a sample of the compound is the specified isomer and less than 10% of the sample is any other isomer or mixture of isomers. In some embodiments, at least 95% of the sample is a single isomer. Selection of a suitable isomer is within the ordinary level of skill, as one isomer will typically be more active in the herpesvirus DNA polymerase in vitro assay described herein and will be the single isomer. Where in vitro activity differences between isomers are relatively small, e.g. less than about a factor of 4, a single isomer may be selected based on activity level against viral replication in cell culture, using methods such as those described herein: e.g. the isomer having a lower IC-50 or EC-50.

The compounds of the invention may be synthesized by the general synthetic routes below, specific examples of which are described in more detail in the Examples.

The invention also provides methods of making compounds of Formula I as described herein and intermediates useful for preparation of compounds of Formula (I). The invention thus also includes a method to make a compound of Formula (I). The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is intended to represent unlabeled forms as well as isotopically labeled forms of the compounds of the present invention having up to three atoms with non-natural isotope distributions, e.g., sites that are enriched in deuterium or $^{13}$C or $^{15}$N. Isotopically labeled compounds have structures depicted by the formulas given herein except that one or more atoms are replaced by an atom having a selected atomic mass or mass number other than the natural-abundance mass distribution. Examples of isotopes that can be usefully over-incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^3$S, $^{36}$Cl, $^{125}$I respectively. The invention includes various isotopically labeled compounds of the present invention, for example those into which radioactive isotopes, such as $^3$H and $^{14}$C, or those in which non-radioactive isotopes, such as $^2$H and $^{13}$C are present at levels substantially above normal isotope distribution. Such isotopically labelled compounds are useful in metabolic studies (with $^{14}$C, for example), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent typically employed. Labeled samples may be useful with quite low isotope incorporation, such as where a radiolabel is used to detect trace amounts of the compound.

Further, more extensive substitution with heavier isotopes, particularly deuterium (i.e., $^2$H or D), may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention, and typically a sample of a compound having deuterium as a substituent has at least 50% deuterium incorporation at the labeled position(s). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. Compounds of the present invention exhibit oral bioavailability, so in some embodiments, the compound may be administered orally.

A compound of the present invention may also be used in combination with other agents (combination partners), e.g., an additional antiviral agent that is or is not of the formula I, for treatment of a viral infection in a subject.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

In certain embodiments of the present invention, a compound of the present invention is used in combination with a second antiviral agent, such as those named herein.

The second antiviral agent may be administered in combination with the compounds of the present inventions wherein the second antiviral agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antiviral agent may provide synergistic activity. The compound of the invention and second antiviral agent may be administered together, separately but simultaneously, or sequentially.

An "effective amount" of a compound is that amount necessary or sufficient to treat or prevent a viral infection and/or a disease or condition described herein. In an example, an effective amount of a viral inhibitor of Formula I is an amount sufficient to treat viral infection in a subject. In another example, an effective amount of the inhibitor is an amount sufficient to treat a viral infection, in a subject in need of such treatment. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a viral infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (e.g., 0.5 to 90%) of at least one compound of Formula (I) or any subgenus thereof as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, sometimes from about 5 percent to about 70 percent, sometimes from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or e.g., in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration may comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, sometimes from about 0.01 to about 50 mg per kg per day, and still sometimes from about 0.1 to about 20 mg per kg per day. An effective amount is that amount which prevents or treats a viral infection.

If desired, the effective daily dose of the active compound may be administered as a single dose per day, or as two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered by infusion are typically administered in one to three doses per day. When multiple doses are administered within a day, the doses may be administered at intervals of about 4 hours, about 6 hours, about 8 hours or about 12 hours.

While it is possible for a compound of the present invention to be administered alone, sometimes the compound may be administered as a pharmaceutical composition such as those described herein. Thus methods of using the compounds of the invention include administering the compound as a pharmaceutical composition, wherein at least one compound of the invention is admixed with a pharmaceutically acceptable carrier prior to administration.

General Synthetic Procedures

The compounds as described herein may be synthesized by the general synthetic routes below, specific examples of which are described in more detail in the Examples.

All starting materials, building blocks, reagents, acids, bases, dehydrating agents, solvents, and catalysts utilized to synthesize the compounds of the invention are either commercially available or can be produced by organic synthesis methods known to one of ordinary skill in the art (Houben-Weyl 4th Ed. 1952, Methods of Organic Synthesis, Thieme, Volume 21).

LIST OF ABBREVIATIONS

Ac acetyl
ACN or MeCN Acetonitrile
AcOEt/EtOAc Ethyl acetate
AcOH acetic acid
aq aqueous
Bn benzyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene Boc₂O di-tert-butyl dicarbonate
DCE 1,2-Dichloroethane
DCM Dichloromethane
DIAD Diisopropyl azodicarboxylate
DiBAl-H Diisobutylaluminum Hydride
DIPEA or DIEA N-Ethyldiisopropylamine
DMA N,N-dimethylacetamide
DMAP Dimethylaminopyridine
DMF N,N-Dimethylformamide
DMSO Dimethylsulfoxide
EDC 1-Ethyl-3-(3-dimethylaminopropyl)carbodiimide
EI Electrospray ionisation
Et₂O Diethylether
Et₃N Triethylamine
Ether Diethylether
EtOAc Ethyl acetate
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
H₂O Water
IPA isopropanol
L liter(s)
LC-MS Liquid Chromatography Mass Spectrometry
LiHMDS Lithium bis(trimethylsilyl)amide
MgSO₄ Magnesium Sulfate
Me methyl
MeI Iodomethane
MeOH Methanol
mg milligram
min minute(s)
mL milliliter
MS Mass Spectrometry
MsCl methanesulfonyl chloride
NaHCO₃ Sodium Bicarbonate
Na₂SO₄ Sodium Sulfate
NH₂OH hydroxylamine
Pd/C palladium on charcoal
Pd(OH)₂ palladium hydroxide
PG protecting group
Ph phenyl
Ph₃P triphenyl phosphine
Prep Preparative
Rf ratio of fronts
RP reverse phase
Rt Retention time
RT Room temperature
SFC Supercritical Fluid Chromatography
SiO₂ Silica gel
SOCl₂ Thionyl Chloride
T3P® Propylphosphonic acid anhydride
TBAF Tetrabutylammonium fluoride
TBDMS t-Butyldimethylsilyl
TBTU O-(Benzotriazol-1-yl)-N,N,N',N'-tetramethyluronium tetrafluoroborate
TEA Triethylamine
TFA Trifluoroacetic acid
THF Tetrahydrofuran
TLC Thin Layer Chromatography
TsCl toluene sulfonyl chloride
TsOH toluene sulfonic acid Compounds of the present invention are prepared from commonly available compounds using procedures known to those skilled in the art in view of the examples and schemes provided herein.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005, 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der Organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent sometimes being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g., using chromatographic methods, distribution methods, (re-) crystallization, and the like.

High Resolution Mass Spectrometry by LC-MS

ESI-MS data were recorded using a LTQ-XL Orbitrap mass spectrometer (ThermoFisher Scientific) with electrospray ionization source. The resolution of the MS system was approximately 30000. The drug candidate was infused into the mass spectrometer by UPLC (Acquity, Waters) from sample probe. The separation was performed on Acquity UPLC BEH C18 1×50 mm column at 0.15 mL/min flow rate with the gradient from 5% to 95% in 3 min. Solvent A was Water with 0.1% Trifluoroacetic acid and solvent B was 75% Methanol and 25% Isopropyl alcohol with 0.1% Trifluoroacetic acid. The mass accuracy of the system has been found to be <5 ppm.

EXAMPLES

The invention is further illustrated by the following examples, which should not be construed as limiting. The assays used throughout the Examples are well established in the art: demonstration of efficacy in these assays is generally regarded as predictive of efficacy in subjects.

The compounds of the invention can be produced by organic synthesis methods known to one of ordinary skill in the art with reference to the following reaction schemes and examples. General methods for synthesis of compounds of Formula (I) are provided in Schemes below.

Example 1: N-((4bR,9bR)-1-amino-4b-hydroxy-7-((1R,2R)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide (33)

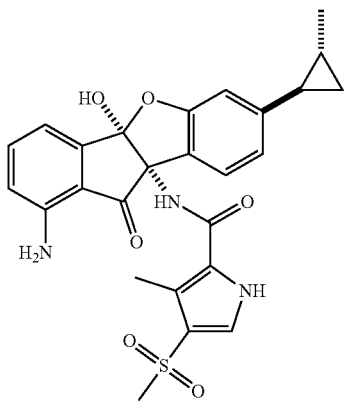

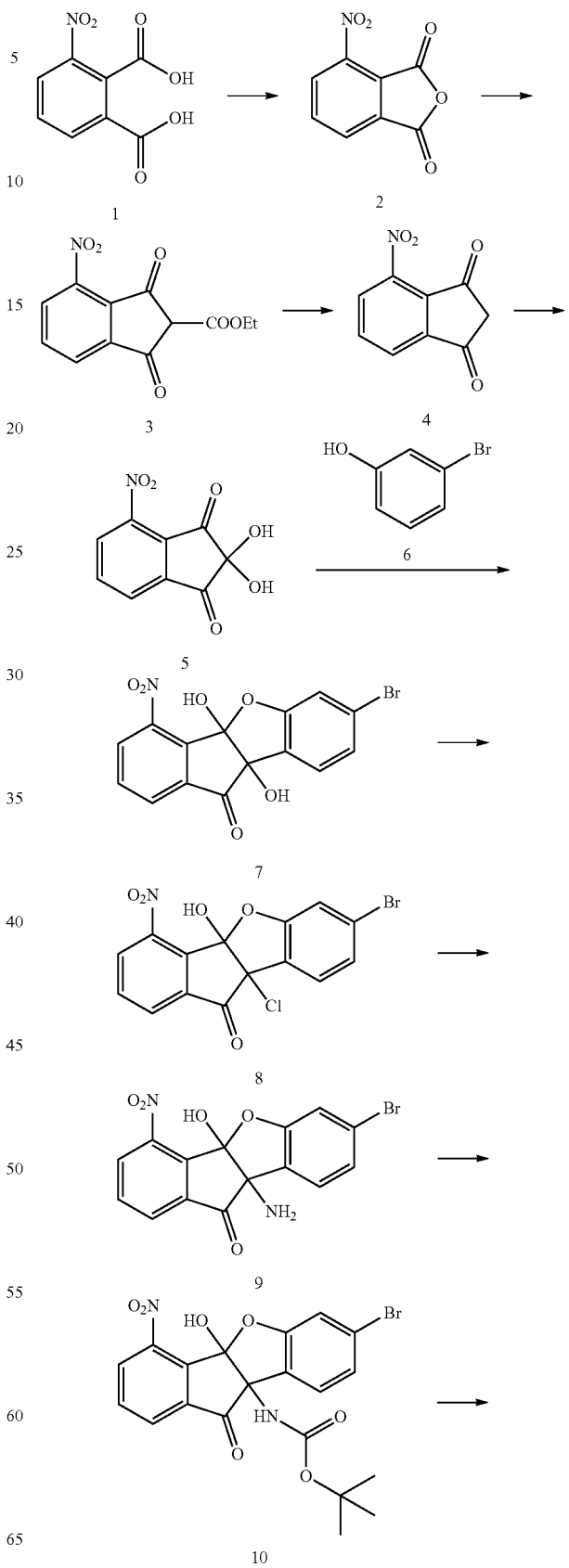

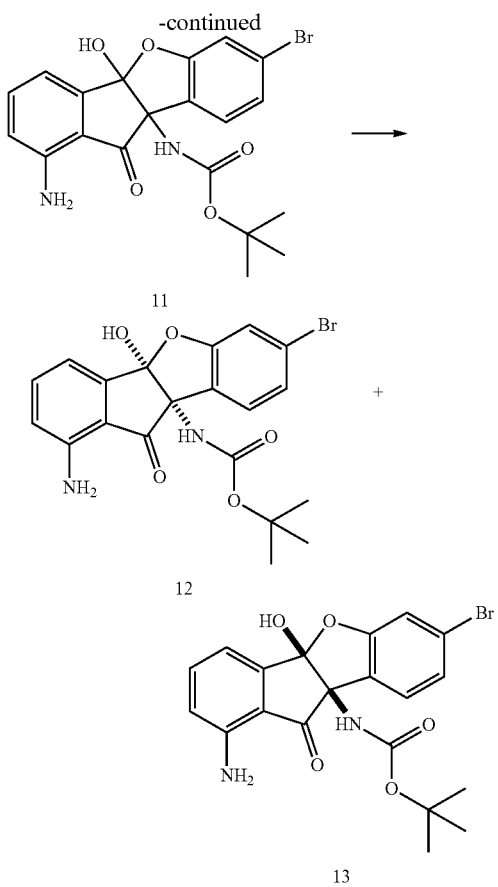

4-Nitroisobenzofuran-1,3-dione (2)

A initial suspension of the 3-nitrophthalic acid 1 (1.0 kg, 4.7 moles) in $Ac_2O$ (1 Ltr), was refluxed at 140° C. for 2.5 hours. This was then cooled down to 80° C. and added slowly to diethyl ether (4 Ltr) with vigorous stirring. The precipitate was collected by filtration over Buckner funnel and was washed with $Et_2O$ to give the product.

Ethyl 4-nitro-1,3-dioxo-2,3-dihydro-1H-indene-2-carboxylate (3)

To a suspension of the anhydride 2 (50 g, 0.26 moles) in dry DCM (260 mL), ethyl acetoacetate (42 mL, 0.31 moles) and $Ac_2O$ (48.5 mL, 0.52 moles) was added at ambient temperature. To this suspension $Et_3N$ (108 mL, 0.78 moles) was charged at room temperature dropwise (exothermic) in a duration of 30 minutes. Few mL addition of TEA was added. This was stirred at the same temperature for 15 mins more and then DCM was evaporated off. The crude obtained was then dissolved in 2 liters of water and cooled to 0° C. This was fixed with an overhead stirrer and under vigorous stirring conditions 300 mL of 2 N HCl was added to it dropwise maintaining the temperature below 0° C. A precipitate starts forming slowly. This was stirred at 0° C. for more 15 mins and then filtered over Buckner funnel and washed with ice cold water (500 mL). This was then air dried for three days to get a solid as the product.

4-Nitro-1H-indene-1,3(2H)-dione (4)

Ethyl 4-nitro-1,3-dioxo-2,3-dihydro-1H-indene-2-carboxylate 3 (272.5 g, 1.04 moles) was taken in 1 litre of MeCN:water (20:1, 1.0 M). This suspension was charged with TFA (60 mL, 1.14 moles) slowly at room temperature and then kept for heating at 50° C. After 4 hrs, the reaction mass was concentrated over rotavapour until approximately 100 mL of solvent remained. The precipitated solid was then filtered off over Buckner funnel and washed with (1:1) $CHCl_3$:Hexane. This gave the product and the filtrate was again concentrated to get more product in second crop.

2,2-Dihydroxy-4-nitro-1H-indene-1,3(2H)-dione (5)

4-Nitro-1H-indene-1,3(2H)-dione 4 (10.0 g, 52.3 mmol) was taken in AcOH: dioxane (1:10, 105 mL, 0.5 M). This was charged with $SeO_2$ (12.77 g, 115.1 mmol) and refluxed for 5 hours at 105-110° C. The reaction mass was then filtered over CELITE under hot conditions and then concentrated off the volatiles to get the crude 2,2-dihydroxy-4-nitro-1H-indene-1,3(2H)-dione.

7-Bromo-4b,9b-dihydroxy-4-nitro-4b,9b-dihydro-10H-indeno[1,2-b]benzofuran-10-one (7)

The crude 2,2-dihydroxy-4-nitro-1H-indene-1,3(2H)-dione 5 was then taken in gl. AcOH (210 mL, 0.25 mmol) and this was charged with 3-bromo phenol 6 (9.96 g, 57.5 mmol) and kept at reflux for next 12 hours. The reaction mass was concentrated off and taken in EA (500-600 mL). This was filtered over CELITE and residue washed with EA. The filtrate was washed with water (200 mL×2) and brine (100 mL). This was dried over anhyd. $Na_2SO_4$ and concentrated off to get the crude product. The crude was purified over silica gel column chromatography (35-40% EA in hexanes) twice to get the pure product.

7-Bromo-9b-chloro-4b-hydroxy-4-nitro-4b,9b-dihydro-10H-indeno[1,2-b]benzofuran-10-one (8)

7-bromo-4b,9b-dihydroxy-4-nitro-4b,9b-dihydro-10H-indeno[1,2-b]benzofuran-10-one 7 (39.5 g, 0.105 mol) was taken in DCM (520 mL, 0.2 M) and charged with oxalyl chloride (11 mL, 0.13 mol) at room temperature. To this DMF (40 mL, 0.53 mol) was added slowly (0.05 mL/min 30 mins and 0.1 mL/min 30 mins and then fast) and left to stir at ambient temperature (30° C.). The reaction mixture was then stirred at rt (20° C.) for next 12 hours. The reaction mixture was diluted with water (~300 mL). The aq. layer was extracted with DCM (~500 mL×2). The combined org, layer was washed with water (~300 ml) and brine (~300 mL). This was dried over anhyd. $Na_2SO_4$ and concentrated off to get the crude product. Crude was purified over silica gel column chromatography (10-30% EA in hexane) to get the pure product.

9b-Amino-7-bromo-4b-hydroxy-4-nitro-4b,9b-dihydro-10H-indeno[1,2-b]benzofuran-10-one (9)

9b-Chloro-4b-hydroxy-4-nitro-8-(trifluoromethyl)-4b,9b-dihydro-10H-indeno[1,2-b]benzofuran-10-one 8 (21.2 g, 53.4 mmol) was taken in THF (530 mL, 0.1 M) and cooled to −40° C. This was charged with 2.0 M $NH_3$ in IPA (54 mL, 0.11 mmol) at same temperature and left to stir for next 3 h. The reaction mixture was diluted with water (~150 mL) and brine (150 mL). The aq. layer was extracted with EA (~300 mL×2). The combined org, layer was washed with brine (~100 mL). This was dried over anhyd. $Na_2SO_4$ and concentrated off to get the crude product. Crude was purified over silica gel column chromatography (20-30% EA in hexanes with 20% DCM as cosolvent) to get the pure product.

Tert-butyl (7-bromo-4b-hydroxy-4-nitro-10-oxo-4b,10-dihydro-9bH-indeno[1,2-b]benzofuran-9b-yl)carbamate (10)

Boc anhydride (8.74 g, 40 mmol) and Molecular 12 (0.69 g, 2.67 mmol) was added to a solution of a racemic mixture of 9b-amino-7-bromo-4b-hydroxy-4-nitro-4b,9b-dihydro-10H-indeno[1,2-b]benzofuran-10-one 9 (10.1 g, 31 mmol) in THF (5.0 mL, 5.0 M) and stirred at 30° C. for next 72 h. The reaction mass was concentrated and purified. The crude was purified over silica gel column chromatography (10%-30% EA in hexanes with 5-10% DCM) to get the pure product.

Tert-butyl (1-amino-7-bromo-4b-hydroxy-10-oxo-4b,10-dihydro-9bH-indeno[1,2-b]benzofuran-9b-yl)carbamate (11)

A mixture racemic tert-butyl (7-bromo-4b-hydroxy-4-nitro-10-oxo-4b,10-dihydro-9bH-indeno[1,2-b]benzofuran-9b-yl)carbamate 10 (10.3 g, 21.5 mmol) was taken in EtOH:water (10:1, 110.0 mL, 0.20 M), and to this Fe powder (3.57 g, 63.9 mmol) was charged followed by Conc. HCl (0.8 mL, cat.). This was refluxed at 90° C. for next 3 hours. The reaction mass was filtered over CELITE under warm conditions using hot EA (50-100 mL). The filtrate was concentrated off & taken in EA (~1000-1200 mL) and washed with water (~300-500 mL) and brine (~300 mL). This was dried over anhyd. $Na_2SO_4$ and concentrated to get the crude. Crude was purified over silica gel column chromatography (10-30% EA in hx) to get the pure product.

Tert-butyl ((4bR,9bR)-1-amino-7-bromo-4b-hydroxy-10-oxo-4b,10-dihydro-9bH-indeno[1,2-b]benzofuran-9b-yl)carbamate (12) and tert-butyl ((4bS,9bS)-1-amino-7-bromo-4b-hydroxy-10-oxo-4b,10-dihydro-9bH-indeno[1,2-b]benzofuran-9b-yl)carbamate (13)

Tert-butyl (1-amino-7-bromo-4b-hydroxy-10-oxo-4b,10-dihydro-9bH-indeno[1,2-b]benzofuran-9b-yl)carbamate (11) (7000 mg) was purified by chiral chromatography using (AD column, HPLC=20 ml/min, Heptane/EtOH=70/30, 724 psi) to give 3010 mg of tert-butyl ((4bR,9bR)-1-amino-7-bromo-4b-hydroxy-10-oxo-4b,10-dihydro-9bH-indeno[1,2-b]benzofuran-9b-yl)carbamate (12) as (peak 2, tR 15.59 min.); 1H NMR (500 MHz, METHANOL-d4) δ: 7.48 (br t, J=7.7 Hz, 1H), 7.37 (br s, 1H), 7.11 (br s, 1H), 7.02 (br d, J=7.1 Hz, 1H), 6.95 (s, 1H), 6.72 (br s, 1H), 1.42 (br s, 5H), 1.13 (br s, 4H) LCMS: 447.2/449.2 [M+H]$^+$ and 3060 mg of tert-butyl ((4bS,9bS)-1-amino-7-bromo-4b-hydroxy-10-oxo-9b,10-dihydro-4bH-indeno[1,2-b]benzofuran-9b-yl)carbamate (13) as (peak 1, tR 8.97 min.); 1H NMR (500 MHz, METHANOL-d4) δ: 7.48 (br t, J=7.6 Hz, 1H), 7.37 (br s, 1H), 7.11 (br s, 1H), 7.02 (br d, J=6.9 Hz, 1H), 6.95 (s, 1H), 6.72 (br s, 1H), 1.42 (br s, 5H), 1.13 (br s, 4H) LCMS: 447.2/449.2 [M+H]$^+$.

Scheme-2

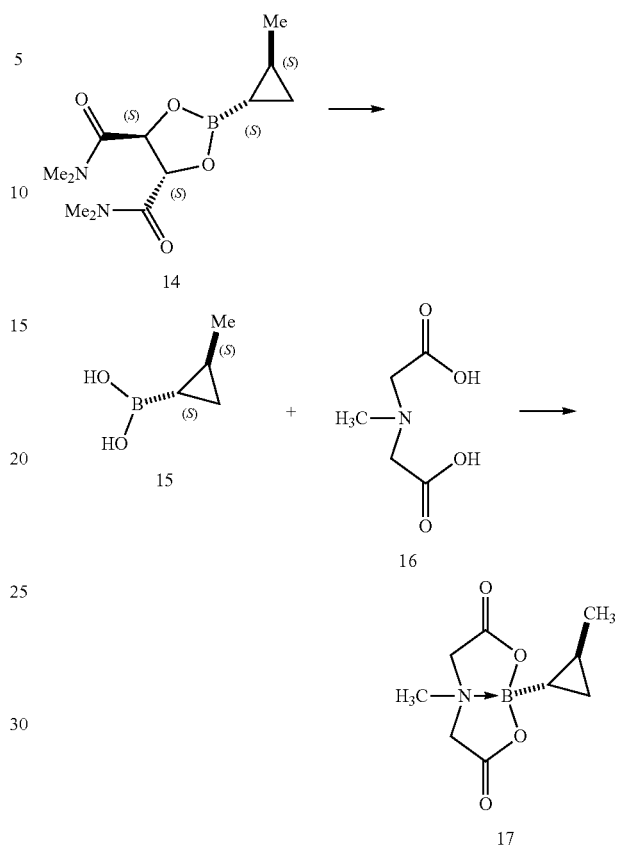

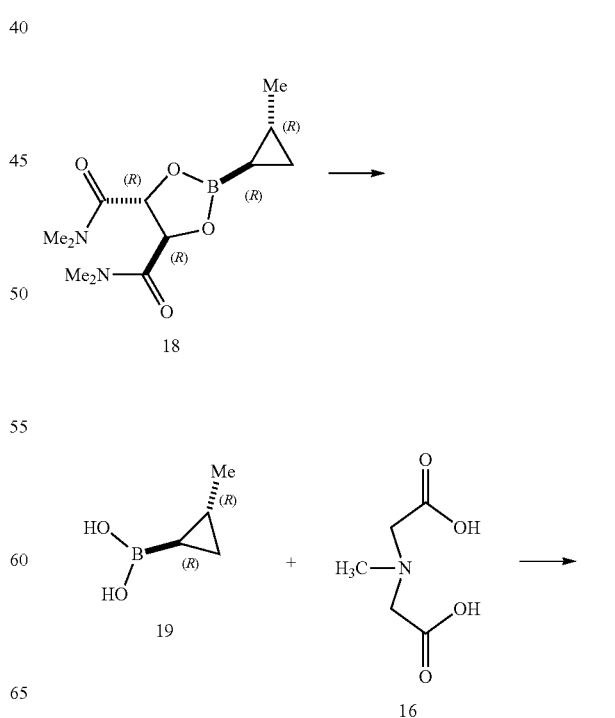

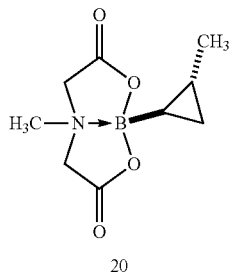

Intermediate (14 and 18) was prepared according to literature reported in *J. Am. Chem. Soc.* 2013, 135, 82-85.

((1S,2S)-2-Methylcyclopropyl)boronic acid (15)

A solution of (4S,5S)—N4,N4,N5,N5-tetramethyl-2-((1S,2S)-2-methylcyclopropyl)-1,3,2-dioxaborolane-4,5-dicarboxamide 14 (4.21 g, 14.4 mmol) in Water (145 mL) was stirred for 12 h at rt. The aqueous layer was extracted with ether (100 mL×3) the combined ethereal layer was washed with water and dried over $Na_2SO_4$ and evaporated solvent at low temperature to give product. Crude was forwarded for next step without purification.

6-Methyl-2-((1S,2S)-2-methylcyclopropyl)-1,3,6,2-dioxazaborocane-4,8-dione (17)

To the solution of ((1S,2S)-2-methylcyclopropyl)boronic acid 15 (800 mg, 8.0 mmol) in Toluene:DMSO (80 mL) was added 2,2'-(methylazanediyl)diacetic acid 16 (1.766 mg, 12 mmol) the resulting reaction mass was refluxed at Dean-Stark condition for 3 h. Toluene was evaporated under vacuum, organic layer was diluted with water and aqueous layer was extracted with ethyl acetate (100 mL×3) the combined organic layer was washed with water and dried over $Na_2SO_4$ and evaporated solvent to get crude. Crude was triturated with ether, filtered off the solid and washed with ether to give product.

((1R,2R)-2-Methylcyclopropyl)boronic acid (19)

The solution of (4R,5R)—N4,N4,N5,N5-tetramethyl-2-((1R,2R)-2-methylcyclopropyl)-1,3,2-dioxaborolane-4,5-dicarboxamide 18 (11.3 g, 31.7 mmol, based on previous step starting material) in distilled water (317 mL, 0.1 M) was stirred for 12 h at room temperature. This reaction mixture was extracted with diethyl ether (500 mL×3), the combined organic layer was washed with water (×1), dried over anhydrous $Na_2SO_4$ and concentrated at low temperature to afford the crude product. This crude product was used next step without purification.

6-Methyl-2-((1R,2R)-2-methylcyclopropyl)-1,3,6,2-dioxazaborocane-4,8-dione (20)

To the solution of ((1R,2R)-2-methylcyclopropyl)boronic acid 19 (6.03 g, 60.3 mmol) in Toluene/DMSO (10/1, 300 mL/30 mL) was added 2,2'-(methylazanediyl)diacetic acid 16 (13.3 g, 90.5 mmol), then refluxed for 3 hours under dean-stark condition. The reaction mixture was cooled down to room temperature, diluted with ethyl acetate (500 mL). The organic layer was washed with water (200 mL×4), dried over anhydrous $Na_2SO_4$, filtered and concentrated. To the residue was added diethyl ether then generated desired product. $^1$H NMR (300 MHz, $CDCl_3$) δ 3.92 (d, J=16.6 Hz, 2H), 3.72 (dd, J=16.6, 4.8 Hz, 2H), 3.04 (s, 3H), 1.10 (d, J=5.8 Hz, 3H), 0.70 (dt, J=11.3, 5.7 Hz, 1H), 0.47-0.35 (m, 1H), 0.34-0.22 (m, 1H), −0.61 (dt, J=9.2, 6.1 Hz, 1H).

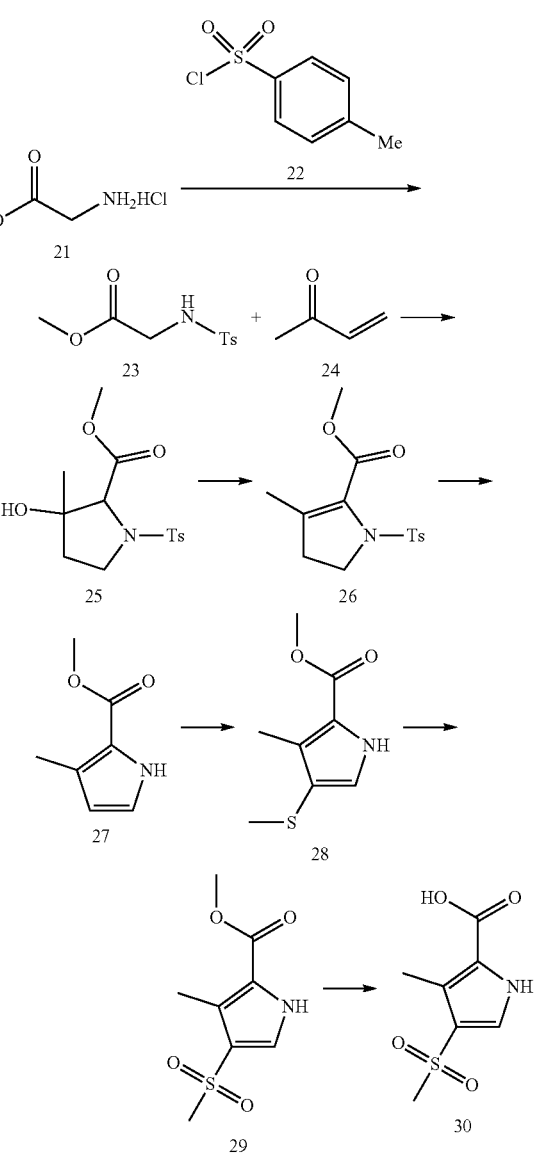

Scheme-3

Methyl tosylglycinate (23)

Methyl glycinate hydrochloride 21 (50.0 g, 398.2 mmol) was dissolved in DCM (800 mL). Then p-Tosylchloride 22 (75.9 g, 398.2 mmol) was added slowly. The reaction mixture was cooled to 0° C. Then DIPEA (208 mL, 1194.7 mmol) was added slowly and the reaction was stirred for 10 minutes at 0° C. The reaction was warmed to 30° C. and stirred for 18 h. Reaction was quenched with 1 N HCl, aqueous layer was extracted with DCM (500 mL×3) and combined organic layer was washed with water (500 mL) and with brine (200 mL). The organic layer was dried over $Na_2SO_4$ evaporated solvent to get crude. The crude was purified by triturating with DCM:Hex to get product.

Methyl 3-hydroxy-3-methyl-1-tosylpyrrolidine-2-carboxylate (25)

Methyl tosylglycinate 23 (58.50 g, 240.5 mmol) and Methyl vinyl ketone 24 (26 mL, 529.0 mmol) were dissolved in THF (241 mL), then was added DBU (79 mL, 529.0 mmol) slowly and the reaction mass was stirred for 12 h at room temperature (30° C.).The reaction mixture was diluted with ether (1000 mL). The organic phase was washed with a solution of 1 N HCl. Once the pH of the aqueous phase was acidic, the organic phase was washed with a solution of 5% Na$_2$CO$_3$ and with water until pH neutral. The organic phase was dried over anhydrous Na$_2$SO$_4$ and evaporated in vacuo to give product. The crude was used in next step without purification.

Methyl 3-methyl-1-tosyl-4,5-dihydro-1H-pyrrole-2-carboxylate (26)

Methyl 3-hydroxy-3-methyl-1-tosylpyrrolidine-2-carboxylate 25 (69 g, 220 mmol) was dissolved in anhydrous pyridine (550 mL), POCl$_3$ (61 mL, 660 mmol) was added slowly and reaction mass was stirred for 12 h at room temperature (30° C.). The reaction mixture was poured into ice-water, aqueous layer was extracted with ether (5 times), and combined organic layer was washed with a 5% HCl solution, once the pH of the aqueous layer was acidic, the organic layer was washed with a solution of 5% Na$_2$CO$_3$, then with water until pH neutral. The organic layer was dried over anhydrous Na$_2$SO$_4$ and evaporated in vacuum. The crude was purified over silica gel column chromatography to give the product.

Methyl 3-methyl-1H-pyrrole-2-carboxylate (27)

Methyl 3-methyl-1-tosyl-4,5-dihydro-1H-pyrrole-2-carboxylate 26 (30 g, 102 mmol) was dissolved in THF (204 mL) and was added DBU (46 mL, 306 mmol) slowly, the resulting reaction mass was stirred at 50° C. for 20 h. The reaction mass was cooled to rt and diluted with ether. The organic layer was washed with 1N HCl then with 5% NaHCO$_3$ and then with water. The organic layer was dried over Na$_2$SO$_4$ and evaporated to get crude. Crude was filtered through silica-gel plug and evaporated solvent to get product.

Methyl 3-methyl-4-(methylthio)-1H-pyrrole-2-carboxylate (28)

Methyl 3-methyl-1H-pyrrole-2-carboxylate 27 (460 mg, 3.3 mmol) and CuI (314 mg, 0.5 mmol) was taken DMSO (3.3 mL, 1.0 M). This was then charged with dimethyldisulfide (0.531 mL, 6.0 mmol) and heated at 110° C. for next 48 hours. The reaction was quenched with water (50 mL) and EA (50 mL). The layers were filtered over CELITE and then separated off. The aq. layer was extracted with EA (50 mL) and combined organic layer was washed with water (30 mL) and brine (30 mL). This was dried over anhyd. Na$_2$SO$_4$ and concentrated off to get the crude. Crude was purified over silica gel column chromatography (10-15% EA in hexanes) to get the product.

Methyl 3-methyl-4-(methylsulfonyl)-1H-pyrrole-2-carboxylate (29)

Methyl 3-methyl-5-(methylthio)-1H-pyrrole-2-carboxylate 28 (185 mg, 1.0 mmol) was taken in MeOH (10 mL) and to this a solution of OXONE (1.85 g, 2.0 mmol) in water (10 mL) was added drop-wise at room temperature. The reaction mass was then stirred at room temperature (25° C.) for next 3 hours. Then the volatiles were removed under reduced pressure and the suspension of solid in water was extracted with EA (70 mL×2) using some amount of water to just dissolve inorganics. The combined organic layer was washed with water (30 ml) and brine (30 ml). This was dried over anhyd. Na$_2$SO$_4$ and concentrated to get the crude. Crude product was purified over silica gel column chromatography (30-40% EA in hexanes) to get the pure product.

3-Methyl-4-(methylsulfonyl)-1H-pyrrole-2-carboxylic acid (30)

To the solution of ethyl 3-methyl-4-(methylsulfonyl)-1H-pyrrole-2-carboxylate 29 (390 mg, 1.68 mmol) in H$_2$O:THF (17 mL) was added LiOH·H$_2$O (353 mg, 8.4 mmol). Then the resulting reaction mass was stirred at 80° C. for 12 hours. Reaction mass was acidified with 1 N HCl, solid precipitated was extracted with ethyl acetate (100 mL×2) combined organic layer was washed with water and with brine solution. Organic layer was dried over anhyd. Na$_2$SO$_4$, solvent was evaporated to get product, which was used as such for next step without purification.

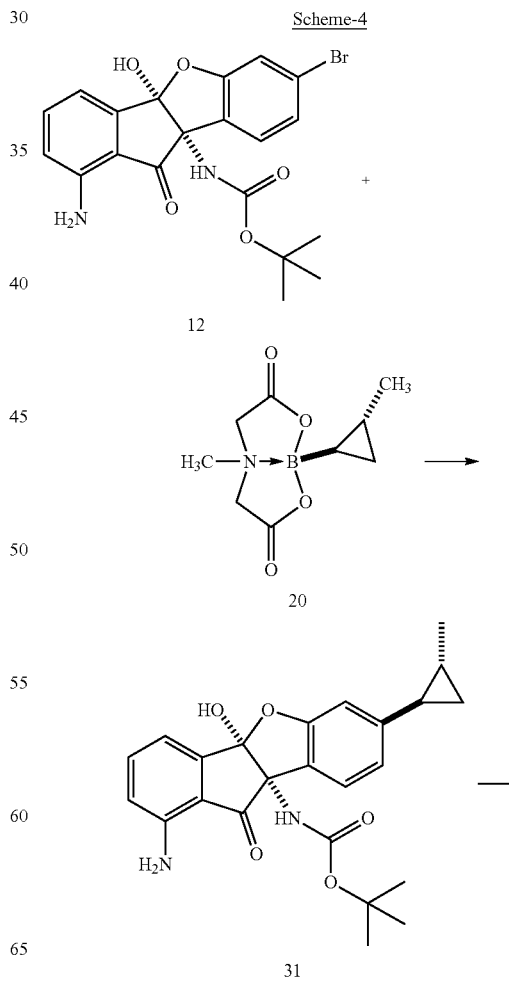

Scheme-4

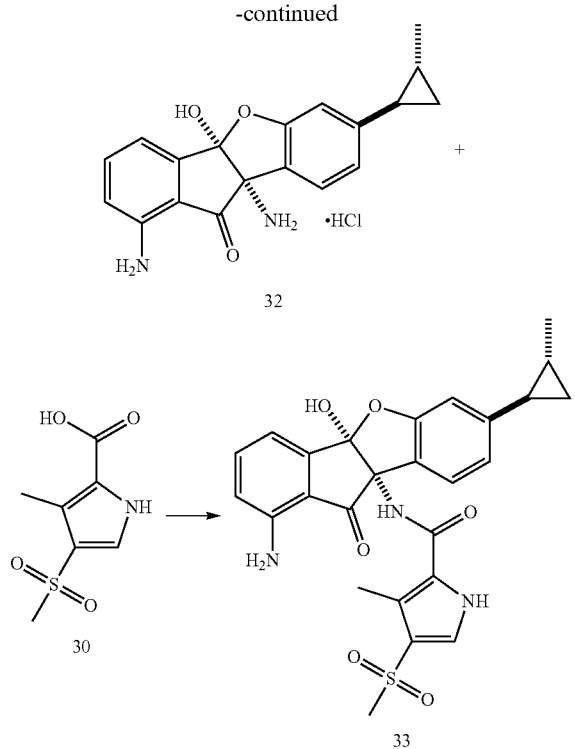

Tert-butyl ((4bR,9bR)-1-amino-4b-hydroxy-7-((1R, 2R)-2-methylcyclopropyl)-10-oxo-4b,10-dihydro-9bH-indeno[1,2-b]benzofuran-9b-yl)carbamate (31)

Tert-butyl ((4bR,9bR)-1-amino-7-bromo-4b-hydroxy-10-oxo-4b,10-dihydro-9bH-indeno[1,2-b]benzofuran-9b-yl)carbamate 12 (112 mg, 0.25 mmol) was taken in nitrogen purged Toluene:water (5 mL). To this was added Pd (OAc)$_2$ (6 mg 0.03 mmol), RuPhos (24 mg, 0.05 mmol), K$_3$PO$_4$ (213 mg, 1.0 mmol) and 6-methyl-2-((1R,2R)-2-methylcyclopropyl)-1,3,6,2-dioxazaborocane-4,8-dione 20 (79 mg, 0.38 mmol). The reaction mass was refluxed at 100° C. for 2 h, the reaction was filtered through CELITE bed. The filtrate was evaporated to obtain the crude. The crude was purified with silica gel column chromatography to give product.

(4bR,9bR)-1,9b-Diamino-4b-hydroxy-7-((1R,2R)-2-methylcyclopropyl)-4b,9b-dihydro-10H-indeno[1,2-b]benzofuran-10-one hydrochloride (32)

Tert-butyl ((4bR,9bR)-1-amino-4b-hydroxy-7-((1R,2R)-2-methylcyclopropyl)-10-oxo-4b,10-dihydro-9bH-indeno[1,2-b]benzofuran-9b-yl)carbamate 31 (70 mg, 0.21 mmol) was dissolved in DCM (2 mL). To this was added 4 N HCl in 1,4-dioxane (0.6 mL, 2.1 mmol). The reaction mass was stirred for 12 h at room temperature (30° C.). The solvent was evaporated under vacuum to give the crude product. Crude was used without purification.

N-((4bR,9bR)-1-Amino-4b-hydroxy-7-((1R,2R)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide (33)

3-Methyl-4-(methylsulfonyl)-1H-pyrrole-2-carboxylic acid 30 (48 mg, 0.23 mmol) was taken in DMF (4 mL, 0.05 M). To this was added HATU (111 mg, 0.3 mmol) and DIPEA (0.1 mL, 0.6 mmol) and was stirred for 20 mins and then was added (4bR,9bR)-1,9b-diamino-4b-hydroxy-7-((1R,2R)-2-methylcyclopropyl)-4b,9b-dihydro-10H-indeno[1,2-b]benzofuran-10-one hydrochloride 32 (70 mg, 0.2 mmol) and stirred at 30° C. for 36 hours. The reaction mixture was quenched with water and extracted with ethyl acetate. The organic layer was washed with water and with brine, and organic layer was dried over Na$_2$SO$_4$ and evaporated solvent to get the crude. The crude was purified over silica-gel column chromatography and again purified by ADH chiral column chromatography to give product. $^1$H-NMR (300 MHz, MeOD) δ 0.66-0.72 (m, 1H), 0.78-0.84 (m, 1H), 0.95-1.03 (m, 1H), 1.13 (d, J=6.0 Hz, 3H), 1.49-1.55 (m, 1H), 2.48 (s, 3H), 3.05 (s, 3H), 6.45 (s, 1H), 6.63-6.67 (m, 1H), 6.76 (d, J=8.1 Hz, 1H), 7.02 (d, J=7.2 Hz, 1H), 2.27 (d, J=8.1 Hz, 1H), 7.38 (s, 1H), 7.43-7.49 (m, 1H). LCMS: 508.4 [M+H]$^+$.

Example 2: N-((4bR,9bR)-1-amino-4b-hydroxy-7-((1S,2R)-2-methylcyclopropyl)-10-oxo-4b,10-dihydro-9bH-indeno[1,2-b]benzofuran-9b-yl)-2-(azetidin-1-yl)acetamide

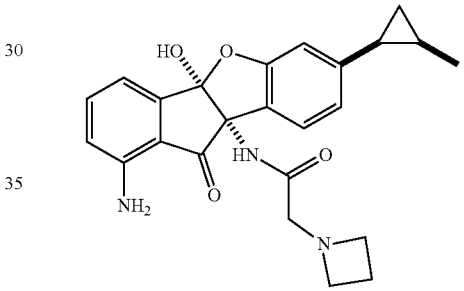

This compound was prepared similar to the compound above. LCMS: 420.2 [M+H]$^+$.

Example 3: N-((4bR,9bR)-1-amino-7-((S)-1-cyclopropylethyl)-4b-hydroxy-10-oxo-4b,10-dihydro-9bH-indeno[1,2-b]benzofuran-9b-yl)-6-hydroxypicolinamide

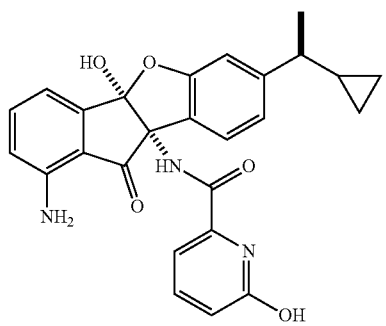 [SMILES: C[C@H](c1ccc2c(c1)O[C@]1(O)c3cccc(N)c3C(=O)[C@]21NC(=O)c1cccc(O)n1)C1CC1]

This compound was prepared similar to Example 1 above. LCMS: 458.2 [M+H]$^+$.

Example 4: N-(1-amino-4b-hydroxy-7-isopropyl-10-oxo-4b,10-dihydro-9bH-indeno[1,2-b]benzofuran-9b-yl)-5-(N-(2-(dimethylamino)ethyl)sulfamoyl)-3,4-dimethyl-1H-pyrrole-2-carboxamide (51)

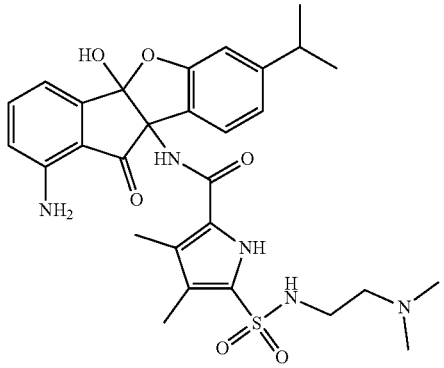 [SMILES: Cc1c(C(=O)NC23C(=O)c4c(N)cccc4C2(O)Oc2cc(C(C)C)ccc23)[nH]c(S(=O)(=O)NCCN(C)C)c1C]

Scheme-5

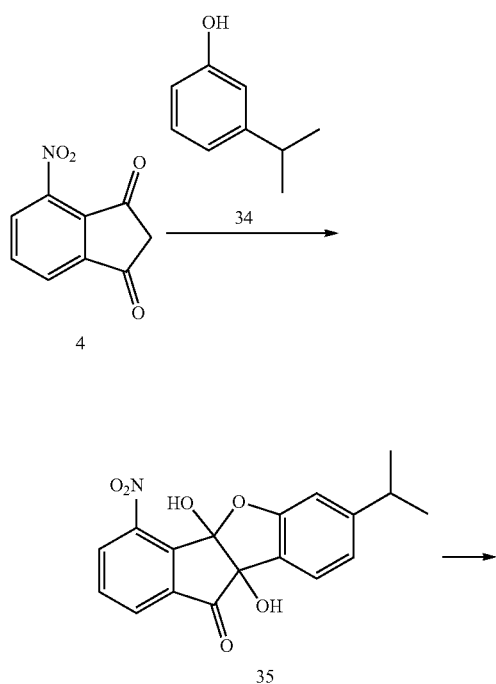

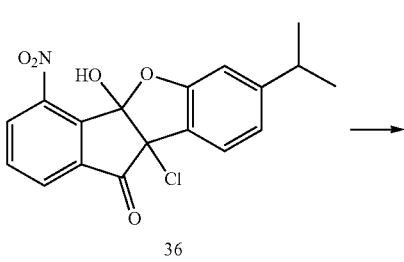

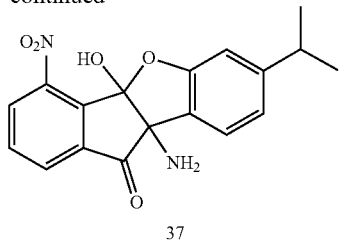

37

4b,9b-Dihydroxy-7-isopropyl-4-nitro-4b,9b-dihydro-10H-indeno[1,2-b]benzofuran-10-one (35)

4-Nitro-1H-indene-1,3(2H)-dione (4) (250 g, 1.31 moles) was taken in 1,4-dioxane (2 liter) and AcOH (200 ml). To this $SeO_2$ (291 g, 2.62 moles) was added at room temperature and kept for reflux at 110° C. for next 4 hours. This was stirred at room temperature for next 12 hours. This was then charged with 500 g-600 g of CELITE. This was stirred and filtered over CELITE pad. The residue was washed with ethyl acetate (300-500 mL). The filtrate obtained was concentrated to get the crude product 5 which was used as such further. 2,2-Dihydroxy-4-nitro-1H-indene-1,3(2H)-dione 5 (crude, 1.31 moles) was taken in glacial AcOH (2 liter) and charged with 3-isopropyl phenol 34 (196 g, 1.44 moles) and kept for reflux for next 10 hours. This was then concentrated and purified over silica gel column chromatography (30% EA in hexanes) to get the pure product.

9b-Chloro-4b-hydroxy-7-isopropyl-4-nitro-4b,9b-dihydro-10H-indeno[1,2-b]benzofuran-10-one (36)

4b,9b-Dihydroxy-7-isopropyl-4-nitro-4b,9b-dihydro-10H-indeno[1,2-b]benzofuran-10-one 35 (50 g, 0.147 moles) was taken in DCM (500 mL) and this suspension was then charged with oxalyl chloride (1.2 eq) in a single lot. This was then slowly charged with DMF (50 mL). The reaction mass was then left to stir at room temperature for next 6 hours. This was quenched with water (500 mL) and the layers were separated. The aqueous layer was extracted with DCM (300 mL×2). The combined organic layer was washed with water (300 mL) and brine (300 mL). This was dried over sodium sulfate and concentrated to get the crude mass which was then purified over short pad of silica (30% ethylacetate in hexanes) to get the pure product. $^1$H-NMR (300 MHz, $CDCl_3$): δ 1.18 (dd, J=3.6 Hz, J=6.9 Hz, 6H), 2.84 (sept, J=6.9 Hz, 1H), 6.34 (s, 1H), 6.70 (s, 1H), 6.94 (dd, J=1.0 Hz, J=7.8 Hz, 1H), 7.45 (d, J=7.8 Hz, 1H), 7.81-7.83 (m, 1H), 8.21 (m, 1H), 8.52 (m, 1H).

9b-Amino-4b-hydroxy-7-isopropyl-4-nitro-4b,9b-dihydro-10H-indeno[1,2-b]benzofuran-10-one (37)

9b-Chloro-4b-hydroxy-7-isopropyl-4-nitro-4b,9b-dihydro-10H-indeno[1,2-b]benzofuran-10-one 36 (36.0 g, 0.1 mole) was taken in THF (350 mL) and cooled to −40° C. To this clear solution 2.0 M solution of $NH_3$ in IPA (100 mL, 0.20 moles) was added using a dropping funnel and temperature was maintained below −20° C. The reaction mass was monitored at −20° C. for an hour and then allowed to warm to room temperature. This was stirred at room temperature until the completion of the reaction and then concentrated completely. The crude was taken in ethylacetate (500 mL) and washed with water (200 mL×2) and brine (100 mL). This was dried over anhyd. Na$_2$SO$_4$ and then concentrated to get the crude mass which was purified over short pad of silica to get the pure product. $^1$H-NMR (300 MHz, CDCl$_3$) δ 1.18 (d, J=6.9 Hz, 6H), 2.84 (sept, J=6.9 Hz, 1H), 3.46 (s, 1H), 6.25 (s, 1H), 6.74 (s, 2H), 6.90 (dd, J=1.2 Hz, J=7.8 Hz, 1H), 7.55 (d, J=7.8 Hz, 1H), 7.77 (t, J=8.1 Hz, 1H), 8.22 (dd, J=1.2 Hz, J=8.4 Hz, 1H), 8.52 (dd, J=1.2 Hz, J=8.1 Hz, 1H).

Scheme-6

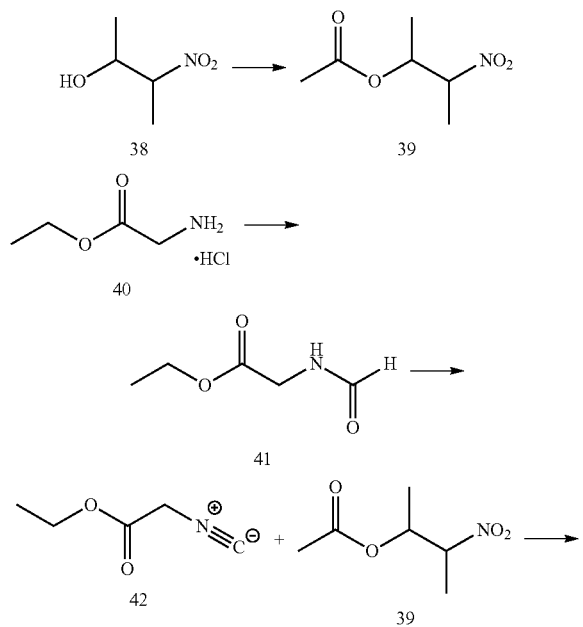

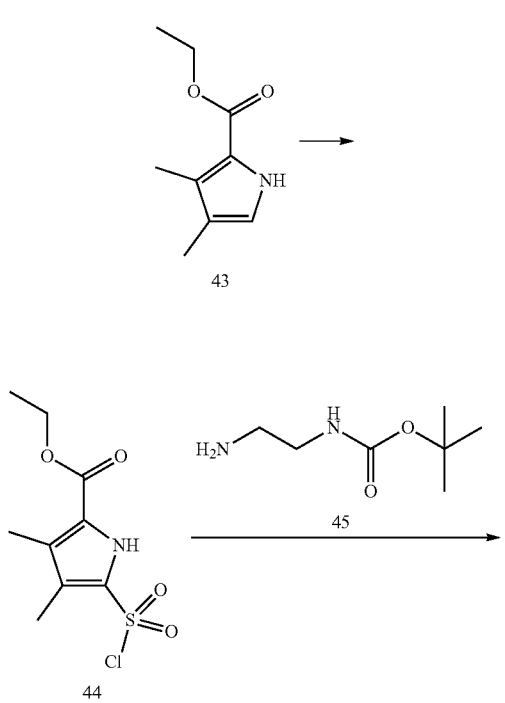

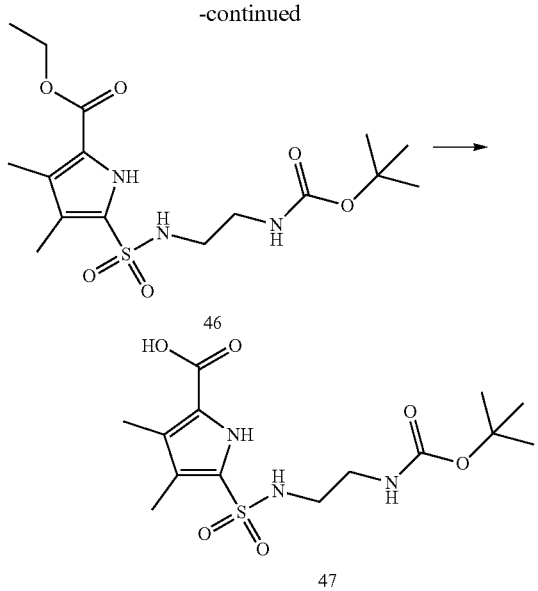

3-Nitrobutan-2-yl acetate (39)

3-Nitrobutan-2-ol 38 (7.5 g, 63 mmol) was taken in DCM (37.5 mL, 1.7 M) and charged with acetic anhydride (11.3 mL, 120 mmol) followed by DMAP (305 mg, 2.52 mmol). After stirring at room temperature (20° C.) for next 24 hours the reaction mass was quenched with MeOH (8 mL) and stirred for next 1 hour. This was then taken in DCM (250 mL) and washed with sat. NaHCO$_3$(100 mL×2), water (100 mL) and brine (~100 mL). This was dried over anhyd. Na$_2$SO$_4$ and concentrated off to get the pure product as an oil.

Ethyl Formylglycinate (41)

To a solution of glycine ester hydrochloride 40 (20.0 g, 0.143 mol) in ethyl formate (90 mL, 1.6 M) was added pTSA (1.36 g, 7.2 mmol). This was brought to reflux and at this temperature TEA (22.0 mL, 0.157 mol) was added dropwise. The reaction mass was refluxed for next 24 hours or as monitored by TLC. This was then cooled down to room temperature (20° C.) and then concentrated off. The crude was then filtered through short pad of silica with 50% EA in hexanes (3000 mL). Later it was concentrated off to get the product which was used as such in next step. The product contained TEA in it by NMR. As next step uses TEA in excess it was taken as such for next step.

Ethyl 2-isocyanoacetate (42)

To a solution of Ethyl formylglycinate 41 (9.40 g, 80 mmol) and TEA (28 mL, 0.2 mol) in DCM (80 mL, 1.0 M) at 0° C. was added POCl$_3$ (7.5 mL, 80 mmol) dropwise slowly. The solution turns red and this was then allowed to attain room temperature after completion of addition and stirred for next 4 hours. The reaction mass was then quenched slowly on Na$_2$CO$_3$ solution and solid Na$_2$CO$_3$ and stirred at room temperature for next 30 mins. The organic layer was separated and aq. layer was extracted with DCM (200 mL×2). The combined organic layers were then washed with water (100 mL) and brine (100 mL). This was dried over anhyd. Na₂SO₄ and concentrated to get the pure product as a liquid.

Ethyl 3,4-dimethyl-1H-pyrrole-2-carboxylate (43)

3-nitrobutan-2-yl acetate 39 (8.9 g, 55.0 mmol) and ethyl 2-isocyanoacetate 42 (8.1 g, 71.5 mmol) was taken in THF:water (1:1, 110 mL, 0.5 M) and to this anhyd. K₂CO₃ (12.2 g, 88.0 mmol) was added slowly in portions with vigorous stirring and the reaction mass was then stirred at room temperature for next 3 days. The reaction mass was then concentrated off to a thick slurry. This was then diluted with ice cold water (100 mL) and then slowly neutralized with 5% HCl (2 N, pH=5) at 0° C. This was then extracted with EA (150 mL×3). The combined organic layer was washed with 5% brine (100 mL×2). Then it was dried over anhy. Na₂SO₄ and concentrated off to get the crude. Crude was purified over silica gel column chromatography (0-10% EA in hexanes) to get the pure product.

Ethyl 5-(chlorosulfonyl)-3,4-dimethyl-1H-pyrrole-2-carboxylate (44)

Ethyl 3,4-dimethyl-1H-pyrrole-2-carboxylate 43 (1.67 g, 10.0 mmol) was taken in CHCl₃ (40 mL, 0.25 M) and to this chlorosulfonic acid (10.0 mL, 150.0 mmol) was added at 0° C. The reaction mass was stirred at 0° C. for next 3 hours. The reaction mass was quenched with crushed ice (120 mL) and extracted with DCM (100 mL×3). The combined organic layers were washed with water (100 mL) and brine (100 mL). This was dried over anhyd. Na₂SO₄ and concentrated off to get the crude product. The crude was passed through short pad of silica gel with DCM and the filtrated was concentrated to get the pure product.

Ethyl 5-(N-(2-((tert-butoxycarbonyl)amino)ethyl)sulfamoyl)-3,4-dimethyl-1H-pyrrole-2-carboxylate (46)

Ethyl 5-(chlorosulfonyl)-3,4-dimethyl-1H-pyrrole-2-carboxylate 44 (530 mg, 2.0 mmol) was taken in DCM (20 mL, 0.1 M) and to this tert-butyl (2-aminoethyl)carbamate 45 (385 mg, 2.4 mmol) followed by addition of DIPEA (0.52 mL, 3.0 mmoL) at room temperature. The reaction mass was then stirred at room temperature (25° C.) for next 2 hours. The reaction mass was quenched with water (50 mL) and then extracted with DCM (70 mL×2). The combined organic layer was washed with water (30 ml) and brine (30 ml). This was dried over anhyd. Na₂SO₄ and concentrated off to get the crude product. Crude product was purified over silica gel column chromatography (30% EA in hexanes) to get the pure product.

S—(N-(2-((tert-butoxycarbonyl)amino)ethyl)sulfamoyl)-3,4-dimethyl-1H-pyrrole-2-carboxylic acid (47)

Ethyl 5-(N-(2-((tert-butoxycarbonyl)amino)ethyl)sulfamoyl)-3,4-dimethyl-1H-pyrrole-2-carboxylate 46 (682 mg, 1.75 mmol) was taken in THF:MeOH:H₂O (1:1:10, 18.0 mL, 0.1 M) and charged with LiOH·H₂O (367 mg, 5.0 mmol) and the reaction was refluxed at 80° C. for 5 hours. The reaction mass was concentrated off to remove the volatiles. This was then acidified with 1 N HCl (pH<2-3). The solid precipitated was then filtered off, washed with cold water and dried to get the pure product.

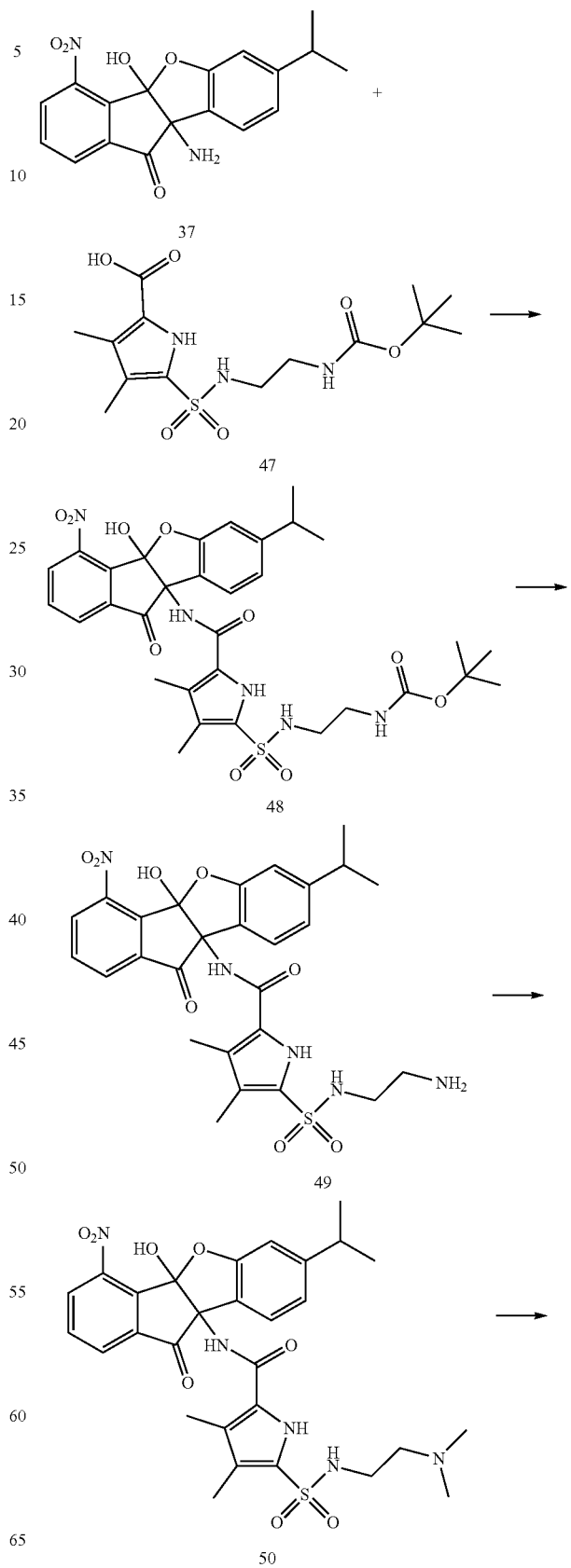

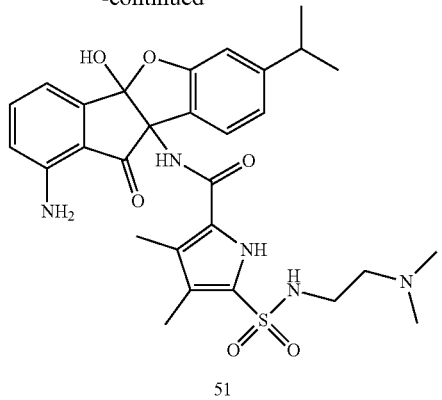

51

Tert-butyl (2-((5-((4b-hydroxy-7-isopropyl-4-nitro-10-oxo-4b,10-dihydro-9bH-indeno[1,2-b]benzofuran-9b-yl)carbamoyl)-3,4-dimethyl-1H-pyrrole)-2-sulfonamido)ethyl)carbamate (48)

5-(N-(2-((tert-butoxycarbonyl)amino)ethyl)sulfamoyl)-3,4-dimethyl-1H-pyrrole-2-carboxylic acid 47 (452 mg, 1.25 mmol) was taken in DMF (5 mL, 0.25 M) and cooled to 0° C. This was charged with EDCI (360 mg, 1.88 mmol) followed by HOBt (254 mg, 1.88 mmol). After 10 mins it was charged with 9b-amino-4b-hydroxy-7-isopropyl-4-nitro-4b,9b-dihydro-10H-indeno[1,2-b]benzofuran-10-one 37 (425 mg, 1.25 mmol) followed by DIPEA (0.55 mL, 3.13 mmol) and allowed to attain room temperature (35° C.) for next 18 hours. The reaction mass was then quenched with water (60 mL) and extracted with EA (100 mL×2). The combined organic layer was washed with water (50 ml) and brine (30 mL). This was dried over anhyd. Na$_2$SO$_4$ and concentrated to get the crude. The crude was purified over silica gel column chromatography (40% EA in hexanes) to get the product.

S—(N-(2-aminoethyl)sulfamoyl)-N-(4b-hydroxy-7-isopropyl-4-nitro-10-oxo-4b,10-dihydro-9bH-indeno[1,2-b]benzofuran-9b-yl)-3,4-dimethyl-1H-pyrrole-2-carboxamide (49)

Tert-butyl (2-((5-((4b-hydroxy-7-isopropyl-4-nitro-10-oxo-4b,10-dihydro-9bH-indeno[1,2-b]benzofuran-9b-yl)carbamoyl)-3,4-dimethyl-1H-pyrrole)-2-sulfonamido)ethyl)carbamate 48 (275 mg, 0.4 mmol) was taken in DCM (8 mL, 0.05 M), and to this 4 M HCl in dioxane (1.0 mL, 4.0 mmol) was added. This was stirred at room temperature (25° C.) for 15 hours. The reaction was diluted with DCM (20 mL) and stirred with sat. NaHCO$_3$ (20 mL) for 10 mins. The free amine was not liberated well and thus 0.5 mL of TEA was added. Then it was diluted with DCM (100 mL) and then layers were separated off. The org, layer was washed with sat. NaHCO$_3$(20 mL), water (30 mL) and brine (30 ml). This was dried over anhyd. Na$_2$SO$_4$ and concentrated off to get a solid.

5-(N-(2-(dimethylamino)ethyl)sulfamoyl)-N-(4b-hydroxy-7-isopropyl-4-nitro-10-oxo-4b,10-dihydro-9bH-indeno[1,2-b]benzofuran-9b-yl)-3,4-dimethyl-1H-pyrrole-2-carboxamide (50)

5-(N-(2-aminoethyl)sulfamoyl)-N-(4b-hydroxy-7-isopropyl-4-nitro-10-oxo-4b,10-dihydro-9bH-indeno[1,2-b]benzofuran-9b-yl)-3,4-dimethyl-1H-pyrrole-2-carboxamide 49 (88 mg, 0.15 mmol) was taken in MeCN: gl. AcOH (2:1, 3 mL, 0.05 M) cooled to 0° C. This was charged with 35% HCHO aq. solution (0.125 mL, 1.5 mmol) followed by addition of NaBH$_3$CN (33 mg, 0.53 mmol). This was stirred at 0° C. for next 0.5 hour. The reaction mass was quenched with water (40 mL) and extracted with EA (40 mL×2). The combined organic layers were washed with water (30 mL) and brine (10 mL). This was dried over anhyd. Na$_2$SO$_4$ and concentrated off to get the crude. Crude was purified over column chromatography (0.05% TEA in 0-10% MeOH in DCM) to get the pure product.

N-(1-amino-4b-hydroxy-7-isopropyl-10-oxo-4b,10-dihydro-9bH-indeno[1,2-b]benzofuran-9b-yl)-5-(N-(2-(dimethylamino)ethyl)sulfamoyl)-3,4-dimethyl-1H-pyrrole-2-carboxamide (51)

5-(N-(2-aminoethyl)sulfamoyl)-N-(4b-hydroxy-7-isopropyl-4-nitro-10-oxo-4b,10-dihydro-9bH-indeno[1,2-b]benzofuran-9b-yl)-3,4-dimethyl-1H-pyrrole-2-carboxamide 50 (46 mg, 0.075 mmol) was taken in EtOH:water (10:1, 5.0 mL, 0.015 M), and to this iron powder (13 mg, 0.23 mmol) was charged followed by 1 M HCl (3 drops). This was refluxed at 90° C. for next 1.5 hours. The reaction mass was cooled to 50° C. and then it was neutralized with TEA (1 drop). The reaction mixture was then filtered over CELITE under hot conditions using EA (20 mL). The filtrate was concentrated off and taken in EA (100 mL) and washed with water (20 mL) and brine (20 mL). This was dried over anhyd. Na$_2$SO$_4$ and concentrated to get crude. Crude was purified over thin layer preparative chromatography (10% MeOH in DCM) to get the pure product. $^1$H-NMR (300 MHz, CD$_3$OD) δ 1.19 (d, J=6.9 Hz, 6H), 2.17 (s, 3H), 2.20 (s, 3H), 2.43 (s, 6H), 2.65 (t, J=6.6 Hz, 2H), 2.82 (sept, J=6.9 Hz, 1H), 3.06 (t, J=6.6 Hz, 2H), 6.69 (s, 1H), 6.77 (d, J=7.8 Hz, 1H), 6.85 (d, J=7.8 Hz, 1H), 7.03 (d, J=7.2 Hz, 1H), 7.36 (d, J=7.8 Hz, 1H), 7.45-7.50 (m, 1H). LCMS: 582.3 [M+H]$^+$.

Example 5: N-((4bR,9bR)-1-amino-7-((S)-1-cyclopropylethyl)-4b-hydroxy-10-oxo-4b,10-dihydro-9bH-indeno[1,2-b]benzofuran-9b-yl)-2-(azetidin-1-yl)acetamide (62)

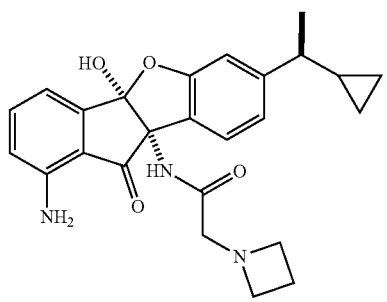 [SMILES: C[C@H](c1ccc2c(c1)O[C@]1(O)c3cccc(N)c3C(=O)[C@]21NC(=O)CN1CCC1)C1CC1]

Scheme-8

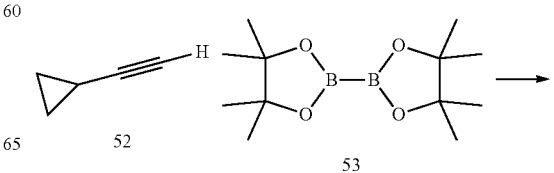

2-(1-Cyclopropylvinyl)-4,4,5,5-tetramethyl-1,3,2-dioxaborolane (54)

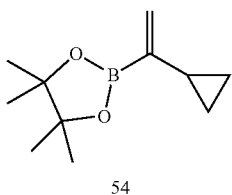

To a reaction flask was added anhydrous lithium chloride (7.06 g, 166.5 mmol), CuCl (16.5 g, 166.5 mmol) and dried N, N-dimethylformamide (500 mL) under nitrogen, and the mixture was stirred at room temperature for 1 h, then was added potassium acetate (16.4 g, 166.5 mmol), $B_2Pin_2$ 53 (42.3 g, 166.5 mmol) and cyclopropylacetylene 52 (10 g, 151.3 mmol) successively and stirring was continued at room temperature for 20 h. Reaction mass was quenched with sat. solution of $NH_4Cl$ (100 mL) was added with ethyl acetate (100 mL) and was filtered through CELITE bed. The filtrate was extracted with Hexane (200 mL×3) and the combined organic layer was collected and washed with water (100 mL×3) and with brine (100 mL) dried over $Na_2SO_4$ evaporated solvent under vacuum to get crude. The crude was purified over silica gel column chromatography (Hexane) to give product as an oil.

Scheme-9

Tert-butyl 2-(azetidin-1-yl)acetate (57)

Azetidine hydrochloride 56 (73 g, 78 mmol) was taken in THF:water (4:1, 170 mL, 0.3 M) and cooled to 0° C. To this was added aq. 2N NaOH (78 mL, 157 mmol) and stirred for 10 mins. This was then charged with tert-butyl 2-bromoacetate 55 (7.2 mL, 49 mmol) at 0° C. dropwise and allowed to stir at 30° C. for next 1 hour. The reaction mixture was then extracted with EA (150 mL×2) and the combined org. layers was washed with sat. brine (~50 mL). This was dried over anhyd. $Na_2SO_4$ and concentrated off to get the crude product as a liquid.

2-(Azetidin-1-yl)acetic acid hydrochloride (58)

Tert-butyl 2-(azetidin-1-yl)acetate 57 (6.7 g, 39 mmol) was cooled to 0° C. and charged slowly with 4 M HCl in dioxane (98 mL, 0.4 M). The reaction mixture was then stirred at room temperature (30° C.) for next 24 hours. The solid precipitated was then filtered off, washed with cold 1,4 dioxane (~20-30 mL) and dried to get the pure product.

Scheme-10

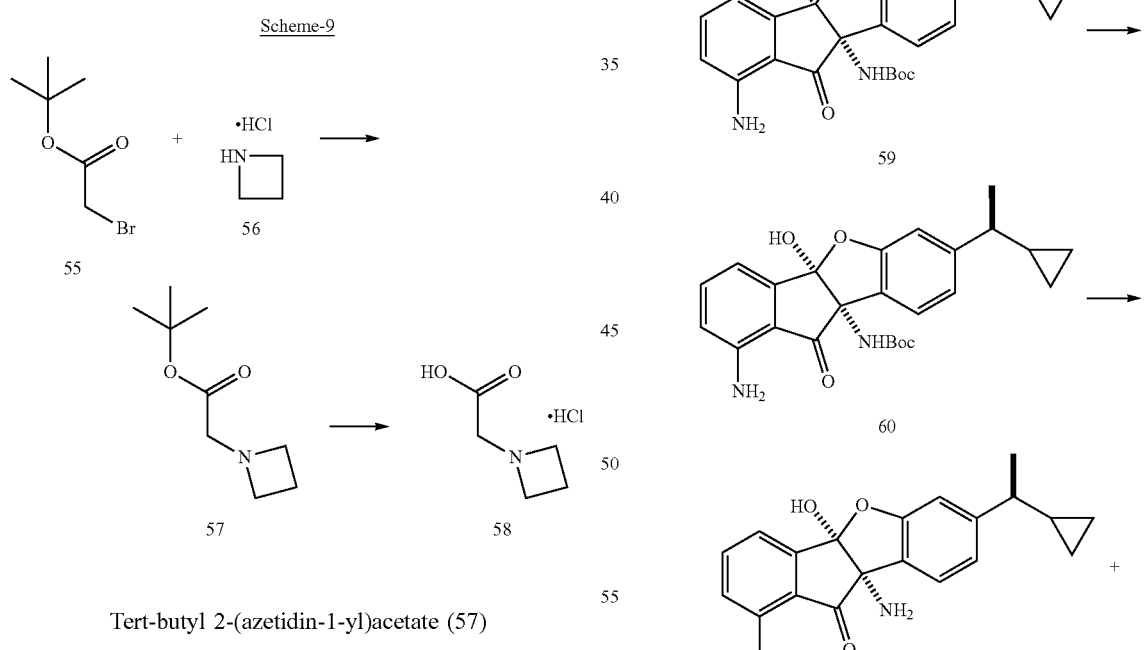

-continued

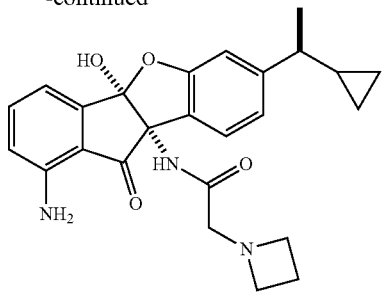

62

Tert-butyl ((4bR,9bR)-1-amino-7-(1-cyclopropylvinyl)-4b-hydroxy-10-oxo-4b,10-dihydro-9bH-indeno[1,2-b]benzofuran-9b-yl)carbamate (59)

Tert-butyl (1-amino-7-bromo-4b-hydroxy-10-oxo-4b,10-dihydro-9bH-indeno[1,2-b]benzofuran-9b-yl)carbamate 12 (3.36 g, 7.50 mmol), Pd(dppf)Cl$_2$ (613 mg, 0.75 mmol) and K$_2$CO$_3$ (3.11 g, 22.5 mmol) was taken in a sealed tube and charged with toluene:water (5:1, 75 mL, 0.10 M) which were already purged with Nitrogen. The reaction mixture was again purged with N2 (10 mins) and then charged with 2-(1-cyclopropylvinyl)-4,4,5,5-tetramethyl-1,3,2-dioxaborolane 54 (2.15 g, 11.3 mmol) and kept at 90° C. for next 3 hours. The reaction mixture was passed through CELITE bed and concentrated off. This was taken in EA and water and the layers were separated off. The org. layers were dried over anhyd. Na$_2$SO$_4$ and concentrate off to get the crude. The crude was purified over silica gel column chromatography (20-30% EA in Hexanes) to get the pure product.

Tert-butyl ((4bR,9bR)-1-amino-7-((S)-1-cyclopropylethyl)-4b-hydroxy-10-oxo-4b,10-dihydro-9bH-indeno[1,2-b]benzofuran-9b-yl)carbamate (60)

Tert-butyl (1-amino-7-(1-cyclopropylvinyl)-4b-hydroxy-10-oxo-4b,10-dihydro-9bH-indeno[1,2-b]benzofuran-9b-yl)carbamate 59 (5.43 g, 12.5 mmol) was taken in DCM (125 mL, 0.10 M) and charged [((4S,5 S)-Cy2-UBaphox)Ir(COD)]BARF (433 mg, 0.25 mmol) under nitrogen. This was then flushed with H$_2$ gas and then kept under H$_2$ atmosphere (60 psi) for next 4 hour at rt (20° C.). The reaction mass was then concentrated off to get the crude. The crude was purified over silica gel column chromatography (0-10-30% EA in Hexanes with 10% of DCM as cosolvent) to get the pure product.

(4bR,9bR)-1,9b-Diamino-7-((S)-1-cyclopropylethyl)-4b-hydroxy-4b,9b-dihydro-OH-indeno[1,2-b]benzofuran-10-one (61)

Tert-butyl ((4bR,9bR)-1-amino-7-((S)-1-cyclopropylethyl)-4b-hydroxy-10-oxo-4b,10-dihydro-9bH-indeno[1,2-b]benzofuran-9b-yl)carbamate 60 (2.18 g, 5.00 mmol) was taken in DCM (50 mL, 0.1 M) and immediately charged with 4.0 M HCl in dioxane (12.5 mL, 50.0 mmol). The reaction mixture was then stirred at r.t. (20° C.) for next 6 hours. The reaction mixture was diluted with EA (~150 mL) and stirred with sat. NaHCO$_3$(~100 mL) for 5-10 mins. The layers were separated off and aq. layer was extracted with EA (~100 mL). The combined org. layer was washed with water (100 ml) and brine (~100 mL). This was dried over anhyd. Na$_2$SO$_4$ and concentrated off to get the product, which was used as such in next step without further purifications.

N-((4bR,9bR)-1-Amino-7-((S)-1-cyclopropylethyl)-4b-hydroxy-10-oxo-4b,10-dihydro-9bH-indeno[1,2-b]benzofuran-9b-yl)-2-(azetidin-1-yl)acetamide (62)

2-(Azetidin-1-yl)acetic acid hydrochloride 58 (1.02 g, 6.75 mmol) in 45 mL anhydrous DMF (0.1 M) was charged with HATU (2.57 g, 6.75 mmol) and DIPEA (2.35 mL, 13.5 mmol) at 0° C. After 10 mins this was charged with (4bR,9bR)-1,9b-diamino-7-((S)-1-cyclopropylethyl)-4b-hydroxy-4b,9b-dihydro-10H-indeno[1,2-b]benzofuran-10-one 61 (1.51 g, 4.50 mmol) and stirred at r.t. (20° C.) for 15 h. The reaction mass was quenched with water (~100 mL) and sat. NaHCO$_3$(~100 mL). This was extracted with EA (100 mL×3). The combined organic layers were washed with water (100 mL×2), brine (100 mL) and dried over anhyd. Na$_2$SO$_4$ and concentrated off to get the crude. Crude was purified over silica gel column chromatography (0-10% MeOH in DCM) to get the pure product. $^1$H-NMR (500 MHz, MeOD) δ 7.50-7.39 (m, 1H), 7.29 (d, J=8.0 Hz, 1H), 6.99 (d, J=7.3 Hz, 1H), 6.85 (dd, J=8.0, 1.3 Hz, 1H), 6.72 (d, J=8.5 Hz, 1H), 6.69 (d, J=1.3 Hz, 1H), 3.37 (t, J=7.3 Hz, 4H), 3.18 (s, 2H), 2.09 (p, J=7.1 Hz, 2H), 1.91-1.83 (m, 1H), 1.25 (d, J=7.0 Hz, 3H), 0.94-0.79 (m, 1H), 0.55-0.47 (m, 1H), 0.40-0.26 (m, 1H), 0.17-0.13 (m, 1H), 0.07-0.03 (m, 1H). LCMS: 432.3 [M−H]$^-$. LCMS: 434.2 [M+H]$^+$.

Example 6: N-(1-amino-7-((1R,2S)-1,2-dimethylcyclopropyl)-4b-hydroxy-10-oxo-4b,10-dihydro-9bH-indeno[1,2-b]benzofuran-9b-yl)-3-methyl-4-(methylsulfonyl)-1H-pyrrole-2-carboxamide

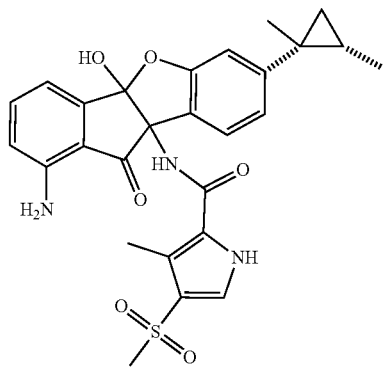 [SMILES: Cc1c(S(C)(=O)=O)c[nH]c1C(=O)NC12C(=O)c3c(N)cccc3C1(O)Oc1cc([C@]3(C)C[C@@H]3C)ccc12]

This compound was prepared similar to Example 5 above. LCMS: 522.2 [M+H]$^+$.

Example 7: N-(1-amino-4b-hydroxy-7-(2-methylcyclobutyl)-10-oxo-4b,10-dihydro-9bH-indeno[1,2-b]benzofuran-9b-yl)-3-methyl-4-(methylsulfonyl)-1H-pyrrole-2-carboxamide

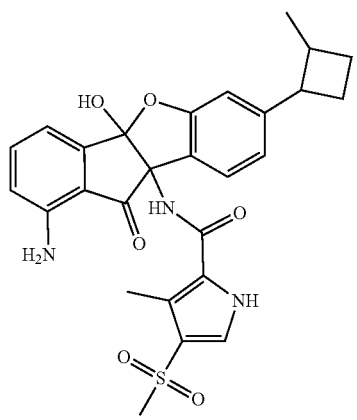 [SMILES: Cc1c(S(C)(=O)=O)c[nH]c1C(=O)NC12C(=O)c3c(N)cccc3C1(O)Oc1cc(C3CCC3C)ccc12]

This compound was prepared similar to Example 5 above. LCMS: 522.2 [M+H]⁺.

Example 8: N-((4bR,9bR)-1-amino-7-((R)-1-cyclopropylethyl)-4b-hydroxy-10-oxo-4b,10-dihydro-9bH-indeno[1,2-b]benzofuran-9b-yl)-6-hydroxypicolinamide

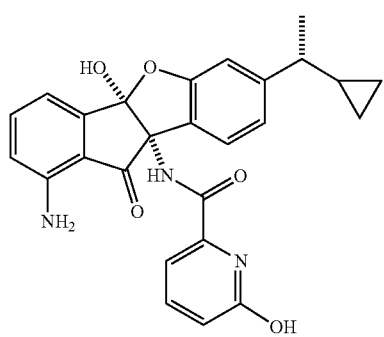 [SMILES: C[C@@H](c1ccc2c(c1)O[C@]1(O)c3cccc(N)c3C(=O)[C@]21NC(=O)c1cccc(O)n1)C1CC1]

This compound was prepared similar to Example 5 above. LCMS: 458.1 [M+H]⁺.

Example 9: N-(1-Amino-4b-hydroxy-7-((trans)-2-methylcyclopropyl)-10-oxo-4b,10-dihydro-9bH-indeno[1,2-b]benzofuran-9b-yl)-3-methyl-S-((4-methylpiperazin-1-yl)sulfonyl)-1H-pyrrole-2-carboxamide (83)

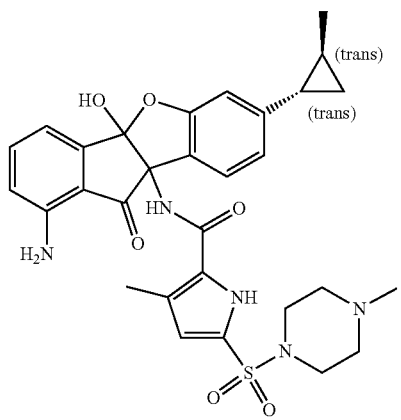 [SMILES: Cc1cc(S(=O)(=O)N2CCN(C)CC2)[nH]c1C(=O)NC12C(=O)c3c(N)cccc3C1(O)Oc1cc([C@H]3C[C@@H]3C)ccc12]

Scheme-11

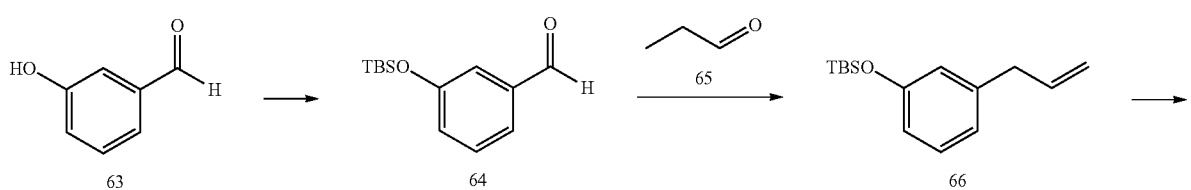

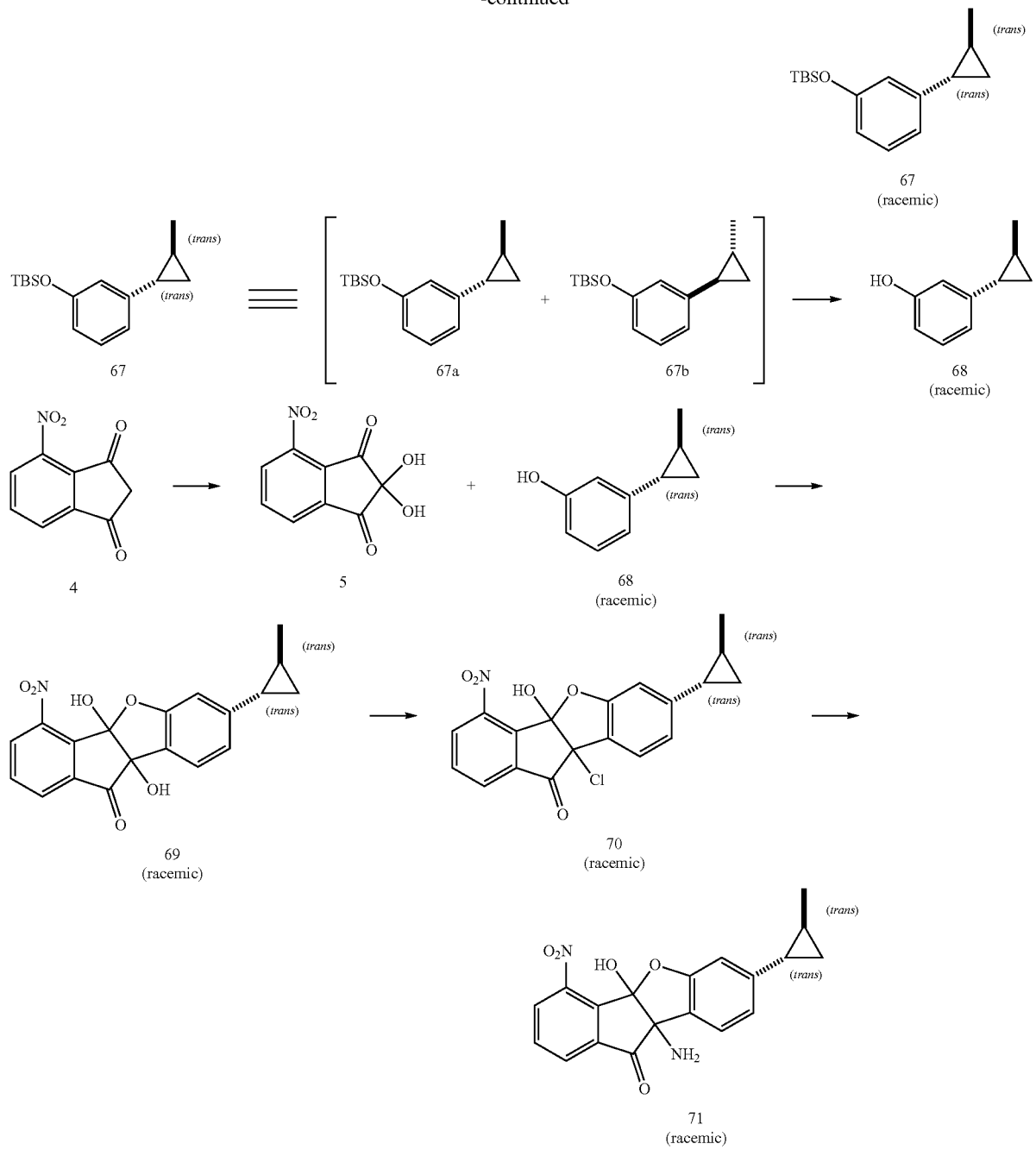

3-((Tert-butyldimethylsilyl)oxy)benzaldehyde (64)

To a solution of 3-hydroxy benzaldehyde (30 g, 0.25 mol) and imidazole (21.7 g, 0.32 mol) in dried dichloromethane (250 mL) was added tert-butylchlorodimethylsilane (44.4 g, 0.30 mol) slowly at 0 TC. The reaction mixture was stirred overnight at room temperature. The reaction mixture was filtered and washed with DCM. The organic layer was washed with water, dried over anhydrous MgSO$_4$, filtered and concentrated. The residue was purified on a silica gel column, eluted with EA/Hexane (0/100→1/10) to afford of desired product. $^1$H NMR (300 MHz, CDCl$_3$) δ 9.95 (s, 1H), 7.40 (tdd, J=21.4, 12.8, 9.5 Hz, 3H), 7.11 (ddd, J=7.9, 2.5, 1.2 Hz, 1H), 1.00 (s, 9H), 0.23 (d, J=3.0 Hz, 6H).

(E)-Tert-butyldimethyl(3-(prop-1-en-1-yl)phenoxy) silane (66)

To a solution of 3-((tert-butyldimethylsilyl)oxy)benzaldehyde 64 (30 g, 0.13 mol), propion aldehyde 65 (11.5 mL, 0.16 mol), and malononitrile (20.95 g, 0.17 mol) in acetonitrile (630 mL, 0.2 M) was added acetic acid (13.7 mL, 0.24 mol) dropwise at room temperature. The reaction mixture was stirred for 10 min then ammonium acetate (12.2 g, 0.16 mol) was added. The resulting solution was stirred overnight at 80° C. The reaction mixture was cooled down to room temperature, diluted with ethyl acetate, filtered, concentrated and purified on a silica gel column, eluted with n-Hex to afford of desired product. ¹H NMR (300 MHz, CDCl₃) δ 7.14 (td, J=7.8, 2.8 Hz, 1H), 6.92 (d, J=7.5 Hz, 1H), 6.81 (s, 1H), 6.68 (d, J=8.0 Hz, 1H), 6.35 (d, J=15.9 Hz, 1H), 6.22 (m, 1H), 1.88 (d, J=6.1 Hz, 3H), 0.99 (d, J=2.6 Hz, 9H), 0.20 (d, J=2.6 Hz, 6H).

Tert-butyldimethyl(3-((trans)-2-methylcyclopropyl) phenoxy)silane (67)

To a dried dichloromethane (150 mL) was added diethylzinc (50 mL, 1.0 M in hexane, 0.05 mol) dropwise by cannular with stirring at −40° C. After 10 min, to this reaction mixture was added a solution of diiodomethane (8 mL, 0.1 mol) in dried dichloromethane (25 mL) dropwise at −40° C. The reaction mixture was stirred for 1 h at −40° C. To this reaction mixture was added a solution of trichloroacetic acid (0.82 g, 0.005 mol), DME (2.59 mL, 0.025 mol) in dried dichloromethane (25 mL) dropwise at −40° C. The reaction mixture was stirred for 1 h at −15° C. To this reaction mixture was added a solution of (E)-tert-butyldimethyl(3-(prop-1-en-1-yl)phenoxy)silane 66 (6.21 g, 0.025 mol) in dried dichloromethane (25 mL) dropwise at −15° C. After 10 min, the reaction mixture was warmed to room temperature and stirred overnight at room temperature. The reaction mixture was poured carefully to ice-water at 0° C. The generated solid was filtered out and the filtrate was extracted with dichloromethane, dried over MgSO₄, concentrated and purified on a silica gel column, eluted with n-Hex/EA (100/0→50/1) to the desired racemic product in trans geometry as a oil. ¹H NMR (300 MHz, CDCl₃) δ 7.08 (t, J=7.8 Hz, 1H), 6.60 (m, 2H), 6.48 (t, J=2.0 Hz, 1H), 1.87 (dd, J=6.4, 1.3 Hz, 0.20H), 1.51 (dt, J=8.9, 3.3 Hz, 1H), 1.19 (dd, J=15.5, 5.8 Hz, 3H), 1.01 (m, 9H), 0.81 (m, 2H), 0.71 (m, 1H), 0.18 (m, 6H).

3-((Trans)-2-methylcyclopropyl)phenol (68)

To a solution of racemic tert-butyldimethyl(3-((trans)-2-methylcyclopropyl)phenoxy)silane 67 (32.93 g, 0.12545 mol) in ethanol (300 mL) was added conc-HCl (30 mL) dropwise with stirring. The reaction mixture was stirred overnight at room temperature. The reaction mixture was concentrated and purified on a silica gel column, and eluted with EA/Hex (1/20→1/15) to afford of 3-((1S,2S)-2-methylcyclopropyl)phenol (product). ¹H NMR (300 MHz, CDCl₃) δ 7.10 (t, J=7.9 Hz, 1H), 6.59 (m, 2H), 6.49 (m, 1H), 4.66 (d, J=8.7 Hz, 1H), 1.52 (dt, J=8.9, 4.6 Hz, 1H), 1.15 (t, J=10.4 Hz, 3H), 1.04 (tdd, J=10.3, 5.7, 4.5 Hz, 1H), 0.86 (m, 1H), 0.72 (m, 1H).

4b,9b-Dihydroxy-7-((trans)-2-methylcyclopropyl)-4-nitro-4b,9b-dihydro-10H-indeno[1,2-b]benzofuran-10-one (69)

To a solution of 4-nitro-1H-indene-1,3(2H)-dione 4 (16.4 g, 0.086 mol) in dioxane: AcOH (10:1, v/v, 140 mL/14 mL, 0.6 M) was added selenium dioxide (19 g, 0.17 mol). The reaction mixture was refluxed for 3 hours at 130° C. The reaction mixture was cooled down to room temperature and diluted with ethyl acetate, filtered through the CELITE pad, concentrated to get the crude product 5, which was used in the next step without purification. To a solution of 2,2-dihydroxy-4-nitro-1H-indene-1,3(2H)-dione 5 (crude) in gl. acetic acid (140 mL) was added racemic mixture of 3-((trans)-2-methylcyclopropyl)phenol (12.7 g, 0.085 mol).

The reaction mixture was refluxed for 3 hours at 80° C., cooled down to room temperature, diluted with EA, filtered and concentrated. The residue was purified on a silica gel column, eluted with EA/hexane (1/2→2/3) to afford of desired product. ¹H NMR (300 MHz, CDCl₃) δ 8.48 (dd, J=8.0, 0.9 Hz, 1H), 8.16 (dd, J=7.6, 1.0 Hz, 1H), 7.77 (t, J=7.8 Hz, 1H), 7.40 (d, J=7.9 Hz, 1H), 6.72 (ddd, J=7.9, 3.9, 1.4 Hz, 1H), 6.45 (m, 1H), 1.50 (m, 1H), 1.12 (m, 3H), 0.98 (m, 1H), 0.81 (dt, J=14.8, 5.5 Hz, 1H), 0.75 (m, 1H).

9b-Chloro-4b-hydroxy-7-((trans)-2-methylcyclopropyl)-4-nitro-4b,9b-dihydro-JOH-indeno[1,2-b]benzofuran-10-one (70)

To a solution of racemic 4b,9b-Dihydroxy-7-((trans)-2-methylcyclopropyl)-4-nitro-4b,9b-dihydro-10H-indeno[1,2-b]benzofuran-10-one 69 (10.1 g, 0.03 mol) in dried dichloromethane (143 mL) was added oxalyl chloride (2.90 mL, 0.03 mol) dropwise at room temperature. To the reaction mixture was added dried DMF (10 mL) dropwise with stirring at room temperature (~2 hours). The reaction mixture was stirred for 3 hours at room temperature. The reaction mixture was diluted with dichloromethane, washed with water, the organic layer was dried over MgSO₄, filtered, concentrated and purified on a silica gel column, eluted with EA/Hex (1/4→1/2) to afford of desired product. ¹H NMR (300 MHz, CDCl₃) δ 8.49 (dd, J=8.0, 1.1 Hz, 1H), 8.19 (dd, J=7.7, 1.1 Hz, 1H), 7.80 (t, J=7.9 Hz, 1H), 7.38 (d, J=8.0 Hz, 1H), 6.75 (dt, J=8.1, 1.6 Hz, 1H), 6.44 (t, J=1.4 Hz, 1H), 6.29 (s, 1H), 1.50 (m, 1H), 1.13 (dd, J=5.7, 1.2 Hz, 3H), 0.99 (m, 1H), 0.82 (dt, J=12.4, 4.4 Hz, 1H), 0.76 (m, 1H).

9b-Amino-4b-hydroxy-7-((trans)-2-methylcyclopropyl)-4-nitro-4b,9b-dihydro-10H-indeno[1,2-b]benzofuran-10-one (71)

To a solution of racemic 9b-chloro-4b-hydroxy-7-((trans)-2-methylcyclopropyl)-4-nitro-4b,9b-dihydro-10H-indeno[1,2-b]benzofuran-10-one (6.47 g, 0.017 mol) in dried THF (90 mL) was added ammonia solution (26.1 mL, 0.052 mol, 2.0 M in IPA) dropwise (~10 min) at −40° C. The reaction mixture was stirred for 1 hour at −40° C., 1 hour at −20° C. The reaction mixture was diluted with ethyl acetate and washed with brine and water. The organic layer was dried over MgSO₄, filtered, concentrated and purified on a silica gel column, eluted with EA/Hex (1/2→2/3) to afford of desired product. ¹H NMR (300 MHz, CDCl₃) δ 8.48 (m, 1H), 8.10 (d, J=7.6 Hz, 1H), 7.73 (dd, J=13.5, 5.6 Hz, 1H), 7.27 (d, J=7.4 Hz, 1H), 6.68 (m, 1H), 6.45 (d, J=2.7 Hz, 1H), 1.48 (d, J=5.1 Hz, 1H), 1.13 (t, J=5.0 Hz, 3H), 0.98 (d, J=6.7 Hz, 1H), 0.81 (dd, J=5.0, 1.9 Hz, 1H), 0.73 (dd, J=7.3, 4.9 Hz, 1H).

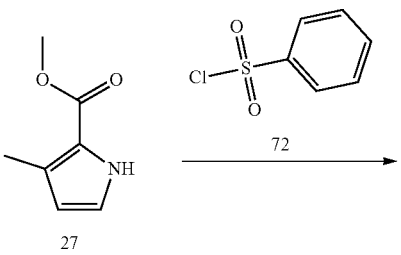

Scheme-12

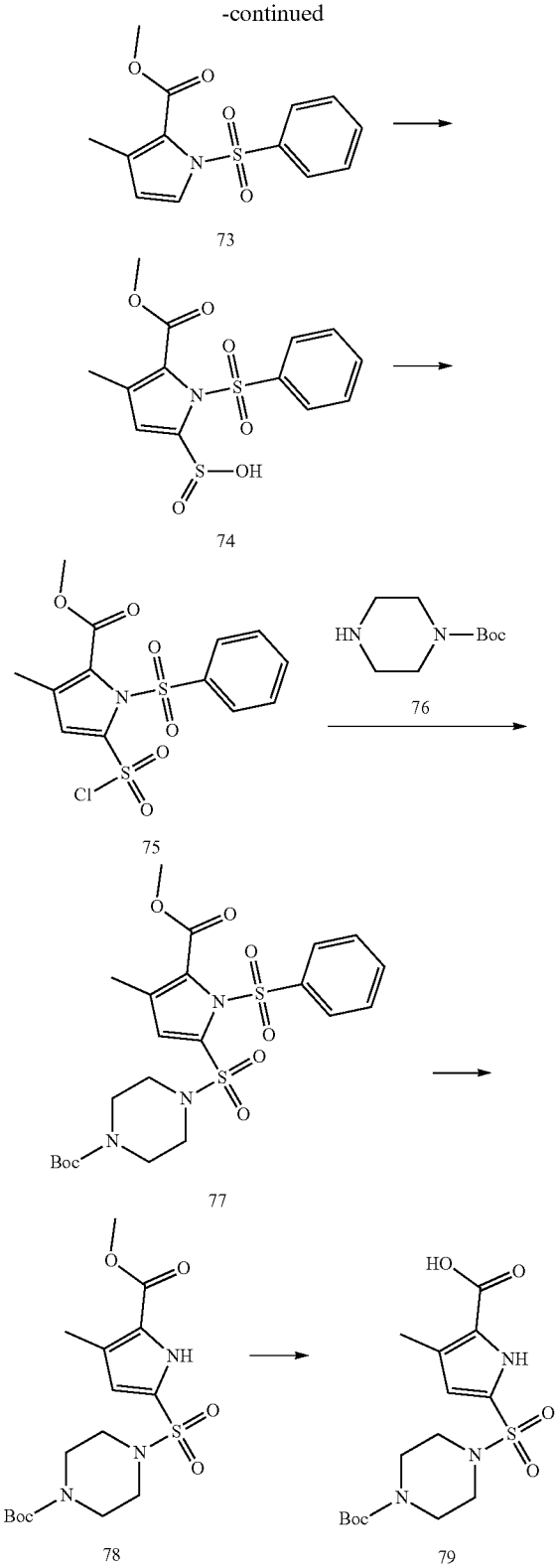

Methyl 3-methyl-1-(phenylsulfonyl)-1H-pyrrole-2-carboxylate (73)

To a solution of methyl 3-methyl-1H-pyrrole-2-carboxylate 27 (3.5 g, 25.2 mmol) in dry DMF (63 mL) was added NaH (1.51 g, 37.8 mmol) at 0° C. followed by addition of benzenesulfonyl chloride 72 (4.82 mL, 37.8 mmol). The reaction mixture was stirred at 0° C. to rt for 15 h. The reaction was quenched with ice water (300 mL), aqueous layer was extracted with ethyl acetate (3×100 mL), the combined organic layer was dried over $Na_2SO_4$ and evaporated under vacuum. Crude was purified over silica-gel column chromatography (ethyl acetate: hexane), and the product obtained was recrystallized using DCM and HX.

5-(Methoxycarbonyl)-4-methyl-1-(phenylsulfonyl)-1H-pyrrole-2-sulfinic acid (74)

Methyl 3-methyl-1-(phenylsulfonyl)-1H-pyrrole-2-carboxylate 73 (5.03 g, 18 mmol) was dissolved in THF (180 mL). The resulting solution was cooled to −78° C., and lithium diisopropyl amide (18 mL, 36 mmol) was added dropwise at −78° C. and reaction mass was stirred at −78° C. for next 1 h. To the cold solution sulfur dioxide (gas) was bubbled slowly for 30 min at −78° C. The resulting reaction mass was warmed to rt slowly and stirred at rt for 12 h. THF was removed under vacuum, the residue obtained was dissolved in water and washed with ethyl acetate (50 mL×2). The aqueous layer was acidified to pH ~1 using 1N HCl, the aqueous layer was extracted with ethyl acetate (200 mL×3) the combined organic layer was washed with water and brine solution, organic layer was dried over $Na_2SO_4$ and evaporated solvent to give the product, which was used as such for the next step without purification.

Methyl 5-(chlorosulfonyl)-3-methyl-1-(phenylsulfonyl)-1H-pyrrole-2-carboxylate (75)

5-(Methoxycarbonyl)-4-methyl-1-(phenylsulfonyl)-1H-pyrrole-2-sulfinic acid 74 (3.9 g, 11.4 mmol) was taken in THF (115 mL) and was cooled to 0° C. To this was added NCS (1.83 g, 13.7 mmol). The reaction mass was stirred at rt for 15 h. THF was removed under vacuum to get residue. The residue was purified over silica gel column chromatography (ethyl acetate: hexane) to give the product.

Tert-butyl 4-((5-(methoxycarbonyl)-4-methyl-1-(phenylsulfonyl)-1H-pyrrol-2-yl)sulfonyl)piperazine-1-carboxylate (77)

Methyl 5-(chlorosulfonyl)-3-methyl-1-(phenylsulfonyl)-1H-pyrrole-2-carboxylate 75 (491.2 mg, 1.3 mmol) was dissolved in DCM (13 mL). To this was added tert-butyl piperazine-1-carboxylate 76 (290.6 mg, 1.56 mmol), followed by addition of DIPEA (0.340 mL, 1.95 mmol). The reaction mass was stirred at rt for 12 h. The reaction mass was diluted with DCM (100 mL) and was washed with water (50 mL×3) and dried over $Na_2SO_4$ evaporated solvent to get crude. The crude was purified over silica gel column chromatography (ethyl acetate: hexane) to give the product.

Tert-butyl 4-((5-(methoxycarbonyl)-4-methyl-1H-pyrrol-2-yl)sulfonyl)piperazine-1-carboxylate (78)

Tert-butyl 4-((5-(methoxycarbonyl)-4-methyl-1-(phenylsulfonyl)-1H-pyrrol-2-yl) sulfonyl)piperazine-1-carboxylate 77 (660 mg, 1.25 mmol) was dissolved in MeOH: $H_2O$ (13 mL). To this solution was added $K_2CO_3$ (518.3 mg, 3.75 mmol). The reaction mass was stirred at 50° C. for 12 h. Methanol was evaporated, and the residue obtained was dissolved in in water (100 mL). The aqueous layer was extracted with ethyl acetate (100 mL×3) and the combined organic layer was washed with water and with brine solution. Organic layer was dried over Na₂SO₄ and the solvent was evaporated to obtain the crude product. The crude product was purified over silica gel column chromatography (ethyl acetate: hexane) to give the product.

5-((4-(Tert-butoxycarbonyl)piperazin-1-yl)sulfonyl)-3-methyl-1H-pyrrole-2-carboxylic acid (79)

Tert-butyl 4-((5-(methoxycarbonyl)-4-methyl-1H-pyrrol-2-yl)sulfonyl)piperazine-1-carboxylate 78 (360 mg, 0.93 mmol) was taken in MeOH:H₂O(1:10) (10 mL) and to this was added LiOH·H₂O (195 mg, 4.65 mmol). The reaction mass was heated at 70° C. for 8 h. MeOH was removed under vacuum and aqueous layer was diluted with water (10 mL) and acidified to pH ~1 with 1N HCl. The product was extracted with ethyl acetate (100 mL×3). The combined organic layer was washed with water and with brine solution, dried over Na₂SO₄, and the solvent was evaporated to give the product (79), which was used as such for next step without purification.

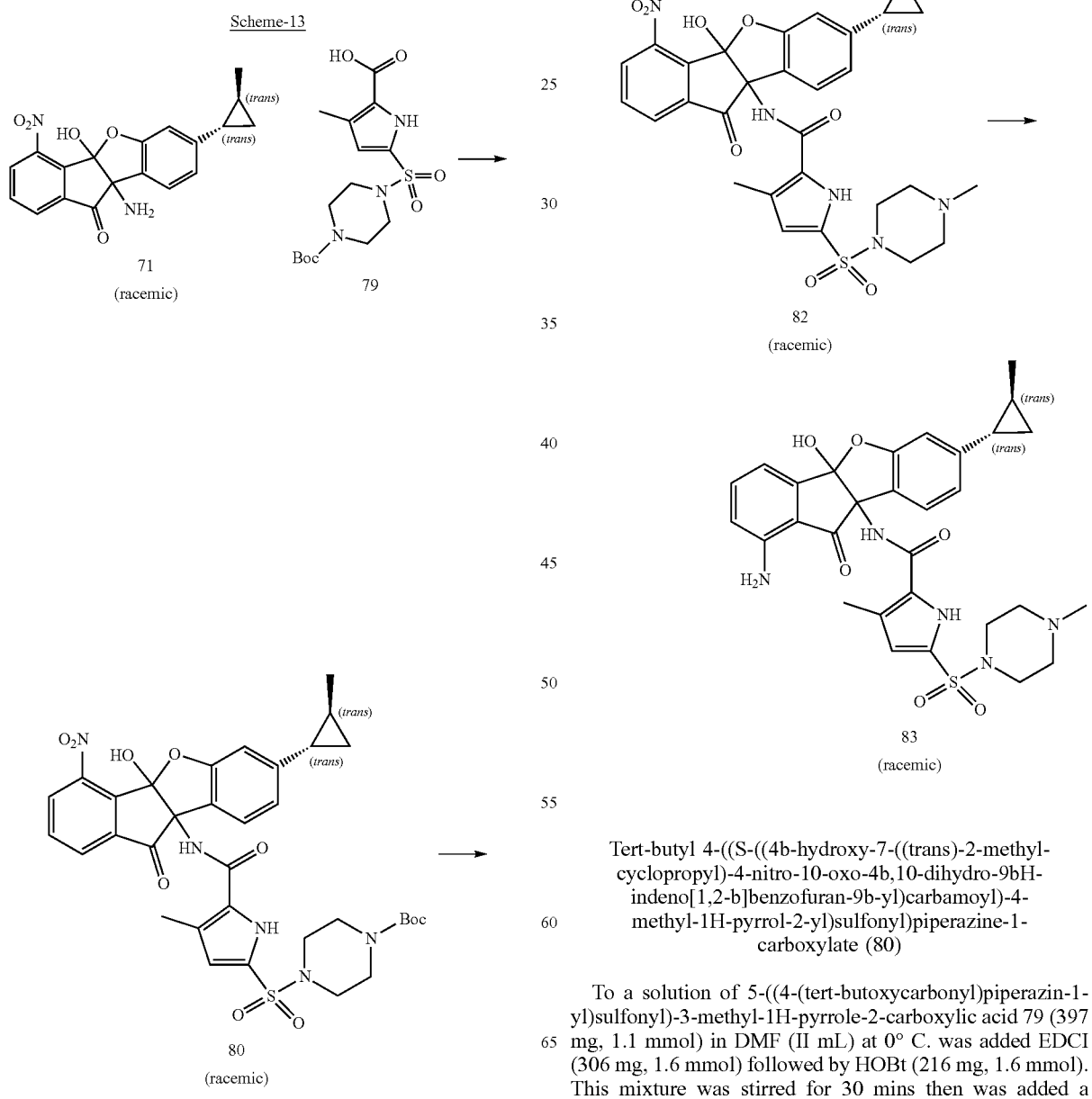

Tert-butyl 4-((S-((4b-hydroxy-7-((trans)-2-methyl-cyclopropyl)-4-nitro-10-oxo-4b,10-dihydro-9bH-indeno[1,2-b]benzofuran-9b-yl)carbamoyl)-4-methyl-1H-pyrrol-2-yl)sulfonyl)piperazine-1-carboxylate (80)

To a solution of 5-((4-(tert-butoxycarbonyl)piperazin-1-yl)sulfonyl)-3-methyl-1H-pyrrole-2-carboxylic acid 79 (397 mg, 1.1 mmol) in DMF (II mL) at 0° C. was added EDCI (306 mg, 1.6 mmol) followed by HOBt (216 mg, 1.6 mmol). This mixture was stirred for 30 mins then was added a racemic mixture of 9b-amino-4b-hydroxy-7-((trans)-2-methylcyclopropyl)-4-nitro-4b,9b-dihydro-10H-indeno[1,2-b]benzofuran-10-one 71 (375 mg, 1.1 mmol) followed by DIPEA (0.6 mL, 3.2 mmol). The reaction mass was stirred at 30° C. for 20 h. The reaction mixture was quenched with water and was extracted with ethyl acetate. Combined organic layer was washed with water and with brine solution. The organic layer was dried over Na₂SO₄ and the solvent was evaporated to get crude. The crude was purified over silica-gel column chromatography to give a solid product.

N-(4b-Hydroxy-7-((trans)-2-methylcyclopropyl)-4-nitro-10-oxo-4b,10-dihydro-9bH-indeno[1,2-b]benzofuran-9b-yl)-3-methyl-S-(piperazin-1-ylsulfonyl)-1H-pyrrole-2-carboxamide (81)

To a solution of racemic tert-butyl 4-((5-((4b-hydroxy-7-((trans)-2-methylcyclopropyl)-4-nitro-10-oxo-4b,10-dihydro-9bH-indeno[1,2-b]benzofuran-9b-yl)carbamoyl)-4-methyl-1H-pyrrol-2-yl)sulfonyl)piperazine-1-carboxylate 80 (250 mg, 0.35 mmol) in DCM (7 mL, 0.05 M) was added 4 N HCl in 1,4-dioxane (0.9 mL, 3.5 mmol) and the reaction mass was stirred for 12 h at room temperature (30° C.). The solvent was evaporated under vacuum, water (10 mL) was added and obtained residue and was basified with 10% NaHCO₃ solution. The aqueous layer was extracted with ethyl acetate and combined organic layer was washed with water and with brine. The organic layer was dried over Na₂SO₄ and the solvent was evaporated to give the solid product, which was used as such in next step without further purifications.

N-(4b-Hydroxy-7-((trans)-2-methylcyclopropyl)-4-nitro-10-oxo-4b,10-dihydro-9bH-indeno[1,2-b]benzofuran-9b-yl)-3-methyl-S-((4-methylpiperazin-1-yl)sulfonyl)-1H-pyrrole-2-carboxamide (82)

To a solution of racemic N-(4b-hydroxy-7-((trans)-2-methylcyclopropyl)-4-nitro-10-oxo-4b,10-dihydro-9bH-indeno[1,2-b]benzofuran-9b-yl)-3-methyl-5-(piperazin-1-ylsulfonyl)-1H-pyrrole-2-carboxamide 81 (100 mg, 0.16 mmol) in gly. AcOH:MeCN (1:1) (4 mL) at 0° C. was added aqueous solution of formaldehyde (35%) (0.15 mL, 1.6 mmol) followed by NaBH₃CN (36 mg, 0.6 mmol). The reaction mass was stirred for 2 h at 0° C. The reaction was quenched with water and aqueous layer was extracted with ethyl acetate and washed with water and with brine. The organic layer was dried over Na₂SO₄ and the solvent was evaporated to get crude. The crude was purified over silica-gel column chromatography to give a solid product.

N-(1-Amino-4b-hydroxy-7-((trans)-2-methylcyclopropyl)-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (83)

To a solution of racemic N-(4b-hydroxy-7-((trans)-2-methylcyclopropyl)-4-nitro-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide 82 (36 mg, 0.06 mmol) in EtOH:H₂O (10:1) (6 mL) was added Fe powder (10 mg, 0.2 mmol) and conc. HCl (1 drop) and the reaction was stirred for 3 h at 90° C. The hot reaction was filtered through CELITE bed. The filtrate was evaporated under vacuum. The residue was dissolved in water and aqueous layer was extracted with ethyl acetate. Combined organic layer was washed with water and with brine. The organic layer was dried over Na₂SO₄ and the solvent was evaporated. The crude was purified over silica gel column chromatography to give a solid product. ¹H-NMR (300 MHz, MeOD) δ 0.70-0.76 (m, 1H), 0.81-0.89 (m, 1H), 0.98-1.02 (m, 1H), 1.16 (d, J=5.7 Hz, 1H), 1.53-1.59 (m, 1H), 2.29 (s, 3H), 2.30 (s, 3H), 2.50-2.53 (m, 4H), 2.99-3.12 (m, 4H), 6.48 (s, 1H), 6.54 (s, 1H), 6.69-6.78 (m, 2H), 7.04 (d, J=7.2 Hz, 1H), 7.33 (d, J=6.3 Hz, 1H), 7.46-7.51 (m, 1H). LCMS: 592.2 (M+H)⁺.

Example 10: (2S,3S)—N-(1-amino-7-((R)-1-cyclopropylethyl)-4b-hydroxy-10-oxo-4b,10-dihydro-9bH-indeno[1,2-b]benzofuran-9b-yl)-2-(dimethylamino)-3-hydroxybutanamide

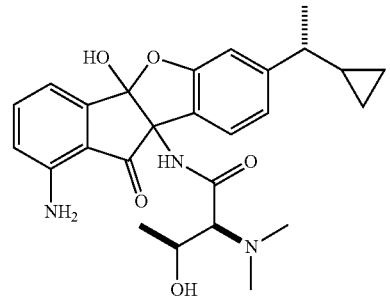 [SMILES: C[C@H](O)[C@@H](C(=O)NC12C(=O)c3c(N)cccc3C1(O)Oc1cc([C@H](C)C3CC3)ccc12)N(C)C]

This compound was prepared similar to Example 9 above. LCMS: 466.4 [M+H]⁺.

Example 11: N-(1-amino-4b-hydroxy-7-((1S,2S)-2-methylcyclopropyl)-10-oxo-4b,10-dihydro-9bH-indeno[1,2-b]benzofuran-9b-yl)-5-(((S)-3-(dimethylamino)pyrrolidin-1-yl)sulfonyl)-3-methyl-1H-pyrrole-2-carboxamide (89)

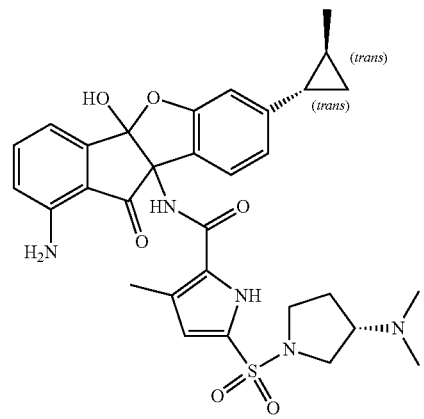

89

Scheme-14

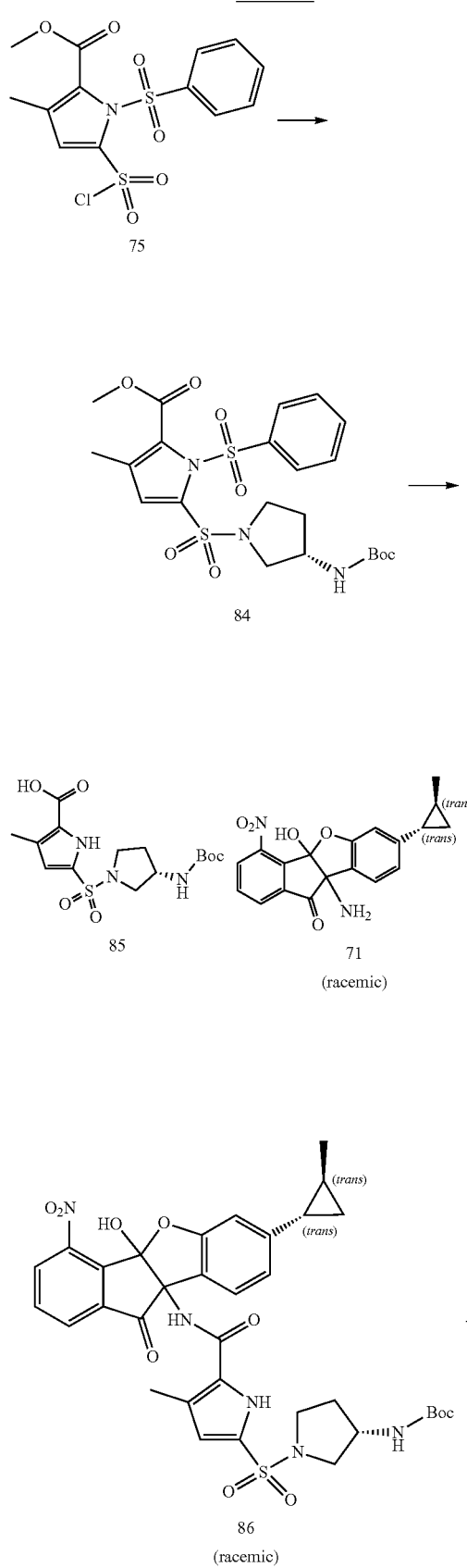

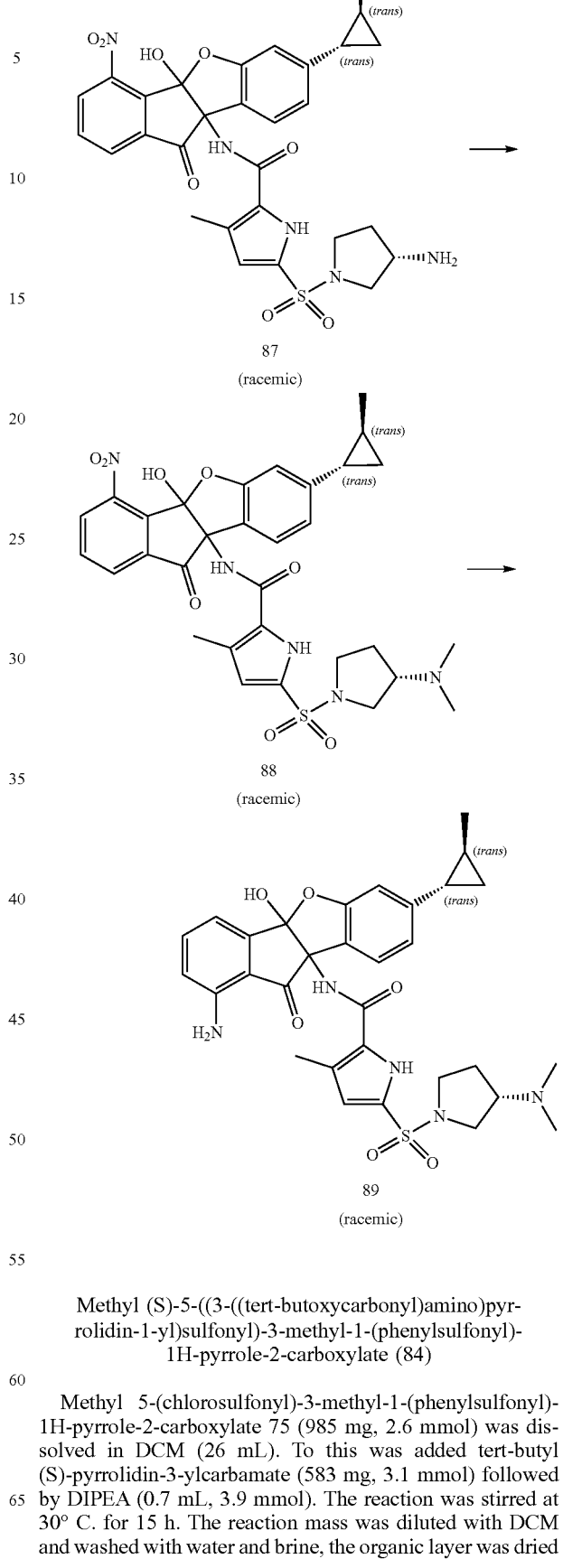

Methyl (S)-5-((3-((tert-butoxycarbonyl)amino)pyrrolidin-1-yl)sulfonyl)-3-methyl-1-(phenylsulfonyl)-1H-pyrrole-2-carboxylate (84)

Methyl 5-(chlorosulfonyl)-3-methyl-1-(phenylsulfonyl)-1H-pyrrole-2-carboxylate 75 (985 mg, 2.6 mmol) was dissolved in DCM (26 mL). To this was added tert-butyl (S)-pyrrolidin-3-ylcarbamate (583 mg, 3.1 mmol) followed by DIPEA (0.7 mL, 3.9 mmol). The reaction was stirred at 30° C. for 15 h. The reaction mass was diluted with DCM and washed with water and brine, the organic layer was dried over anhyd. Na$_2$SO$_4$ and evaporated the solvent to get the crude. The crude was purified with silica-gel column chromatography to give a solid product.

(S)-5-((3-((tert-butoxycarbonyl)amino)pyrrolidin-1-yl)sulfonyl)-3-methyl-1H-pyrrole-2-carboxylic acid (85)

To a solution of methyl (S)-5-((3-((tert-butoxycarbonyl)amino)pyrrolidin-1-yl)sulfonyl)-3-methyl-1-(phenylsulfonyl)-1H-pyrrole-2-carboxylate 84 (1.10 g, 2.1 mmol) in MeOH:THF:H$_2$O (1:1:10) (42 mL) was added LiOH·H$_2$O (855 mg, 20.8 mmol) and the reaction was stirred for 15 h at 80° C. Organic solvent was evaporated. The reaction mixture was acidified with 1 N HCl solution, the aqueous layer was extracted with ethyl acetate, and combined organic layer was washed with brine. The organic layer was dried over Na$_2$SO$_4$, and the solvent was evaporated under vacuum to give a solid product.

Tert-butyl ((3S)-1-((5-((4b-hydroxy-7-((trans)-2-methylcyclopropyl)-4-nitro-10-oxo-4b,10-dihydro-9bH-indeno[1,2-b]benzofuran-9b-yl)carbamoyl)-4-methyl-1H-pyrrol-2-yl)sulfonyl)pyrrolidin-3-yl)carbamate (86)

To a solution of (S)-5-((3-((tert-butoxycarbonyl)amino)pyrrolidin-1-yl)sulfonyl)-3-methyl-1H-pyrrole-2-carboxylic acid 85 (276 mg, 0.7 mmol) in DMF (7 mL) at 0° C. was added EDCI (212 mg, 1.1 mmol) followed by HOBt (149 mg, 1.1 mmol). The mixture was stirred for 30 mins and then was added a racemic mixture of 9b-amino-4b-hydroxy-7-((trans)-2-methylcyclopropyl)-4-nitro-4b,9b-dihydro-10H-indeno[1,2-b]benzofuran-10-one 71 (260 mg, 0.7 mmol) followed by DIPEA (0.4 mL, 2.2 mmol). The reaction mass was stirred at rt. (30° C.) for 20 h. The reaction quenched with water and aqueous layer was extracted with ethyl acetate. The organic layer was washed with water and with brine, and organic layer was dried over Na$_2$SO$_4$. The solvent was evaporated under vacuum to get the crude. The crude was purified over silica-gel column chromatography to give product.

5-(((S)-3-Aminopyrrolidin-1-yl)sulfonyl)-N-(4b-hydroxy-7-((trans)-2-methylcyclopropyl)-4-nitro-10-oxo-4b,10-dihydro-9bH-indeno[1,2-b]benzofuran-9b-yl)-3-methyl-1H-pyrrole-2-carboxamide (87)

To a stirred solution of a racemic mixture of tert-butyl ((3S)-1-((5-((4b-hydroxy-7-((trans)-2-methylcyclopropyl)-4-nitro-10-oxo-4b,10-dihydro-9bH-indeno[1,2-b]benzofuran-9b-yl)carbamoyl)-4-methyl-1H-pyrrol-2-yl)sulfonyl)pyrrolidin-3-yl)carbamate 86 (170 mg, 0.24 mmol) in DCM (5 mL, 0.05 M), was added 4 N HCl in 1,4-dioxane (0.6 mL, 2.4 mmol) and the reaction was stirred for 12 h at room temperature (30° C.). The solvent was evaporated, the residue was dissolved in water (10 mL) and basified with 10% NaHCO$_3$ solution. The aqueous layer was extracted with ethyl acetate and combined organic layer was washed with water and with brine and organic layer was dried over Na$_2$SO$_4$. The solvent was evaporated under vacuum to give product.

5-(((S)-3-(Dimethylamino)pyrrolidin-1-yl)sulfonyl)-N-(4b-hydroxy-7-((trans)-2-methylcyclopropyl)-4-nitro-10-oxo-4b,10-dihydro-9bH-indeno[1,2-b]benzofuran-9b-yl)-3-methyl-1H-pyrrole-2-carboxamide (88)

To a stirred solution of a racemic mixture of 5-(((S)-3-aminopyrrolidin-1-yl)sulfonyl)-N-(4b-hydroxy-7-((trans)-2-methylcyclopropyl)-4-nitro-10-oxo-4b,10-dihydro-9bH-indeno[1,2-b]benzofuran-9b-yl)-3-methyl-1H-pyrrole-2-carboxamide 87 (120 mg, 0.2 mmol) in gly. AcOH:MeCN=1:1 (7 mL, 0.03 M) at 0° C., was added formaldehyde (35% aqueous solution) (0.34 mL, 3.9 mmol) followed by NaBH$_3$CN (62 mg, 1.0 mmol). The reaction mass was stirred for 2 h at 0° C. The reaction was quenched with water and aqueous layer was extracted with ethyl acetate and washed with water and with brine. The organic layer was dried over Na$_2$SO$_4$ and evaporated solvent under vacuum to get crude. The crude was purified over silica-gel column chromatography to give product.

N-(1-Amino-4b-hydroxy-7-((trans)-2-methylcyclopropyl)-10-oxo-4b,10-dihydro-9bH-indeno[1,2-b]benzofuran-9b-yl)-5-(((S)-3-(dimethylamino)pyrrolidin-1-yl)sulfonyl)-3-methyl-1H-pyrrole-2-carboxamide (89)

To a stirred solution of a racemic mixture of 5-(((S)-3-(dimethylamino)pyrrolidin-1-yl)sulfonyl)-N-(4b-hydroxy-7-((trans)-2-methylcyclopropyl)-4-nitro-10-oxo-4b,10-dihydro-9bH-indeno[1,2-b]benzofuran-9b-yl)-3-methyl-1H-pyrrole-2-carboxamide 88 (32 mg, 0.05 mmol) in EtOH:H$_2$O (10:1) (5 mL), was added Fe powder (8 mg, 0.2 mmol) and conc. HCl (1 drop) and the reaction mass was stirred for 3 h at 90° C. The hot reaction mass was filtered through CELITE bed. The filtrate was evaporated under vacuum, the residue obtained was dissolved in ethyl acetate an was washed with water and with brine. The organic layer was dried over Na$_2$SO$_4$ and the solvent was evaporated under vacuum to get crude. The crude was purified over silica gel column chromatography to give a solid product. $^1$H-NMR (300 MHz, MeOD) δ 0.70-0.76 (m, 1H), 0.82-0.89 (m, 1H), 0.97-1.07 (m, 1H), 1.16 (d, J=5.7 Hz, 3H), 1.53-1.59 (m, 1H), 1.62-1.72 (m, 1H), 2.02-2.08 (m, 1H), 2.22 (s, 6H), 2.31 (s, 3H), 2.64-2.75 (m, 1H), 2.98-3.05 (m, 1H), 3.16-3.27 (m, 1H), 3.41-3.53 (m, 2H), 6.48 (s, 1H), 6.58 (s, 1H), 6.69-6.77 (m, 2H), 7.04 (d, J=7.2 Hz, 1H), 7.33 (d, J=7.2 Hz, 1H), 7.47-7.52 (m, 1H). LCMS: 606.3 (M+H)$^+$.

Example 12: N-((4bR,9bR)-1-amino-4b-hydroxy-7-((trans)-2-methylcyclopropyl)-10-oxo-4b,10-dihydro-9bH-indeno[1,2-b]benzofuran-9b-yl)-3,4-dimethyl-5-((4-methylpiperazin-1-yl)sulfonyl)-1H-pyrrole-2-carboxamide

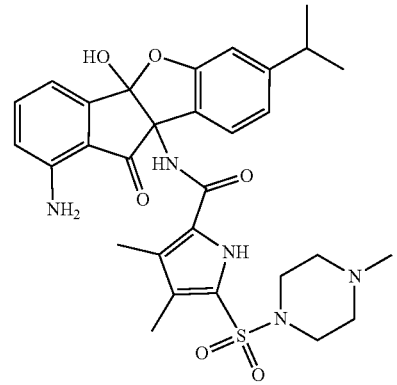 [SMILES: Cc1c(C(=O)NC23C(=O)c4c(N)cccc4C2(O)Oc2cc(C(C)C)ccc23)[nH]c(S(=O)(=O)N2CCN(C)CC2)c1C]

Scheme-15
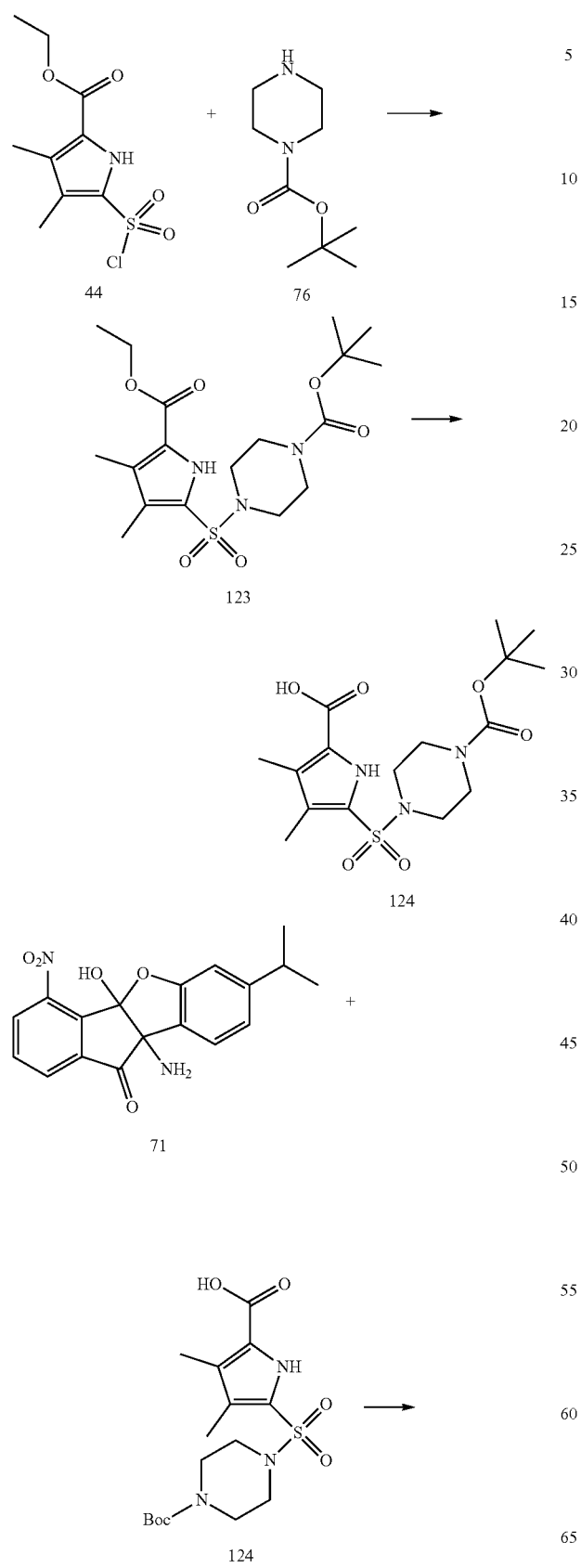
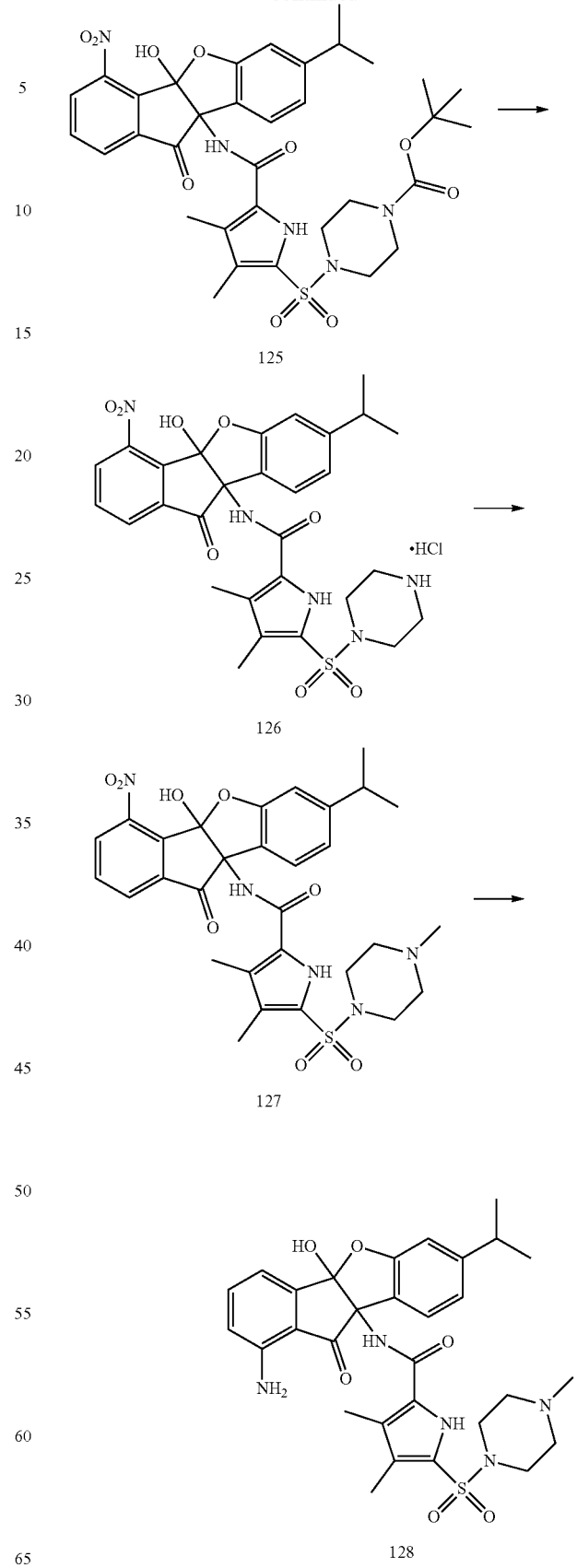

Tert-butyl 4-((5-(ethoxycarbonyl)-3,4-dimethyl-1H-pyrrol-2-yl)sulfonyl)piperazine-1-carboxylate (123)

Ethyl 5-(chlorosulfonyl)-3,4-dimethyl-1H-pyrrole-2-carboxylate (530 mg, 2.0 mmol) was taken in DCM (20 mL, 0.1 M) and to this was added tert-butyl piperazine-1-carboxylate (448 mg, 2.4 mmol) followed by addition of DIPEA (0.52 mL, 3.0 mmoL) at room temperature. The reaction mass was then stirred at r.t. (25° C.) for next 18 hours. The reaction mass was quenched with water (50 mL) and then extracted with DCM (70 mL×2). The combined organic layer was washed with water (30 ml) and brine (30 ml). This was dried over anhy. $Na_2SO_4$ and concentrated off to get the crude product. The crude product was purified over silica gel column chromatography (10-20% EA in hexanes) to get the pure product.

5-((4-(Tert-butoxycarbonyl)piperazin-1-yl)sulfonyl)-3,4-dimethyl-1H-pyrrole-2-carboxylic acid (124)

Tert-butyl 4-((5-(ethoxycarbonyl)-3,4-dimethyl-1H-pyrrol-2-yl)sulfonyl)piperazine-1-carboxylate (580 mg, 1.4 mmol) was taken in THF:MeOH:$H_2O$ (1:1:10, 28.0 mL, 0.05 M) and charged with LiOH·$H_2O$ (294 mg, 7.0 mmol) and the reaction was refluxed at 80° C. for 5 hours. The reaction mass was concentrated off to remove the volatiles. This was then acidified with 1 N HCl (pH<2-3). The solid precipitated was then filtered off, washed with cold water and dried to get the product.

Tert-butyl 4-(5-((4b-hydroxy-7-isopropyl-4-nitro-10-oxo-4b,10-dihydro-9bH-indeno[1,2-b]benzofuran-9b-yl)carbamoyl)-3,4-dimethyl-1H-pyrrole-2-carbonyl)piperazine-1-carboxylate (125)

5-(4-(Tert-butoxycarbonyl)piperazine-1-carbonyl)-3,4-dimethyl-1H-pyrrole-2-carboxylic acid (264 mg, 0.75 mmol) was taken in DMF (4 mL, 0.2 M) and cooled to 0° C. This was charged with EDC.HCl (216 mg, 1.125 mmol) and HOBt (152 mg, 1.125 mmol). After 10 mins it was charged with 9b-amino-4b-hydroxy-7-isopropyl-4-nitro-4b,9b-dihydro-10H-indeno[1,2-b]benzofuran-10-one (255 mg, 0.75 mmol) followed by addition of DIPEA (0.33 mL, 1.875 mmol) and allowed to attain room temperature (35° C.) by itself. This was stirred for next 18 h. The reaction mass was then quenched with water (30 mL) and extracted with EA (50 mL×2). Organic layer was washed with brine (30 mL), dried over anhy. $Na_2SO_4$ and concentrated. Crude was purified on silica gel column chromatography (20-50% EA:MeOH (4:1) in hexanes) to get the impure product, which was again purified with MeOH/DCM system to get the pure product.

N-(4b-hydroxy-7-isopropyl-4-nitro-10-oxo-4b,10-dihydro-9bH-indeno[1,2-b]benzofuran-9b-yl)-3,4-dimethyl-5-(piperazine-1-carbonyl)-1H-pyrrole-2-carboxamide (126)

Tert-butyl 4-(5-((4b-hydroxy-7-isopropyl-4-nitro-10-oxo-4b,10-dihydro-9bH-indeno[1,2-b]benzofuran-9b-yl)carbamoyl)-3,4-dimethyl-1H-pyrrole-2-carbonyl)piperazine-1-carboxylate (135 mg, 0.2 mmol) was taken in DCM (2.0 mL, 0.1 M), and to this 4 M HCl in dioxane (0.50 mL, 2.0 mmol) was added. This was stirred at room temperature (25° C.) for 15 hours. The reaction mass was concentrated off and the residue was taken in EA (20-30 mL) and stirred with sat. $NaHCO_3$(20 mL, appx.) for 5-10 mins. This was extracted with EA (50 mL×2). The combine organic layers were washed with water (30 mL) and brine (30 mL). This was dried off over anhy. $Na_2SO_4$ and concentrated off to get the crude. Crude was used in the next step without further purification.

N-(4b-hydroxy-7-isopropyl-4-nitro-10-oxo-4b,10-dihydro-9bH-indeno[1,2-b]benzofuran-9b-yl)-3,4-dimethyl-5-(4-methylpiperazine-1-carbonyl)-1H-pyrrole-2-carboxamide (127)

N-(4b-hydroxy-7-isopropyl-4-nitro-10-oxo-4b,10-dihydro-9bH-indeno[1,2-b]benzofuran-9b-yl)-3,4-dimethyl-5-(piperazine-1-carbonyl)-1H-pyrrole-2-carboxamide (90 mg, 0.15 mmol) was taken in MeCN:gl. AcOH (2:1, 3 mL, 0.05 M) cooled to 0° C. This was charged with 35% HCHO aq. solution (0.13 mL, 1.5 mmol) followed by addition of $NaBH_3CN$ (33 mg, 0.525 mmol). This was stirred at 0° C. for next 2 hours The reaction mass was quenched with water (20 mL), sat. $NaHCO_3$(20 mL) and extracted with EA (40 mL×2). The combined organic layers were washed with water (30 mL) and brine (10 mL). This was dried over anhy. $Na_2SO_4$ and concentrated off to get the crude. Crude was purified over thin layer silica gel column chromatography (0-5% MeOH in DCM) to get pure product.

N-(1-amino-4b-hydroxy-7-isopropyl-10-oxo-4b,10-dihydro-9bH-indeno[1,2-b]benzofuran-9b-yl)-3,4-dimethyl-5-(4-methylpiperazine-1-carbonyl)-1H-pyrrole-2-carboxamide (128)

N-(4b-hydroxy-7-isopropyl-4-nitro-10-oxo-4b,10-dihydro-9bH-indeno[1,2-b]benzofuran-9b-yl)-3,4-dimethyl-5-(4-methylpiperazine-1-carbonyl)-1H-pyrrole-2-carboxamide (60 mg, 0.1 mmol) was taken in EtOH:water (10:1, 5.0 mL, 0.02 M), and to this Fe powder (17 mg, 0.3 mmol) was charged followed by 6.0 M HCl (1 drop). This was refluxed at 90° C. for next 2.0 hours. The reaction mass was filtered over CELITE under warm conditions using EA (30 mL). The filtrate was concentrated off and taken in EA (100 mL) and washed with sat. $NaHCO_3$ (20 mL×2), water (20 mL×2) and brine (20 mL). This was dried over anhy. $Na_2SO_4$ and concentrated to get the crude. Crude was purified over silica gel column chromatography (0-10% MeOH in DCM) to get the pure product.

1H NMR (500 MHz, METHANOL-d4) δ: 7.48 (br s, 2H), 7.05 (br s, 1H), 6.89 (br s, 1H), 6.70 (br s, 2H), 3.10 (br s, 4H), 2.87 (dt, J=13.4, 6.6 Hz, 1H), 2.51 (br t, J=4.4 Hz, 4H), 2.29 (s, 3H), 2.22 (s, 3H), 2.21 (s, 3H), 1.21 (d, J=6.9 Hz, 6H); LCMS: 594.2 (M+H)+

Example 13: N-(1-amino-4b-hydroxy-7-isopropyl-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide

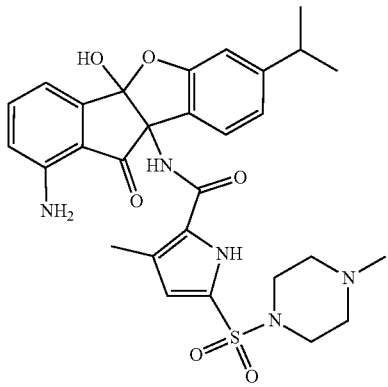 [SMILES: Cc1cc(S(=O)(=O)N2CCN(C)CC2)[nH]c1C(=O)NC12C(=O)c3c(N)cccc3C1(O)Oc1cc(C(C)C)ccc12]

The above compound was prepared by the following schemes.

Scheme-16

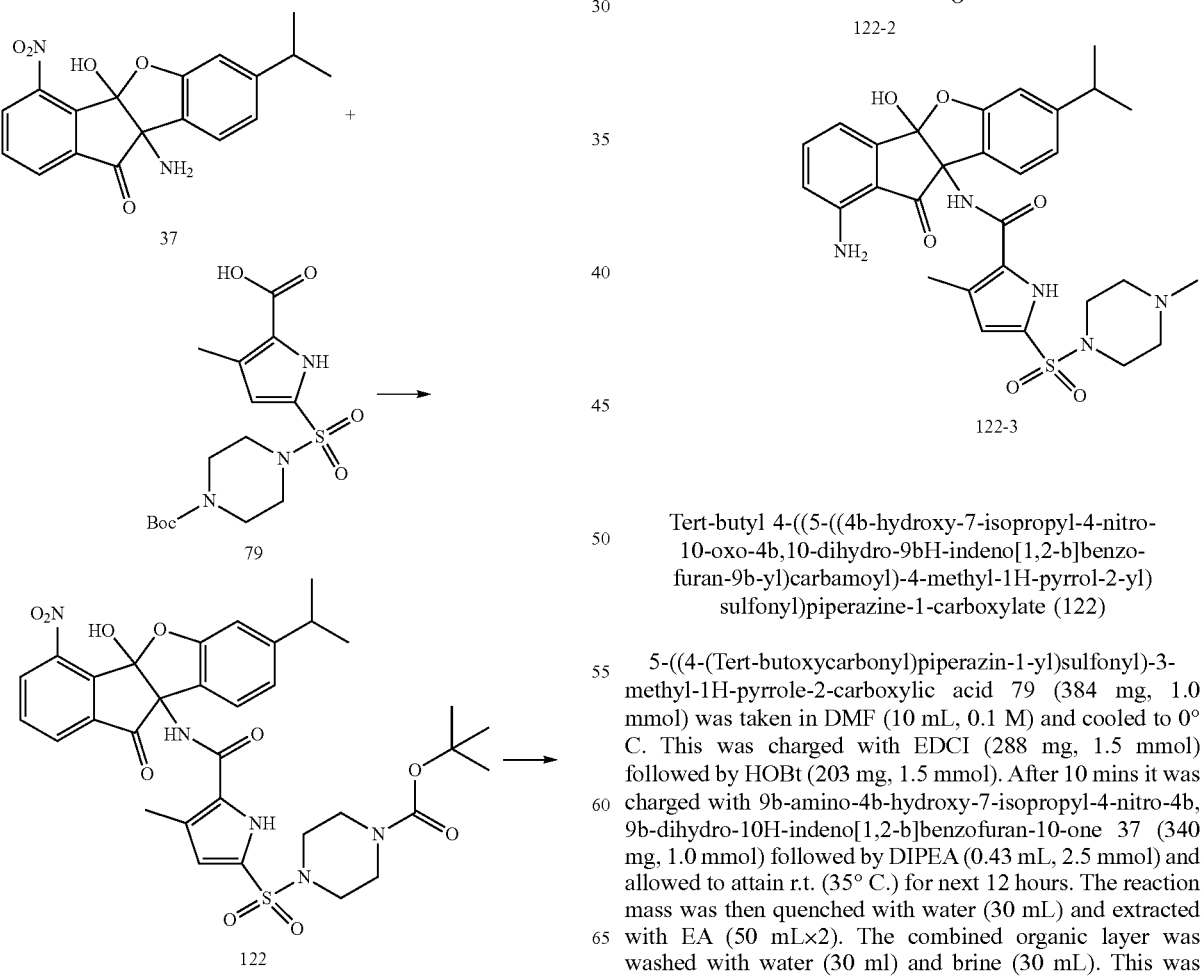

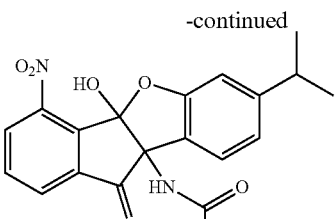

122-1

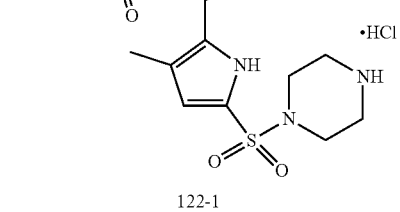

122-2

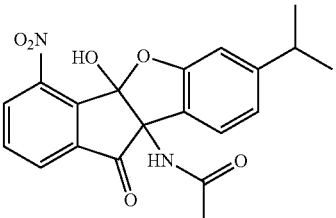

122-3

Tert-butyl 4-((5-(((4b-hydroxy-7-isopropyl-4-nitro-10-oxo-4b,10-dihydro-9bH-indeno[1,2-b]benzofuran-9b-yl)carbamoyl)-4-methyl-1H-pyrrol-2-yl)sulfonyl)piperazine-1-carboxylate (122)

5-((4-(Tert-butoxycarbonyl)piperazin-1-yl)sulfonyl)-3-methyl-1H-pyrrole-2-carboxylic acid 79 (384 mg, 1.0 mmol) was taken in DMF (10 mL, 0.1 M) and cooled to 0° C. This was charged with EDCI (288 mg, 1.5 mmol) followed by HOBt (203 mg, 1.5 mmol). After 10 mins it was charged with 9b-amino-4b-hydroxy-7-isopropyl-4-nitro-4b,9b-dihydro-10H-indeno[1,2-b]benzofuran-10-one 37 (340 mg, 1.0 mmol) followed by DIPEA (0.43 mL, 2.5 mmol) and allowed to attain r.t. (35° C.) for next 12 hours. The reaction mass was then quenched with water (30 mL) and extracted with EA (50 mL×2). The combined organic layer was washed with water (30 ml) and brine (30 mL). This was dried over anhyd. Na₂SO₄ and concentrated. The crude was purified over silica gel column chromatography (25-30% EA in hexanes) to get the product.

N-(4-((11-azaneyl)peroxy)-4b-hydroxy-7-isopropyl-10-oxo-4b,10-dihydro-9bH-indeno[1,2-b]benzofuran-9b-yl)-3-methyl-5-(piperazin-1-ylsulfonyl)-1H-pyrrole-2-carboxamide (122-1)

To a stirred solution of tert-butyl 4-((5-((4b-hydroxy-7-isopropyl-4-nitro-10-oxo-4b,10-dihydro-9bH-indeno[1,2-b]benzofuran-9b-yl)carbamoyl)-4-methyl-1H-pyrrol-2-yl)sulfonyl)piperazine-1-carboxylate (340 mg, 0.49 mmol) in DCM (10 mL) was added 4N HCl in dioxane (1.2 mL, 4.9 mmol) at r.t. The resulting reaction mass was stirred at r.t for 15 h. Reaction mass was evaporated to dryness, the residue obtained was dissolved in water (50 mL) and was basified with saturated solution of NaHCO$_3$, the product was extracted with EA (50 mL×3) combined organic layer was washed with water and brine solution. Organic layer was dried over anhy. Na$_2$SO$_4$, evaporated solvent to get crude product. Crude was purified over silica-gel column chromatography (MeOH:DCM=1:20) to get desired product.

N-(4-((11-azaneyl)peroxy)-4b-hydroxy-7-isopropyl-10-oxo-4b,10-dihydro-9bH-indeno[1,2-b]benzofuran-9b-yl)-3-methyl-S-((4-methylpiperazin-1-yl)sulfonyl)-1H-pyrrole-2-carboxamide (122-2)

To a stirred solution of N-(4-((11-azaneyl)peroxy)-4b-hydroxy-7-isopropyl-10-oxo-4b,10-dihydro-9bH-indeno[1,2-b]benzofuran-9b-yl)-3-methyl-5-(piperazin-1-ylsulfonyl)-1H-pyrrole-2-carboxamide 122-1 (100 mg, 0.17 mmol) in gly·AcOH:MeCN (4 mL) at 0° C. was added 35% formaldehyde solution (0.15 mL, 1.7 mmol) followed by addition of NaBH$_3$CN (36 mg, 0.6 mmol) the resulting reaction mass was stirred for 2 h at 0° C. Reaction mass was quenched with water and desired product was extracted with EA (50 mL×3) combined organic layer was washed with water and brine solution. Organic layer was dried over anhy. Na$_2$SO$_4$, evaporated solvent to get crude product. Crude was purified over silica-gel column chromatography (MeOH:DCM=1:20) to get desired product.

N-(1-amino-4b-hydroxy-7-isopropyl-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (122-3)

Fe powder (14 mg, 0.25 mmol) was added to stirred solution of N-(4-((11-azaneyl)peroxy)-4b-hydroxy-7-isopropyl-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (51 mg, 0.08 mmol) in EtOH:H$_2$O (3 mL) followed by addition of conc·HCl (1 drop). The resulting reaction mass was refluxed at 90° C. for 3 h. Hot reaction mass was filtered through celite bed and was washed with EA. Organic layer was evaporated to dryness, the residue obtained was dissolved in EA (100 mL) and was washed with water (50 mL×2) and brine solution. Organic layer was dried over anhy. Na$_2$SO$_4$, evaporated solvent to get crude product. Crude was purified over silica-gel column chromatography to get desired product. $^1$H NMR (300 MHz, MeOD) δ 7.42-7.33 (m, 1H), 7.03 (d, J=7.4 Hz, 1H), 6.87 (d, J=7.9 Hz, 1H), 6.81-6.72 (m, 1H), 6.69 (s, 1H), 6.52 (s, 1H), 3.11-2.98 (m, 4H), 2.89-2.80 (m, 1H), 2.59-2.46 (m, 4H), 2.28 (s, 3H), 1.19 (d, J=6.9 Hz, 6H). Mass: [M+H]$^+$: 580.1

Example 14: N-((4bR,9bR)-1-amino-4b-hydroxy-7-((1S,2S)-2-methylcyclopropyl)-10-oxo-4b,10-dihydro-9bH-indeno[1,2-b]benzofuran-9b-yl)-3-methyl-S-((4-methylpiperazin-1-yl)sulfonyl)-1H-pyrrole-2-carboxamide

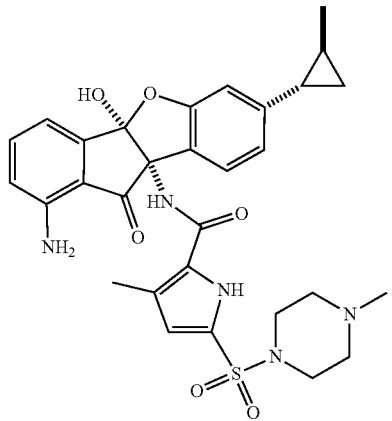

Scheme-17

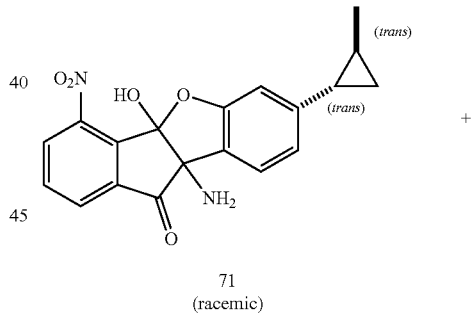

71
(racemic)

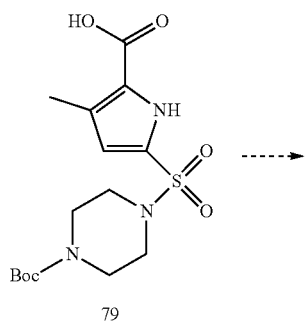

79

75
-continued

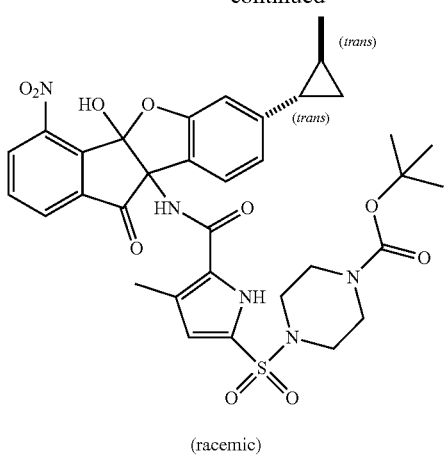
(racemic)

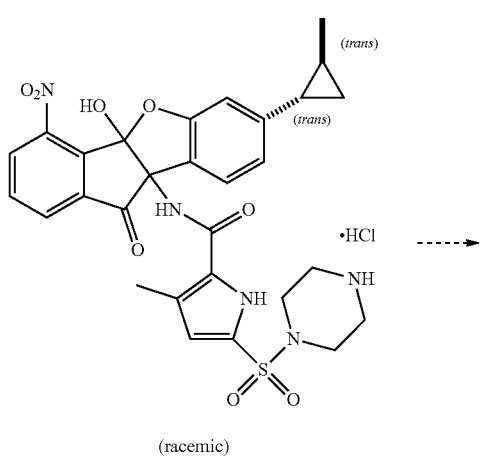
·HCl
(racemic)

76
-continued

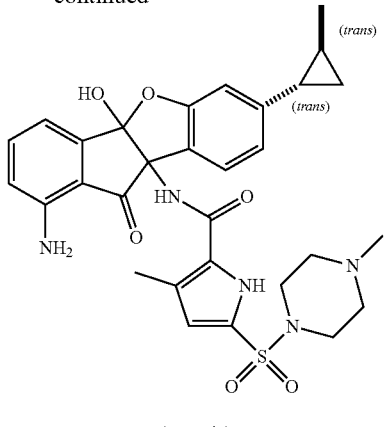
(racemic)

This compound was prepared similar to Example 12 according to the above scheme with 3,4-dimethylpyrrole derivative. (300 MHz, MeOD) δ 0.70-0.76 (m, 1H), 0.81-0.89 (m, 1H), 0.98-1.02 (m, 1H), 1.16 (d, J=5.7 Hz, 1H), 1.53-1.59 (m, 1H), 2.29 (s, 3H), 2.30 (s, 3H), 2.50-2.53 (m, 4H), 2.99-3.12 (m, 4H), 6.48 (s, 1H), 6.54 (s, 1H), 6.69-6.78 (m, 2H), 7.04 (d, J=7.2 Hz, 1H), 7.33 (d, J=6.3 Hz, 1H), 7.46-7.51 (n, 1H). LCMS: 592.1 (M+H)$^+$, HPLC purity: 95.4%

Example 15: (2S,3S)—N-((4bR,9bR)-1-amino-7-((S)-1-cyclopropylethyl)-4b-hydroxy-10-oxo-4b,10-dihydro-9bH-indeno[1,2-b]benzofuran-9b-yl)-2-(dimethylamino)-3-hydroxybutanamide

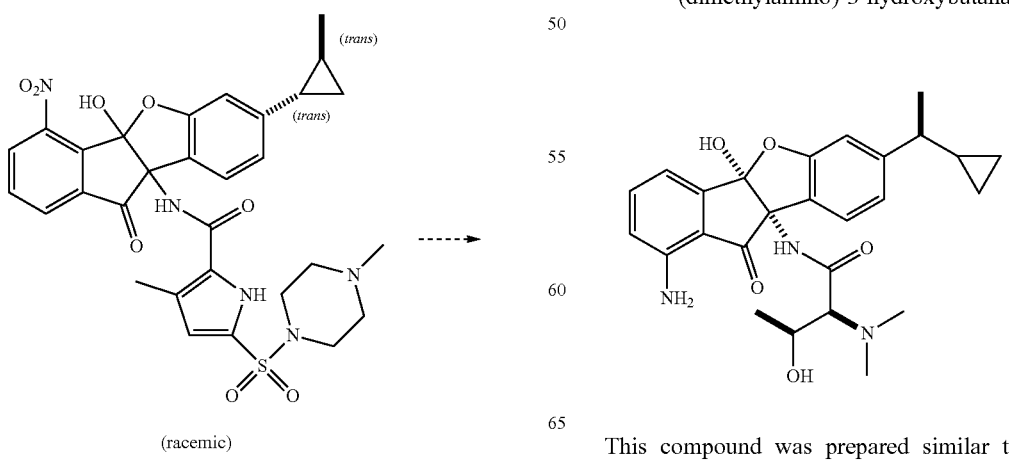

This compound was prepared similar to Example 12 above. LCMS: 466.3 [M+H]$^+$.

Example 16: N-(1-amino-4b-hydroxy-7-((1R,2S)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide

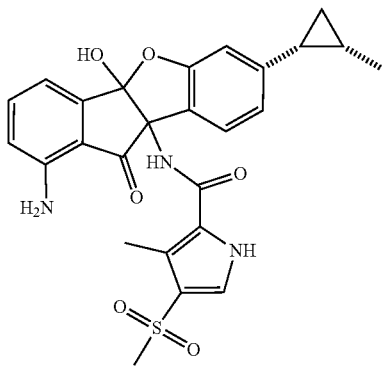

This compound was prepared similar to Example 12 above. LCMS: 508.3 [M+H]⁺.

Example 17: N-((4bR,9bR)-1-amino-7-((R)-1-cyclopropylethyl)-4b-hydroxy-10-oxo-4b,10-dihydro-9bH-indeno[1,2-b]benzofuran-9b-yl)-2-(azetidin-1-yl)acetamide (92)

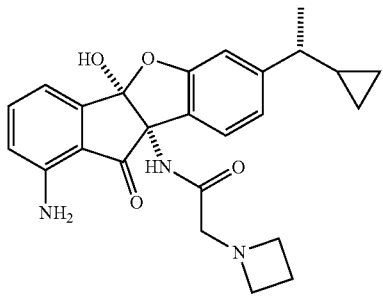 [SMILES: C[C@@H](c1ccc2c(c1)O[C@]1(O)c3cccc(N)c3C(=O)[C@]21NC(=O)CN1CCC1)C1CC1]

Scheme-18

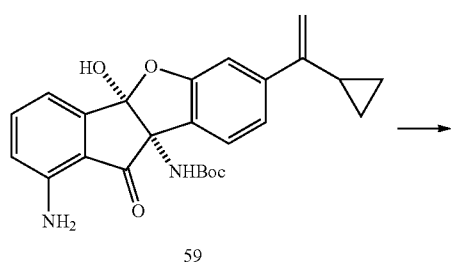

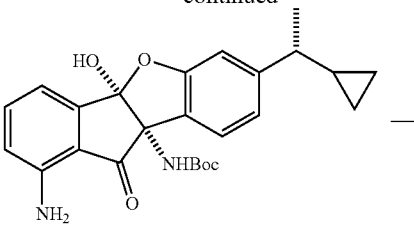

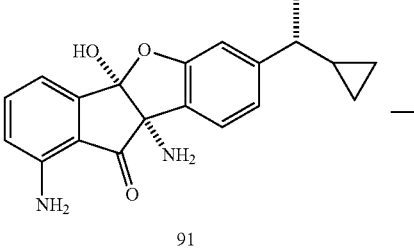

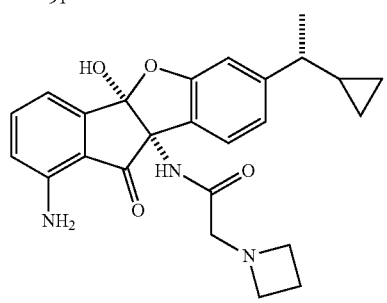

Tert-butyl ((4bR,9bR)-1-amino-7-((R)-1-cyclopropylethyl)-4b-hydroxy-10-oxo-4b,10-dihydro-9bH-indeno[1,2-b]benzofuran-9b-yl)carbamate (90)

Tert-butyl ((4bR,9bR)-1-amino-7-(1-cyclopropylvinyl)-4b-hydroxy-10-oxo-4b,10-dihydro-9bH-indeno[1,2-b]benzofuran-9b-yl)carbamate 59 (174 mg, 0.40 mmol) was taken in DCM (8.0 mL, 0.05 M) and charged with [((4R,5R)-Cy2-UBaphox)Ir(COD)]BARF (13.9 mg, 0.008 mmol) under nitrogen. This was then flushed with H₂ gas and then kept under H₂ atmosphere (60 psi) for next 4 hour at r.t. (20° C.). The reaction mass was then concentrated and passed through a short plug of silica. This was concentrated off to get the crude. The crude was purified over silica gel column chromatography and then with preparative HPLC (ADH column (Diacel 250×20 mm, EtOH:MeOH:Hexane=36:4:60).

(4bR,9bR)-1,9b-Diamino-7-((R)-1-cyclopropylethyl)-4b-hydroxy-4b,9b-dihydro-10H-indeno[1,2-b]benzofuran-10-one (91)

Enantiopure tert-butyl ((4bR,9bR)-1-amino-7-((R)-1-cyclopropylethyl)-4b-hydroxy-10-oxo-4b,10-dihydro-9bH-indeno[1,2-b]benzofuran-9b-yl)carbamate 90 (70 mg, 0.16 mmol) was taken in DCM (1.6 mL, 0.1 M) and immediately charged with 4.0 M HCl in dioxane (0.40 mL, 1.60 mmol). The reaction mixture was then stirred at r.t. (20° C.) for next 6 hours. The reaction mixture was diluted with EA (~50 mL) and stirred with sat. NaHCO₃(~30 mL) for 5-10 mins. The layers were separated off and aq. layer was extracted with EA (~30 mL×2). The combined org. layer was washed with water (30 ml) and brine (~30 mL). This was dried over N-((4bR,9bR)-1-Amino-7-((R)-1-cyclopropylethyl)-4b-hydroxy-10-oxo-4b,10-dihydro-9bH-indeno[1,2-b]benzofuran-9b-yl)-2-(azetidin-1-yl)acetamide (92)

2-(Azetidin-1-yl)acetic acid hydrochloride 58 (34 mg, 0.23 mmol) in 1.5 mL anhydrous DMF (0.1 M) was charged with HATU (87.5 mg, 0.23 mmol) and DIPEA (79 μL, 0.23 mmol) at 0° C. After 10 mins this was charged with (4bR,9bR)-1,9b-diamino-7-((R)-1-cyclopropylethyl)-4b-hydroxy-4b,9b-dihydro-10H-indeno[1,2-b]benzofuran-10-one 91 (51 mg, 0.15 mmol) and stirred at r.t. (20° C.) for 15 h. The reaction mass was quenched with water (~20 mL) and sat. NaHCO$_3$(~30 mL). This was extracted with EA (50 mL×3). The combined organic layers were washed with water (30 mL×2), brine (30 mL) and dried over anhyd. Na$_2$SO$_4$ and concentrated off to get the crude. Crude was purified over silica gel column chromatography (0-10% MeOH in DCM) to get the solid product. $^1$H-NMR (300 MHz, MeOD) δ 7.51-7.39 (m, 1H), 7.28 (d, J=7.9 Hz, 1H), 6.99 (d, J=7.0 Hz, 1H), 6.85 (dd, J=7.9, 1.3 Hz, 1H), 6.78-6.65 (m, 2H), 3.38 (t, J=7.2 Hz, 4H), 3.19 (s, 2H), 2.14-2.03 (m, 2H), 1.91-1.84 (m, 1H), 1.25 (d, J=7.0 Hz, 3H), 0.96-0.80 (m, 1H), 0.54-0.49 (m, 1H), 0.37-0.32 (m, 1H), 0.23-0.12 (m, 1H), 0.10-0.02 (m, 1H). LCMS: 432.2 [M−H]$^−$. LCMS: 434.3 [M+H]$^+$.

Example 18: N-((4bR,9bR)-1-amino-7-((S)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide

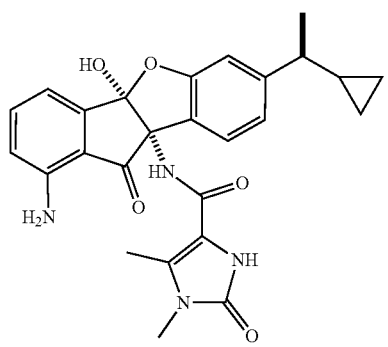 [SMILES: Cc1c(C(=O)N[C@]23C(=O)c4c(N)cccc4[C@@]2(O)Oc2cc([C@@H](C)C4CC4)ccc23)[nH]c(=O)n1C]

This compound was prepared similar to Example 15 above. LCMS: 475.1 [M+H]$^+$.

Example 19 and 20: N-((4bR,9bR)-1-amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (101) and N-((4bS,9bS)-1-amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (102)

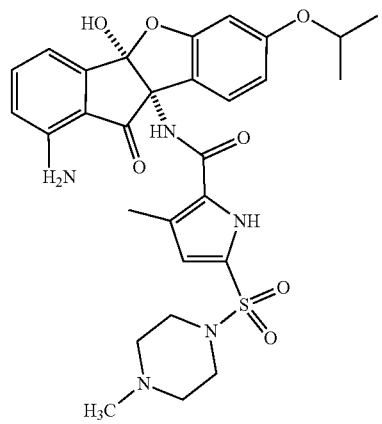

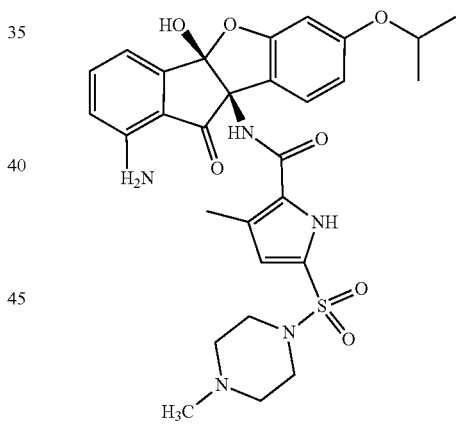

Scheme-19

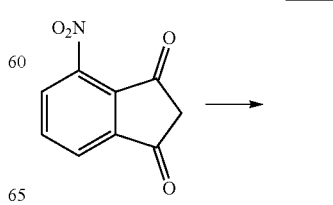

4

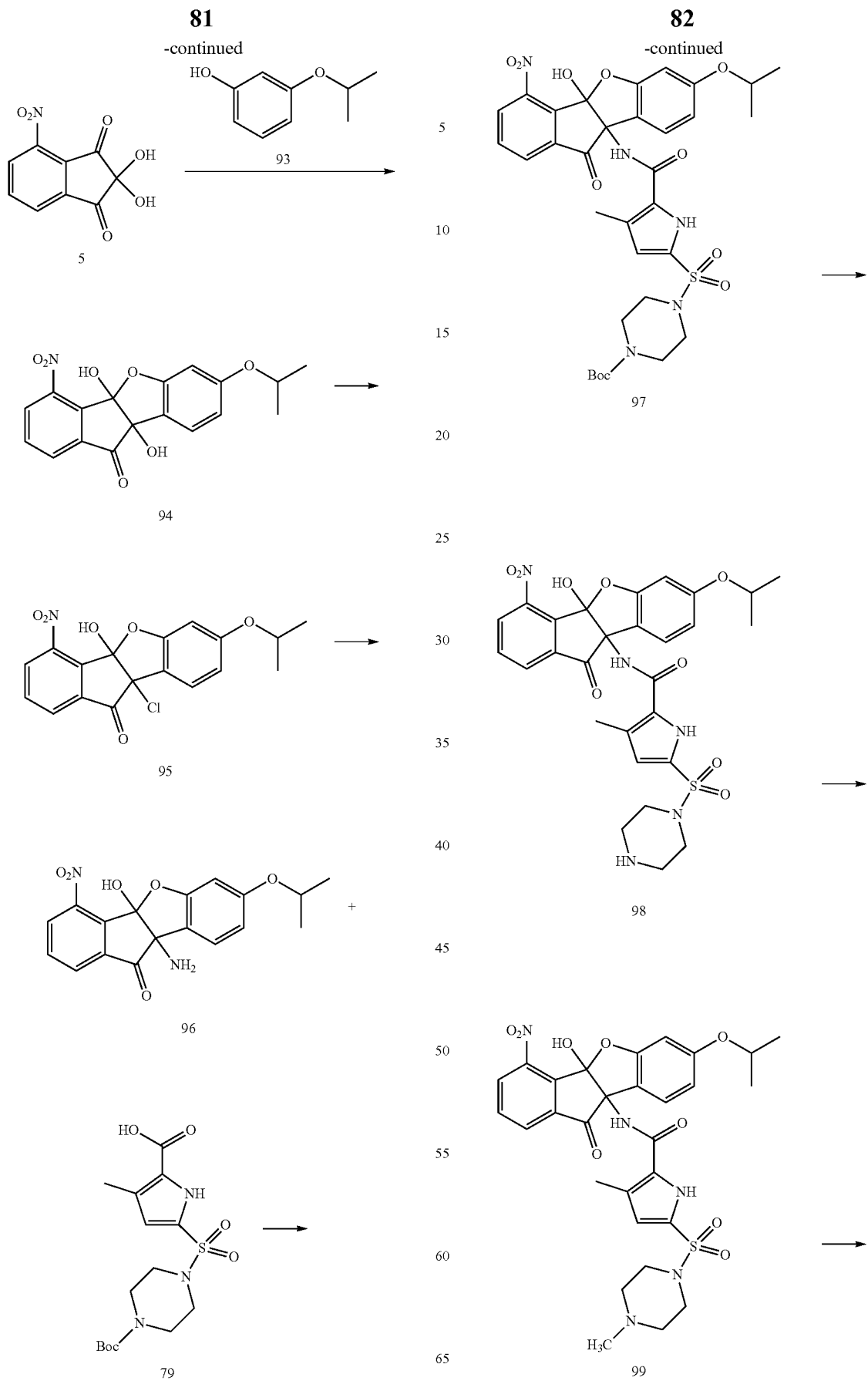

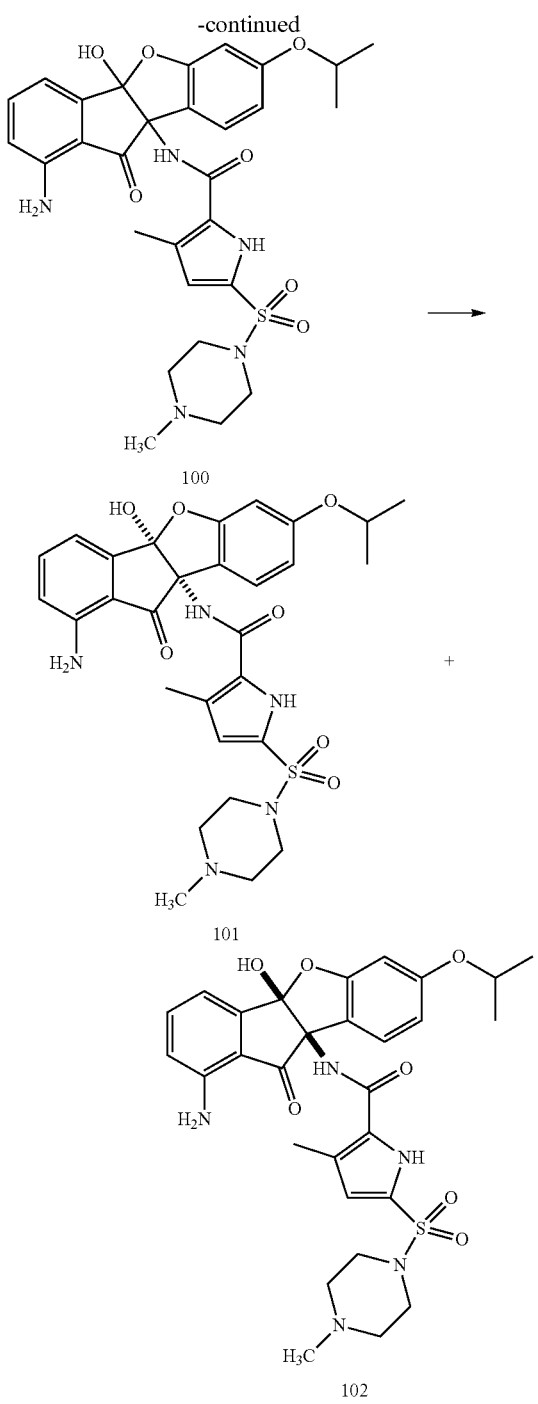

4b,9b-Dihydroxy-7-isopropoxy-4-nitro-4b,9b-dihydro-10H-indeno[1,2-b]benzofuran-10-one (94)

4-Nitro-1H-indene-1,3(2H)-dione 4 (10.0 g, 52.3 mmol) was taken in AcOH:dioxane (1:10, 105 mL, 0.5 M). This was charged with SeO$_2$ (12.77 g, 115.1 mmol) and refluxed for 5 hours at 105-110° C. The reaction mass was then filtered over CELITE under hot conditions and then the volatiles were concentrated off to get the crude 2,2-dihydroxy-4-nitro-1H-indene-1,3(2H)-dione 5. This crude was dissolved in acetic acid (106 mL) and to it was added 3-isopropoxyphenol 93 (8.1 g, 53 mmol). The resulting reaction mass was heated at 80° C. for 4 h. The reaction mass was cooled to rt and diluted with ethyl acetate. Reaction mass was filtered over CELITE bed and was washed with ethyl acetate. The solvent was evaporated to dryness The residue was purified over silica gel column chromatography (ethyl acetate: hexane) to give solid product.

9b-Chloro-4b-hydroxy-7-isopropoxy-4-nitro-4b,9b-dihydro-10H-indeno[1,2-b]benzofuran-10-one (95)

4b,9b-dihydroxy-7-isopropoxy-4-nitro-4b,9b-dihydro-10H-indeno[1,2-b]benzofuran-10-one 94 (5.4 g, 15 mmol) was dissolved in DCM (75 mL). To this was added oxalyl chloride (2.6 mL, 30 mmol), followed by drop wise addition of DMF (5.4 mL). The reaction mass was stirred at rt for 18 h. Reaction was diluted with DCM (300 mL) and organic layer was washed with water (200 mL×2) and with brine solution, and then dried over Na$_2$SO$_4$. The solvent was evaporated to get crude. Crude was purified over silica-gel column chromatography (ethyl acetate:hexane) to give solid product.

9b-amino-4b-hydroxy-7-isopropoxy-4-nitro-4b,9b-dihydro-10H-indeno[1,2-b]benzofuran-10-one (96)

This compound was prepared similar to compound 37 above.

Tert-butyl 4-((5-((4b-hydroxy-7-isopropoxy-4-nitro-10-oxo-4b,10-dihydro-9bH-indeno[1,2-b]benzofuran-9b-yl)carbamoyl)-4-methyl-1H-pyrrol-2-yl)sulfonyl)piperazine-1-carboxylate (97)

5-((4-(tert-butoxycarbonyl)piperazin-1-yl)sulfonyl)-3-methyl-1H-pyrrole-2-carboxylic acid 79 (240 mg 0.65 mmol) was dissolved in DMF (6.5 mL). The resulting solution was cooled to 0° C. and EDCI (187 mg, 0.975 mmol), HOBT (132 mg, 0.975 mmol) and DIPEA (0.283 mL, 1.625 mmol) were added at 0° C. The reaction mass was stirred for 30 min. Then 9b-amino-4b-hydroxy-7-isopropoxy-4-nitro-4b,9b-dihydro-10H-indeno[1,2-b]benzofuran-10-one 96 (232 mg, 0.65 mmol) was added and reaction was stirred at 30° C. for 15 h. The reaction mass was quenched with water (100 mL) and aqueous layer was extracted with ethyl acetate (3×100 mL). The combined organic layer was washed with water and with brine solution and was dried over Na$_2$SO$_4$. The solvent was evaporated under vacuum. The residue was purified over silica-gel column chromatography (methanol: DCM) to give solid product.

N-(4b-Hydroxy-7-isopropoxy-4-nitro-10-oxo-4b,10-dihydro-9bH-indeno[1,2-b]benzofuran-9b-yl)-3-methyl-5-(piperazin-1-ylsulfonyl)-1H-pyrrole-2-carboxamide (98)

tert-butyl 4-((5-((4b-hydroxy-7-isopropoxy-4-nitro-10-oxo-4b,10-dihydro-9bH-indeno[1,2-b]benzofuran-9b-yl)carbamoyl)-4-methyl-1H-pyrrol-2-yl)sulfonyl)piperazine-1-carboxylate 97 (145 mg, 0.2 mmol) was dissolved in DCM (4 mL). To this solution was added 4 M HCl in Dioxane (0.5 mL). The clear solution was stirred at rt for 15 h. DCM was evaporated under vacuum. The residue was dissolved in water (100 mL) and aqueous solution was neutralized with saturated solution of NaHCO$_3$. The aqueous layer was extracted with ethyl acetate (100 mL×2) and the combined organic layer was washed with water and with brine solution. Organic layer was dried over $Na_2SO_4$, and the solvent was evaporated to give crude solid product. Crude was used as such for next step without purification.

N-(4b-Hydroxy-7-isopropoxy-4-nitro-10-oxo-4b,10-dihydro-9bH-indeno[1,2-b]benzofuran-9b-yl)-3-methyl-S-((4-methylpiperazin-1-yl)sulfonyl)-1H-pyrrole-2-carboxamide (99)

N-(4b-hydroxy-7-isopropoxy-4-nitro-10-oxo-4b,10-dihydro-9bH-indeno[1,2-b]benzofuran-9b-yl)-3-methyl-5-(piperazin-1-ylsulfonyl)-1H-pyrrole-2-carboxamide 98 (115 mg, 0.188. mmol) dissolved in Gly acetic acid:MeCN (1:1) (5 mL). The solution was cooled to 0° C., and to this was added formaldehyde (0.161 mL, 1.88 mmol) followed by $NaBH_3CN$ (41 mg, 0.658 mmol). The resulting suspension was stirred at 0° C. to 5° C. for 1.5 h. Acetonitrile was evaporated and the residue quenched with water and aqueous layer was extracted with ethyl acetate (50 mL×3). The combined organic layer was washed with water, then brine solution. Organic layer was dried over $Na_2SO_4$, and the solvent was evaporated to give crude. Crude was purified over silica-gel column chromatography (Methanol:DCM) to give solid product.

N-(1-Amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (100)

N-(4b-hydroxy-7-isopropoxy-4-nitro-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide 99 (66 mg, 0.105 mmol) was dissolved in EtOH-water mixture (1:1, 3.5 mL), were added Fe powder (18 mg, 0.315 mmol) and Conc HCl (1 drop). The clear solution was refluxed at 90° C. for 3 h. The hot reaction mass was filtered through CELITE pad and was washed with ethyl acetate. Organic layer was evaporated under vacuum. The residue obtained was dissolved in ethyl acetate (200 mL) and was washed with water (75 mL×2) then with brine solution. The combined organic layer was dried over $Na_2SO_4$ and evaporated under vacuum to give crude. Crude was purified over silica-gel column chromatography (Methanol:DCM) to give solid product. $^1$H-NMR (300 MHz, CD3OD) δ 1.28 (dd, J=6 Hz, J=1.6 Hz, 6H), 2.29 (s, 6H), 2.51-2.54 (m, 4H), 3.06 (br, 4H), 4.51-4.59 (m, 1H) 6.38 (d, J=1.9 Hz, 1H), 6.54 (br, 2H), 6.79 (br, 1H), 7.04 (d, J=7.2 Hz, 1H), 7.34 (br, 1H), 7.47-7.52 (m, 1H). LCMS: 596.5[M+1]$^+$.

N-((4bR,9bR)-1-amino-4b-hydroxy-7-isopropoxy-10-oxo-4b,10-dihydro-9bH-indeno[1,2-b]benzofuran-9b-yl)-3-methyl-S-((4-methylpiperazin-1-yl)sulfonyl)-1H-pyrrole-2-carboxamide (101) and N-((4bS,9bS)-1-amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (102)

N-(1-Amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (100), (90 mg) as a racemate was purified by chiral chromatography using (IA column, HPLC=20 ml/min, Heptane/EtOH=30/70, 2562 psi) to give 37.5 mg of N-((4bR,9bR)-1-amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide(101) as (peak 2, tR 16.32 min.), 1H NMR (METHANOL-d4) δ: 7.43-7.53 (m, 1H), 7.39 (br d, J=12.3 Hz, 1H), 7.02 (br s, 1H), 6.72 (br s, 1H), 6.55 (s, 2H), 6.36 (br s, 1H), 4.54 (dt, J=12.0, 5.9 Hz, 1H), 3.11 (br s, 4H), 2.75 (br s, 4H), 2.45 (br s, 3H), 2.29 (s, 3H), 1.25-1.28 (m, 6H); LCMS: 596.6 [M+H]$^+$ and 36.4 mg of N-((4bS,9bS)-1-amino-4b-hydroxy-7-isopropoxy-10-oxo-4b,10-dihydro-9bH-indeno[1,2-b]benzofuran-9b-yl)-3-methyl-5-((4-methylpiperazin-1-yl)sulfonyl)-1H-pyrrole-2-carboxamide (102) as (peak 1, tR 5.70 min.); 1H NMR (METHANOL-d4) δ: 7.48 (br s, 1H), 7.24-7.42 (m, 1H), 7.03 (br d, J=5.9 Hz, 1H), 6.67-6.82 (m, 1H), 6.53 (s, 2H), 6.36 (br s, 1H), 4.54 (dt, J=11.9, 6.1 Hz, 1H), 3.07 (br s, 4H), 2.59 (br s, 4H), 2.33 (s, 3H), 2.28 (s, 3H), 1.24-1.31 (m, 6H); LCMS: 596.0 [M+H]$^+$.

Example 21: N-(1-amino-4b-hydroxy-7-((1S,2R)-2-methylcyclopropyl)-10-oxo-4b,10-dihydro-9bH-indeno[1,2-b]benzofuran-9b-yl)-3-methyl-S-(methylsulfonyl)-1H-pyrrole-2-carboxamide

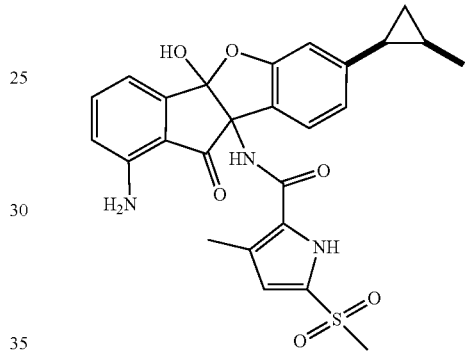

Scheme-19B

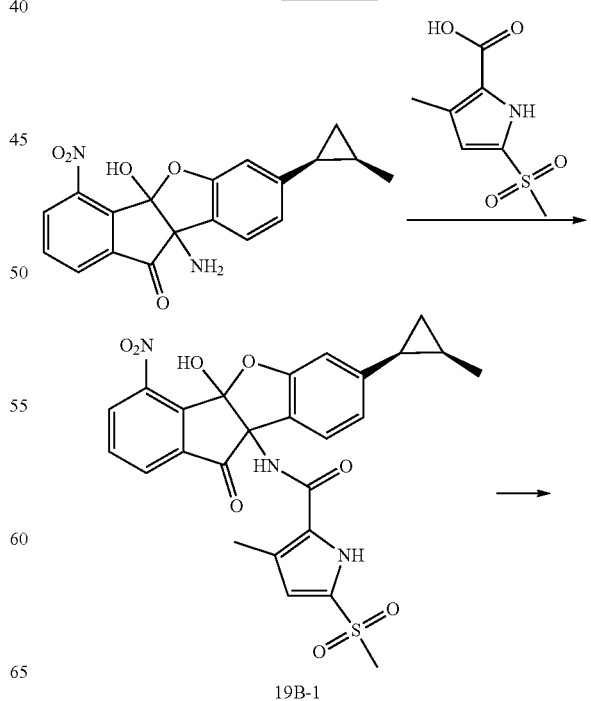

19B-1

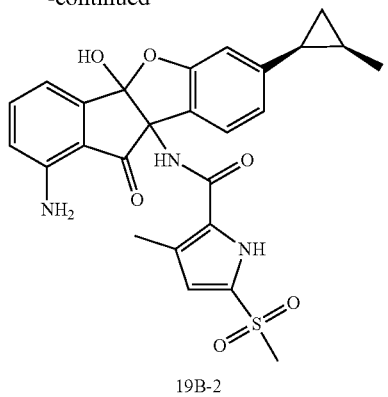

19B-2

N-[9-hydroxy-5-[(1S,2R)-2-methylcyclopropyl]-11-nitro-16-oxo-8-oxatetracyclo[7.7.0.0^[2,7].0^10,15]]hexadeca-2(7),3,5,10,12,14-hexaen-1-yl]-5-methanesulfonyl-3-methyl-1H-pyrrole-2-carboxamide (19B-1)

Into a 50-mL round-bottom flask, was placed 5-methanesulfonyl-3-methyl-1H-pyrrole-2-carboxylic acid (259 mg, 1.27 mmol, 1.50 equiv), HOBt (172 mg, 1.27 mmol, 1.50 equiv), EDCI (243 mg, 1.27 mmol, 1.50 equiv), N,N-dimethylformamide (5 mL), 1-amino-9-hydroxy-5-[(1S, 2R)-2-methylcyclopropyl]-11-nitro-8-oxatetracyclo[7.7.0.0^[2,7].0^10,15]]hexadeca-2(7),3,5,10,12,14-hexaen-16-one (300 mg, 0.85 mmol, 1.00 equiv) and triethylamine (257 mg, 2.54 mmol, 3.00 equiv). The resulting solution was stirred at room temperature overnight. The resulting mixture was concentrated under vacuum. The residue was applied onto a silica gel column with dichloromethane/methanol (25/1). This resulted in 250 mg (55%) of N-[9-hydroxy-5-[(1S,2R)-2-methylcyclopropyl]-11-nitro-16-oxo-8-oxatetracyclo[7.7.0.0^[2,7].0^10,15]]hexadeca-2(7),3,5,10,12,14-hexaen-1-yl]-5-methanesulfonyl-3-methyl-1H-pyrrole-2-carboxamide (19B-1) as a yellow solid.

N-[14-amino-9-hydroxy-5-[(1 S,2R)-2-methylcyclopropyl]-16-oxo-8-oxatetracyclo[7.7.0.0^[2,7].0^10,15]]hexadeca-2(7),3,5,10,12,14-hexaen-1-yl]-5-methanesulfonyl-3-methyl-1H-pyrrole-2-carboxamide (19B-2)

Into a 50-mL round-bottom flask, was placed N-[9-hydroxy-5-[(1S,2R)-2-methylcyclopropyl]-11-nitro-16-oxo-8-oxatetracyclo[7.7.0.0^[2,7].0^10,15]]hexadeca-2(7),3,5,10,12,14-hexaen-1-yl]-5-methanesulfonyl-3-methyl-1H-pyrrole-2-carboxamide (19B-1) (250 mg, 0.47 mmol, 1.00 equiv), Fe (78 mg, 3.00 equiv), ethanol (10 mL), water (1 mL), hydrogen chloride (0.1 mL). The resulting solution was stirred at 85° C. for 2 h in an oil bath. The resulting mixture was concentrated under vacuum. The residue was applied onto a silica gel column with dichloromethane/methanol (20/1). This resulted in 108 mg (46%) of N-(1-amino-4b-hydroxy-7-((1S,2R)-2-methylcyclopropyl)-10-oxo-4b,10-dihydro-9bH-indeno[1,2-b]benzofuran-9b-yl)-3-methyl-5-(methylsulfonyl)-1H-pyrrole-2-carboxamide (19B-2).

$^1$H NMR (300 MHz, CD$_3$OD) δ 7.54-7.43 (m, 1H), 7.41-7.35 (m, 1H), 7.08-7.00 (m, 1H), 6.90-6.80 (m, 1H), 6.80-6.75 (m, 1H), 6.69-6.60 (m, 2H), 3.13 (s, 3H), 2.29 (s, 3H), 2.12-1.98 (m, 1H), 1.23-1.05 (m, 1H), 1.03-0.88 (m, 1H), 0.81-0.72 (m, 3H), 0.64-0.52 (m, 1H); LC-MS (ES, m/z): [M+H]$^+$ 508.0 (stereochemistry on the cyclopropane is relative with absolute not known)

Examples 22, 29, and 30: N-(1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide (29), N-((4bR,9bR)-1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide (22), and N-((4bS,9bS)-1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide (30)

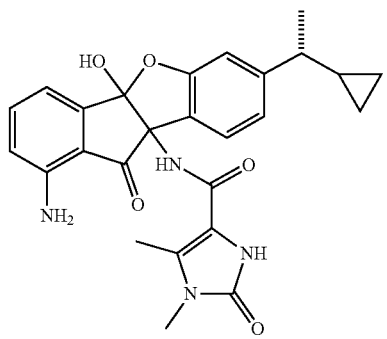 [SMILES: Cc1c(C(=O)NC23C(=O)c4c(N)cccc4C2(O)Oc2cc([C@H](C)C4CC4)ccc23)[nH]c(=O)n1C]

Scheme-19C

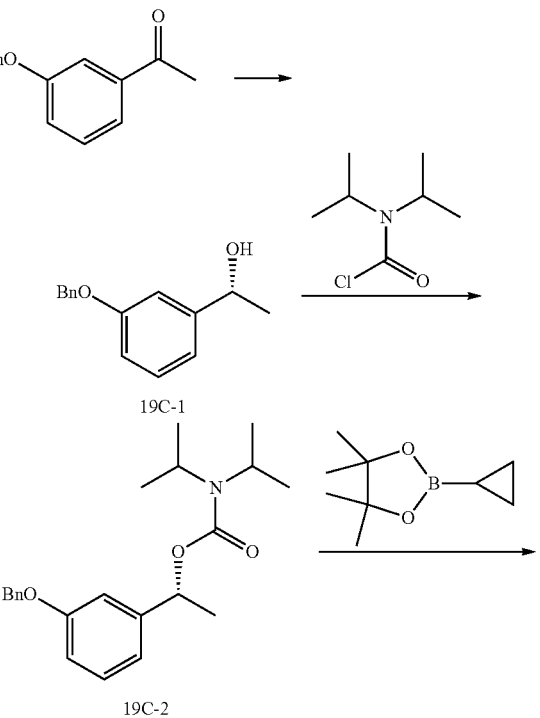

19C-1

19C-2

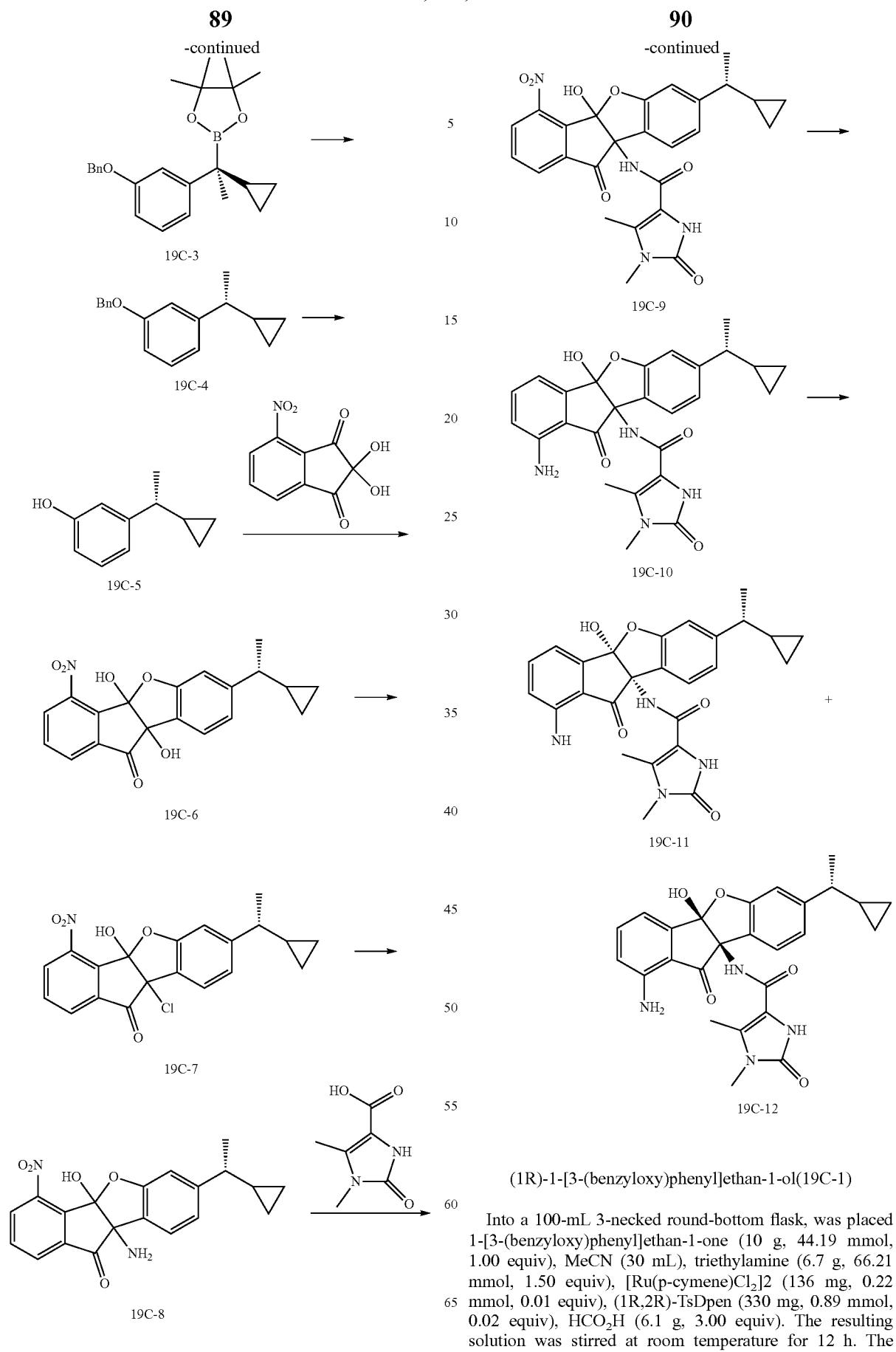
(1R)-1-[3-(benzyloxy)phenyl]ethan-1-ol(19C-1)
Into a 100-mL 3-necked round-bottom flask, was placed 1-[3-(benzyloxy)phenyl]ethan-1-one (10 g, 44.19 mmol, 1.00 equiv), MeCN (30 mL), triethylamine (6.7 g, 66.21 mmol, 1.50 equiv), [Ru(p-cymene)Cl$_2$]2 (136 mg, 0.22 mmol, 0.01 equiv), (1R,2R)-TsDpen (330 mg, 0.89 mmol, 0.02 equiv), HCO$_2$H (6.1 g, 3.00 equiv). The resulting solution was stirred at room temperature for 12 h. The resulting mixture was concentrated under vacuum. The residue was applied onto a silica gel column with ethyl acetate/petroleum ether (20/80). This resulted in 4 g (40%) of (1R)-1-[3-(benzyloxy)phenyl]ethan-1-ol as a colorless oil.

(1R)-1-[3-(benzyloxy)phenyl]ethyl N,N-bis(propan-2-yl)carbamate (19C-2)

Into a 50-mL round-bottom flask, was placed (1R)-1-[3-(benzyloxy)phenyl]ethan-1-ol (3.5 g, 15.33 mmol, 1.00 equiv), CH$_3$CN (15 mL), N,N-bis(propan-2-yl)carbamoyl chloride (2.9 g, 17.72 mmol, 1.15 equiv) and TEA (1.9 g, 18.78 mmol, 1.20 equiv). The resulting solution was stirred at 80° C. for 12 h. The resulting mixture was concentrated under vacuum. The residue was applied onto a silica gel column with ethyl acetate/petroleum ether (15/85). This resulted in 5.3 g (97%) of (1R)-1-[3-(benzyloxy)phenyl]ethyl N,N-bis(propan-2-yl)carbamate as a yellow oil.

2-[(1R)-1-[3-(benzyloxy)phenyl]-1-cyclopropylethyl]-4,4,5,5-tetramethyl-1,3,2-dioxaborolane (19C-3)

Into a 500-mL 3-necked round-bottom flask, was placed (1R)-1-[3-(benzyloxy)phenyl]ethyl N,N-bis(propan-2-yl) carbamate (5.3 g, 14.91 mmol, 1.00 equiv), ether (100 mL) and 2-cyclopropyl-4,4,5,5-tetramethyl-1,3,2-dioxaborolane (5 g, 29.75 mmol, 2.00 equiv). Then LDA (14.9 mL, 2 mol/L, 2.00 equiv) was added dropwise at −20° C. The resulting solution was stirred at room temperature for 12 h. The reaction was then quenched by the addition of methanol. The resulting mixture was concentrated under vacuum. The residue was applied onto a silica gel column with ethyl acetate/petroleum ether (15/85). This resulted in 4.1 g (73%) of 2-[(1R)-1-[3-(benzyloxy)phenyl]-1-cyclopropylethyl]-4,4,5,5-tetramethyl-1,3,2-dioxaborolane as a yellow oil.

1-(benzyloxy)-3-[(1R)-1-cyclopropylethyl]benzene (19C-4)

Into a 100-mL round-bottom flask, was placed 2-[(1R)-1-[3-(benzyloxy)phenyl]-1-cyclopropylethyl]-4,4,5,5-tetramethyl-1,3,2-dioxaborolane (4 g, 10.57 mmol, 1.00 equiv), n-pentane (50 mL) and TBAF-3H$_2$O (5 g, 15.87 mmol, 1.50 equiv). The resulting solution was stirred at 45° C. for 12 h. The resulting mixture was concentrated under vacuum. The residue was applied onto a silica gel column with ethyl acetate/petroleum ether (10/90). This resulted in 2.4 g (90%) of 1-(benzyloxy)-3-[(1R)-1-cyclopropylethyl] benzene as a yellow oil.

3-[(1R)-1-Cyclopropylethyl]phenol (19C-5)

Into a 100-mL round-bottom flask, was placed 1-(benzyloxy)-3-[(1R)-1-cyclopropylethyl]benzene (2.1 g, 8.32 mmol, 1.00 equiv), methanol (20 mL) and Palladium carbon (200 mg). The resulting solution was stirred at room temperature for 2 h under H$_2$ atmosphere. The solids were filtered out. The resulting mixture was concentrated under vacuum. The residue was applied onto a silica gel column with ethyl acetate/petroleum ether (15/85). This resulted in 1.3 g (96%) of 3-[(1R)-1-cyclopropylethyl]phenol as a colorless oil.

5-[(1R)-1-Cyclopropylethyl]-1,9-dihydroxy-11-nitro-8-oxatetracyclo[7.7.0.0ˆ[2,7].0ˆ[10,15]]hexadeca-2(7),3,5,10,12,14-hexaen-16-one (19C-6)

Into a 100-mL round-bottom flask, was placed 3-[(1R)-1-cyclopropylethyl]phenol (1.3 g, 8.01 mmol, 1.00 equiv), acetic acid (20 mL) and 2,2-dihydroxy-4-nitro-2,3-dihydro-1H-indene-1,3-dione (1.8 g, 8.07 mmol, 1.00 equiv). The resulting solution was stirred at 120° C. for 2 h. The resulting mixture was concentrated under vacuum. The residue was applied onto a silica gel column with ethyl acetate/petroleum ether (30/70). This resulted in 2.2 g (75%) of 5-[(1R)-1-cyclopropylethyl]-1,9-dihydroxy-11-nitro-8-oxatetracyclo[7.7.0.0ˆ[2,7].0ˆ[10,15]]hexadeca-2(7),3,5,10,12,14-hexaen-16-one as a yellow solid.

1-Chloro-5-[(1R)-1-cyclopropylethyl]-9-hydroxy-11-nitro-8-oxatetracyclo[7.7.0.0ˆ[2,7].0ˆ[10,15]] hexadeca-2(7),3,5,10,12,14-hexaen-16-one (19C-7)

Into a 100-mL round-bottom flask, was placed 5-[(1R)-1-cyclopropylethyl]-1,9-dihydroxy-11-nitro-8-oxatetracyclo[7.7.0.0ˆ[2,7].0ˆ[10,15]]hexadeca-2(7),3,5,10,12,14-hexaen-16-one (4.1 g, 11.16 mmol, 1.00 equiv), dichloromethane (20 mL), N,N-dimethylformamide (2 mL) and oxalyl chloride (16.7 mL, 3.00 equiv). The resulting solution was stirred at 45° C. for 2 h. The reaction was then quenched by the addition of water/ice. The resulting solution was extracted with dichloromethane. The organic layers were combined and concentrated under vacuum. This resulted in 4.5 g (crude) of 1-chloro-5-[(1R)-1-cyclopropylethyl]-9-hydroxy-11-nitro-8-oxatetracyclo[7.7.0.0ˆ[2,7].0ˆ[10,15]]hexadeca-2(7),3,5,10,12,14-hexaen-16-one as a brown oil.

1-Amino-5-[(1R)-1-cyclopropylethyl]-9-hydroxy-11-nitro-8-oxatetracyclo[7.7.0.0ˆ[2,7].0ˆ[10,15]] hexadeca-2(7),3,5,10,12,14-hexaen-16-one (19C-8)

Into a 250-mL round-bottom flask, was placed 1-chloro-5-[(1R)-1-cyclopropylethyl]-9-hydroxy-11-nitro-8-oxatetracyclo[7.7.0.0ˆ[2,7].0ˆ[10,15]]hexadeca-2(7),3,5,10,12,14-hexaen-16-one (4.5 g, 11.66 mmol, 1.00 equiv) in THF (30 mL) was added NH$_3$ in IPA (17.5 mL, 3.00 equiv) dropwise at −50° C. The resulting solution was stirred at −50° C. for 2 h. The resulting mixture was concentrated under vacuum. The residue was applied onto a silica gel column with ethyl acetate/petroleum ether (35/65). This resulted in 3.5 g (82%) of 1-amino-5-[(1R)-1-cyclopropylethyl]-9-hydroxy-11-nitro-8-oxatetracyclo[7.7.0.0ˆ[2,7].0ˆ[10,15]]hexadeca-2(7), 3,5,10,12,14-hexaen-16-one as a yellow solid.

N-[5-[(1R)-1-Cyclopropylethyl]-9-hydroxy-11-nitro-16-oxo-8-oxatetracyclo[7.7.0.0ˆ[2,7].0ˆ[10,15]]hexadeca-2(7),3,5,10,12,14-hexaen-1-yl]-1,5-dimethyl-2-oxo-2,3-dihydro-1H-imidazole-4-carboxamide (19C-9)

Into a 50-mL round-bottom flask, was placed 1,5-dimethyl-2-oxo-2,3-dihydro-1H-imidazole-4-carboxylic acid (1.3 g, 8.33 mmol, 1.20 equiv), EDCI (1.6 g, 8.35 mmol, 1.20 equiv), HOBt (1.1 g, 8.14 mmol, 1.20 equiv), N,N-dimethylformamide (5 mL), 1-amino-5-[(1R)-1-cyclopropylethyl]-9-hydroxy-11-nitro-8-oxatetracyclo[7.7.0.0ˆ [2,7].0ˆ[10,15]]hexadeca-2(7),3,5,10,12,14-hexaen-16-one (2.5 g, 6.82 mmol, 1.00 equiv) and triethylamine (2.3 mL, 3.00 equiv). The resulting solution was stirred at room temperature for 12 h. The resulting mixture was concentrated under vacuum. The residue was applied onto a silica gel column with dichloromethane/methanol (20/1). This resulted in 1.4 g (41%) of N-[5-[(1R)-1-cyclopropylethyl]-9-hydroxy-11-nitro-16-oxo-8-oxatetracyclo[7.7.0.0^[2,7].0^[10,15]]hexadeca-2(7),3,5,10,12,14-hexaen-1-yl]-1,5-dimethyl-2-oxo-2,3-dihydro-1H-imidazole-4-carboxamide as a yellow solid.

N-(1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide (19C-10)

Into a 25-mL round-bottom flask, was placed N-[5-[(1R)-1-cyclopropylethyl]-9-hydroxy-11-nitro-16-oxo-8-oxatetracyclo[7.7.0.0^[2,7].0^[10,15]]hexadeca-2(7),3,5,10,12,14-hexaen-1-yl]-1,5-dimethyl-2-oxo-2,3-dihydro-1H-imidazole-4-carboxamide (120 g, 237.86 mmol, 1.00 equiv), ethanol (10 mL), iron (40 mg, 0.72 mmol, 3.00 equiv), water (1 mL), conc. hydrogen chloride (0.01 mL). The resulting solution was stirred at 85° C. for 2 h. The resulting mixture was concentrated under vacuum. The residue was purified by flash chromatograph with DCM/MeOH (25/1). This resulted in 100 mg of N-(1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide (19C-10, Example 29).

$^1$H NMR (300 MHz, CD$_3$OD) 7.55-7.39 (m, 2H), 7.05-7.01 (m, 1H), 6.93-6.70 (m, 3H), 3.21 (s, 3H), 2.35 (s, 3H), 2.04-1.84 (m, 1H), 1.30-1.27 (m, 3H), 0.94-0.89 (m, 1H), 0.57-0.52 (m, 1H), 0.38-0.34 (m, 1H), 0.22-0.16 (m, 1H), 0.09-0.02 (m, 1H); LCMS: (ES, m/z):[M+H]$^+$ 475.2

N-((4bR,9bR)-1-amino-7-((R)-1-cyclopropylethyl)-4b-hydroxy-10-oxo-9b,10-dihydro-4bH-indeno[1,2-b]benzofuran-9b-yl)-1,5-dimethyl-2-oxo-2,3-dihydro-1H-imidazole-4-carboxamide (19C-11, Example 22) and N-((4bS,9bS)-1-amino-7-((R)-1-cyclopropylethyl)-4b-hydroxy-10-oxo-9b,10-dihydro-4bH-indeno[1,2-b]benzofuran-9b-yl)-1,5-dimethyl-2-oxo-2,3-dihydro-1H-imidazole-4-carboxamide (19C-12, Example 30)

N-(1-amino-7-((R)-1-cyclopropylethyl)-4b-hydroxy-10-oxo-4b,10-dihydro-9bH-indeno[1,2-b]benzofuran-9b-yl)-1,5-dimethyl-2-oxo-2,3-dihydro-1H-imidazole-4-carboxamide (19C-10), (103.9 mg) as a racemate was purified by chiral chromatography using (IA column, HPLC=20 ml/min, Heptane/IPA=60/40) to give 42.8 mg of N-((4bR,9bR)-1-amino-7-((R)-1-cyclopropylethyl)-4b-hydroxy-10-oxo-9b,10-dihydro-4bH-indeno[1,2-b]benzofuran-9b-yl)-1,5-dimethyl-2-oxo-2,3-dihydro-1H-imidazole-4-carboxamide (19C-11) as (peak 1, tR 7.76 min.), 1H NMR (400 MHz, METHANOL-d4) δ: 8.32-8.47 (m, 2H), 7.97 (br d, J=7.2 Hz, 1H), 7.86 (br d, J=7.8 Hz, 1H), 7.62-7.71 (m, 2H), 4.17 (s, 3H), 3.31 (s, 3H), 2.80-2.93 (m, 1H), 2.24 (d, J=7.0 Hz, 3H), 1.81-1.90 (m, 1H), 1.46-1.55 (m, 1H), 1.28-1.36 (m, 1H), 1.15 (dq, J=9.4, 4.7 Hz, 1H), 1.04 (dq, J=9.5, 4.8 Hz, 1H); LCMS: 475.2 [M+H]$^+$ and 35.8 mg of N-((4bS,9bS)-1-amino-7-((R)-1-cyclopropylethyl)-4b-hydroxy-10-oxo-9b,10-dihydro-4bH-indeno[1,2-b]benzofuran-9b-yl)-1,5-dimethyl-2-oxo-2,3-dihydro-1H-imidazole-4-carboxamide (19C-12) as (peak 2, tR 16.43 min.); 1H NMR (500 MHz, METHANOL-d4) δ: 7.38-7.51 (m, 2H), 7.01 (br d, J=6.9 Hz, 1H), 6.85-6.94 (m, 1H), 6.70 (br s, 2H), 3.20 (s, 3H), 2.34 (s, 3H), 1.86-1.94 (m, 1H), 1.27 (d, J=7.1 Hz, 3H), 0.85-0.93 (m, 1H), 0.50-0.55 (m, 1H), 0.31-0.38 (m, 1H), 0.18 (dq, J=9.8, 4.8 Hz, 1H), 0.06 (dq, J=9.4, 4.8 Hz, 1H); LCMS: 475.2 [M+H]$^+$.

Example 23: N-(1-amino-7-(sec-butyl)-4b-hydroxy-10-oxo-4b,10-dihydro-9bH-indeno[1,2-b]benzofuran-9b-yl)-3-methyl-4-(methylsulfonyl)-1H-pyrrole-2-carboxamide

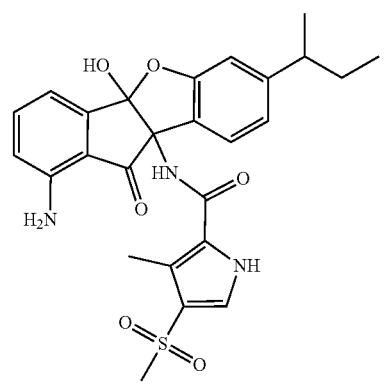 [SMILES: CCC(C)c1ccc2c(c1)OC1(O)c3cccc(N)c3C(=O)C21NC(=O)c1[nH]cc(S(C)(=O)=O)c1C]

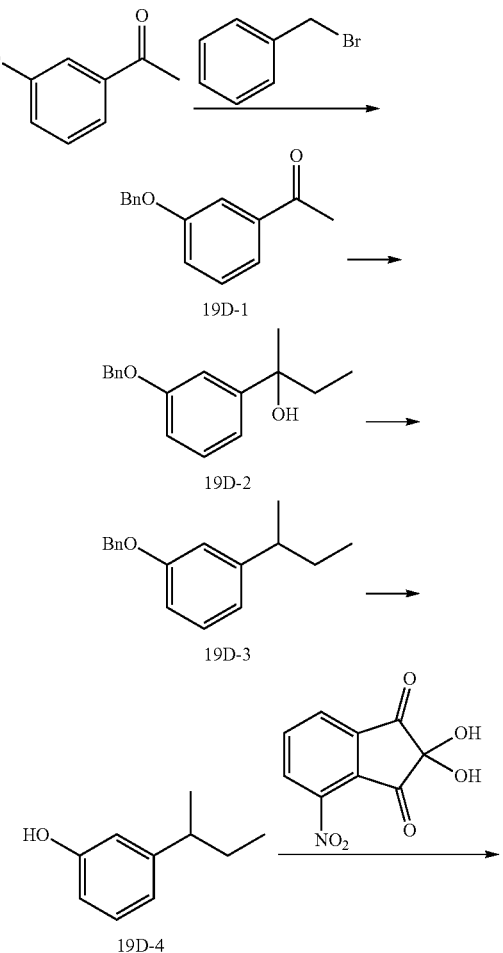

Scheme-19D

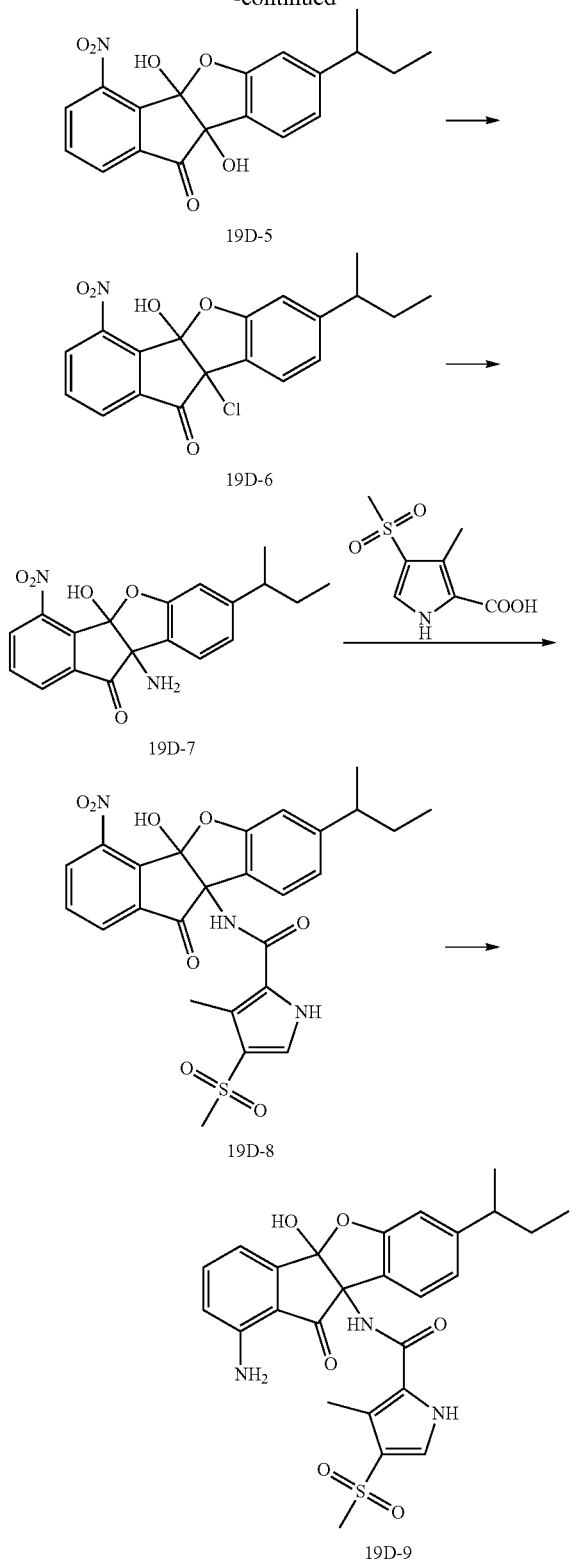

1-[3-(Benzyloxy)phenyl]ethan-1-one (19D-1)

Into a 500-mL round-bottom flask, was placed a solution of 1-(3-hydroxyphenyl)ethan-1-one (20 g, 146.90 mmol, 1.00 equiv), CH₃CN (180 mL), (bromomethyl)benzene (20 mL, 1.20 equiv) and potassium carbonate (40.8 g, 2.00 equiv). The resulting solution was stirred at 80° C. for 2 h in an oil bath. The solids were filtered out. The reaction was concentrated under vacuum. The residue was applied onto a silica gel column with ethyl acetate/petroleum ether (1:10). This resulted in 30.5 g (92%) of 1-[3-(benzyloxy)phenyl]ethan-1-one as a yellow oil.

2-[3-(Benzyloxy)phenyl]butan-2-ol (19D-2)

Into a 250-mL round-bottom flask, was placed a solution of 1-[3-(benzyloxy)phenyl]ethan-1-one (5 g, 22.10 mmol, 1.00 equiv) and THF (100 mL) Then bromo(ethyl)magnesium (22 mL, 3.00 equiv) was added at 0° C. The resulting solution was stirred at room temperature overnight. The reaction was then quenched by the addition of 300 mL of water. The resulting solution was extracted with 3×200 mL of chloromethane. The organic layers were combined and concentrated under vacuum. The residue was applied onto a silica gel column with ethyl acetate/petroleum ether (1/1). This resulted in 3.1 g (55%) of 2-[3-(benzyloxy)phenyl]butan-2-ol as colorless oil.

1-(Benzyloxy)-3-(butan-2-yl)benzene (19D-3)

Into a 250-mL 3-necked round-bottom flask purged and maintained with an inert atmosphere of nitrogen, was placed a solution of 2-[3-(benzyloxy)phenyl]butan-2-ol (6.2 g, 24.19 mmol, 1.00 equiv) in dichloromethane (120 mL) Then triethylsilane (18.2 mL, 5.00 equiv) and trifluoroacetic acid (18.05 mL, 1.00 equiv) were added. The resulting solution was stirred at room temperature overnight. The reaction was then quenched by the addition of 100 mL of water and extracted with 3×50 mL of dichloromethane. The organic layers were combined and concentrated under vacuum. The residue was applied onto a silica gel column with petroleum ether (100%). This resulted in 3.8 g (65%) of 1-(benzyloxy)-3-(butan-2-yl)benzene as yellow oil.

3-(Butan-2-yl)phenol (19D-4)

Into a 100-mL round-bottom flask, was placed a solution of 1-(benzyloxy)-3-(butan-2-yl)benzene (3.8 g, 15.81 mmol, 1.00 equiv) in methanol (38 mL) and Palladium carbon (380 g). The resulting solution was stirred at room temperature for 2 h under H₂. The solids were filtered out. The resulting mixture was concentrated under vacuum. The residue was applied onto a silica gel column with ethyl acetate/petroleum ether (1/20). This resulted in 2.0 g (84%) of 3-(butan-2-yl)phenol as a yellow solid.

5-(Butan-2-yl)-1,9-dihydroxy-11-nitro-8-oxatetracyclo[7.7.0.0^[2,7].0^[10,15]]hexadeca-2(7),3,5,10,12,14-hexaen-16-one (19D-5)

Into a 100-mL round-bottom flask, was placed a solution of 3-(butan-2-yl)phenol (1.5 g, 9.99 mmol, 1.00 equiv) in acetic acid (35 mL) and 2,2-dihydroxy-4-nitro-2,3-dihydro-1H-indene-1,3-dione (1.85 g, 8.29 mmol, 1.00 equiv). The resulting solution was stirred at 120° C. for 2 h in an oil bath. The resulting mixture was concentrated under vacuum. The residue was applied onto a silica gel column with ethyl acetate/petroleum ether (1/2). This resulted in 1.37 g (39%) of 5-(butan-2-yl)-1,9-dihydroxy-11-nitro-8-oxatetracyclo

[7.7.0.0^[2,7].0^[10,15]]hexadeca-2(7),3,5,10,12,14-hexaen-16-one as a yellow solid.

5-(Butan-2-yl)-1-chloro-9-hydroxy-11-nitro-8-oxatetracyclo[7.7.0.0^[2,7].0^[10,15]]hexadeca-2(7),3,5,10,12,14-hexaen-16-one (19D-6)

Into a 50-mL round-bottom flask, was placed a solution of 5-(butan-2-yl)-1,9-dihydroxy-11-nitro-8-oxatetracyclo [7.7.0.0^[2,7].0^[10,15]]hexadeca-2(7),3,5,10,12,14-hexaen-16-one (1.37 g, 3.86 mmol, 1.00 equiv) in dichloromethane (20 mL), Oxalyl Chloride (1.1 mL, 3.00 equiv) and N,N-dimethylformamide (2 mL). The resulting solution was stirred at 40° C. for 2 h in an oil bath. The reaction was then quenched by the addition of 50 mL of water/ice. The resulting solution was extracted with 3×100 mL of dichloromethane. The organic layers were combined and concentrated under vacuum. The residue was applied onto a silica gel column with ethyl acetate/petroleum ether (1/5). This resulted in 1.2 g (83%) of 5-(butan-2-yl)-1-chloro-9-hydroxy-11-nitro-8-oxatetracyclo[7.7.0.0^[2,7].0^[10,15]] hexadeca-2(7),3,5,10,12,14-hexaen-16-one as a brown oil.

1-Amino-5-(butan-2-yl)-9-hydroxy-11-nitro-8-oxatetracyclo[7.7.0.0^[2,7].0^[10,15]]hexadeca-2(7),3,5,10,12,14-hexaen-16-one (19D-7)

Into a 50-mL round-bottom flask, was placed a solution of 5-(butan-2-yl)-1-chloro-9-hydroxy-11-nitro-8-oxatetracyclo [7.7.0.0^[2,7].0^[10,15]]hexadeca-2(7),3,5,10,12,14-hexaen-16-one (1.2 g, 3.21 mmol, 1.00 equiv) in tetrahydrofuran (18 mL). This was followed by the addition of $NH_3$ in IPA (4.8 mL, 3.00 equiv) at −50° C. The resulting solution was stirred at −40-10° C. for 1.5 h. The resulting mixture was concentrated under vacuum. The residue was applied onto a silica gel column with ethyl acetate/petroleum ether (1/2). This resulted in 630 mg (55%) of 1-amino-5-(butan-2-yl)-9-hydroxy-11-nitro-8-oxatetracyclo[7.7.0.0^[2,7].0^[10,15]]hexadeca-2(7),3,5,10,12,14-hexaen-16-one as a yellow solid.

N-[5-(Butan-2-yl)-9-hydroxy-11-nitro-16-oxo-8-oxatetracyclo[7.7.0.0^[2,7].0^[10,15]]hexadeca-2(7),3,5,10,12,14-hexaen-1-yl]-4-methanesulfonyl-3-methyl-1H-pyrrole-2-carboxamide (19D-8)

Into a 25-mL round-bottom flask, was placed a solution of 4-methanesulfonyl-3-methyl-1H-pyrrole-2-carboxylic acid (122 mg, 0.60 mmol, 1.50 equiv) in N,N-dimethylformamide (2 mL), EDCI (115 mg, 0.60 mmol, 1.50 equiv), HOBt (81 mg, 0.60 mmol, 1.50 equiv), 1-amino-5-(butan-2-yl)-9-hydroxy-11-nitro-8-oxatetracyclo[7.7.0.0^[2,7].0^[10,15]] hexadeca-2(7),3,5,10,12,14-hexaen-16-one (150 mg, 0.42 mmol, 1.00 equiv) and triethylamine (121 mg, 1.20 mmol, 2.50 equiv). The resulting solution was stirred at room temperature overnight. The resulting mixture was concentrated under vacuum. The residue was applied onto a silica gel column with dichloromethane/methanol (25/1). This resulted in 140 mg (61%) of N-[5-(butan-2-yl)-9-hydroxy-11-nitro-16-oxo-8-oxatetracyclo[7.7.0.0^[2,7].0^[10,15]] hexadeca-2(7),3,5,10,12,14-hexaen-1-yl]-4-methanesulfonyl-3-methyl-1H-pyrrole-2-carboxamide as a yellow solid.

N-[14-Amino-5-(butan-2-yl)-9-hydroxy-16-oxo-8-oxatetracyclo [7.7.0.0^[2,7].0^[10,15]]hexadeca-2(7),3,5,10,12,14-hexaen-1-yl]-4-methanesulfonyl-3-methyl-1H-pyrrole-2-carboxamide (19D-9)

Into a 50-mL round-bottom flask, was placed a solution of N-[5-(butan-2-yl)-9-hydroxy-11-nitro-16-oxo-8-oxatetracyclo[7.7.0.0^[2,7].0^[10,15]]hexadeca-2(7),3,5,10,12,14-hexaen-1-yl]-4-methanesulfonyl-3-methyl-1H-pyrrole-2-carboxamide (140 mg, 0.26 mmol, 1.00 equiv) in ethanol (5 mL), water (0.5 mL), Fe (40.32 mg, 3.00 equiv) and hydrogen chloride (0.05 mL). The resulting solution was stirred at 85° C. for 2 h in an oil bath. The solids were filtered out. The resulting mixture was concentrated under vacuum. The residue was applied onto a silica gel column with dichloromethane/methanol (20/1). This resulted in 22.1 mg (17%) of N-(1-amino-7(sec-butyl)-4b-hydroxy-10-oxo-4b,10-dihydro-9bH-indeno [1,2-b] benzofuran-9b-yl)-3-methyl-4-(methylsulfonyl)-1H-pyrrole-2-carboxamide (19D-9).

$^1$HNMR (300 MHZ, $CD_3OD$) δ 7.61-7.35 (m, 3H), 7.18-7.05 (m, 1H), 6.90-6.63 (m, 3H), 3.01 (s, 3H), 2.62-2.40 (m, 4H), 1.65-1.50 (m, 2H), 1.19 (d, J=6.9 Hz, 3H), 0.90-0.78 (m, 3H); LC-MS: (ES, m/z): [M+H]$^+$: 510.1

Example 24: N-(1-amino-4b-hydroxy-7-((1S,2R)-2-methylcyclopropyl)-10-oxo-4b,10-dihydro-9bH-indeno[1,2-b]benzofuran-9b-yl)-3-methyl-5-((4-methylpiperazin-1-yl) sulfonyl)-1H-pyrrole-2-carboxamide

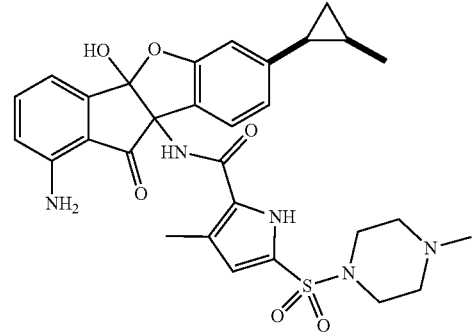 [SMILES: Cc1cc(S(=O)(=O)N2CCN(C)CC2)[nH]c1C(=O)NC12C(=O)c3c(N)cccc3C1(O)Oc1cc([C@H]3C[C@H]3C)ccc12]

This compound was prepared similar to Example 18 above. LCMS: 592.3 [M+H]$^+$.

Example 25: N-(1-amino-4b-hydroxy-7-isopropyl-10-oxo-4b,10-dihydro-9bH-indeno[1,2-b]benzofuran-9b-yl)-3,5-dimethyl-4-sulfamoyl-1H-pyrrole-2-carboxamide (111)

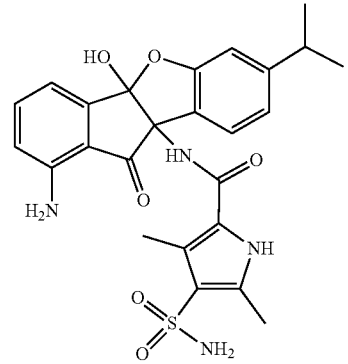 [SMILES: Cc1[nH]c(C(=O)NC23C(=O)c4c(N)cccc4C2(O)Oc2cc(C(C)C)ccc23)c(C)c1S(N)(=O)=O]

Scheme-20

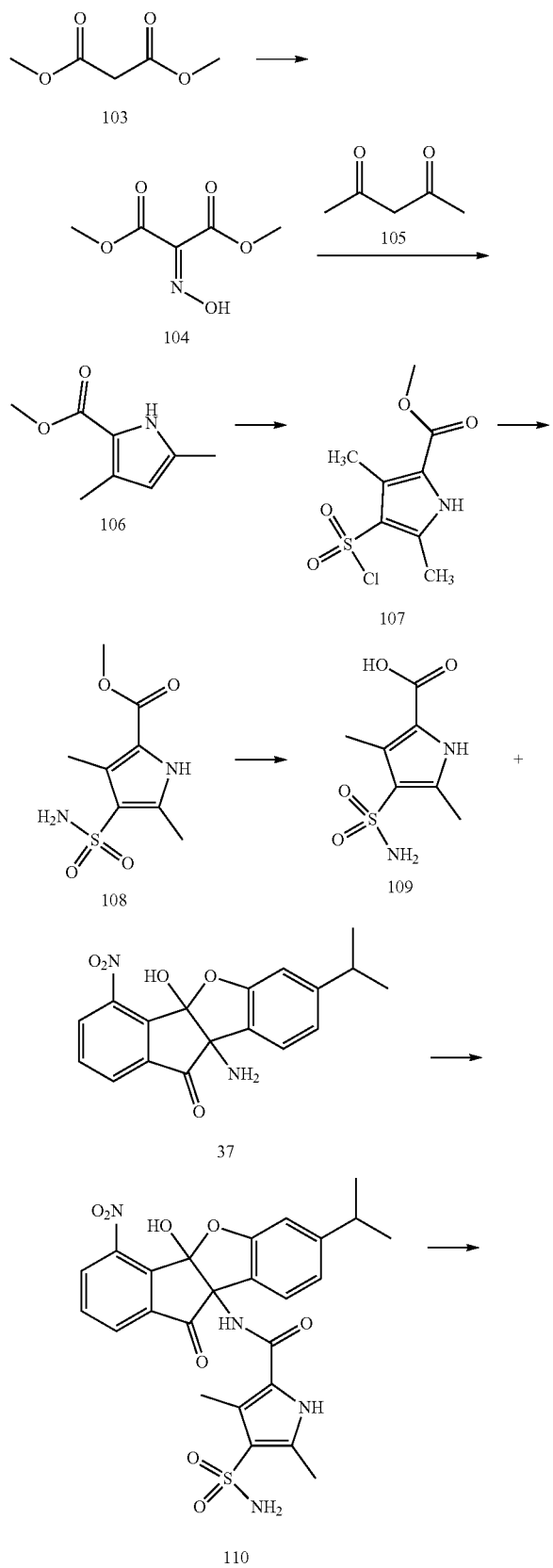

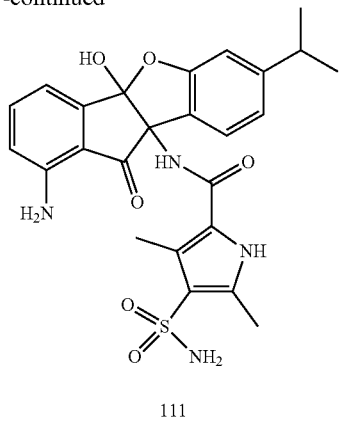

Dimethyl 2-(hydroxyimino)malonate (104)

To glacial acetic acid (55 mL) was added Dimethyl malonate 103 (21.7 mL, 190 mmol) under stirring, then a solution of sodium nitrite (26.2 g, 380 mmol) in 70 ml of water was added dropwise (for ~2 h). The obtained mixture was stirred at room temperature for 16 h. Reaction mass was extracted with ethyl acetate. Combined extracts were washed with water and with 5% sodium hydrogen carbonate solution until the aqueous solution became weakly alkaline. Organic layer was dried over $Na_2SO_4$, the solvent was evaporated to get solid product. Crude was used in the next step without further purification.

Methyl 3,5-dimethyl-1H-pyrrole-2-carboxylate (106)

To a solution of acetylacetone 105 (10.3 mL, 100 mmol) in acetic acid (40 mL) was gradually added a solution of dimethyl 2-(hydroxyimino)malonate 104 (17 g, 105 mmol) in 20 mL of acetic acid and 10 mL of water simultaneously with zinc dust (26 g, 400 mmol) at 95° C. The reaction mixture was stirred at same temperature for 2 h. Hot reaction mass was poured into 1000 mL of water. The solid precipitate was filtered off, washed with water, dried in air at room temperature, dissolved in DCM, filtered off from zinc dust residue, concentrated, and dried in air at room temperature. The product was dissolved in DCM and filtered through silica pad and washed with DCM. The solvent was evaporated solvent to get product.

Methyl 4-(chlorosulfonyl)-3,5-dimethyl-1H-pyrrole-2-carboxylate (107)

Methyl 3,5-dimethyl-1H-pyrrole-2-carboxylate 106 (383 mg, 2.5 mmol) was dissolved in Chloroform (0.25 M) and clear solution was cooled to 0° C. To the cold solution was added Chlorosulfonic acid (2.5 mL, 37.5 mmol) slowly. Reaction was stirred at 0° C. for 2.5 h. Reaction mass was slowly poured to ice cold water. The product was extracted with DCM (50 mL×2). The combined organic layer was washed with water (50 mL) and brine solution (50 mL), dried over anhy $Na_2SO_4$, and the solvent was evaporated to get crude. Crude was dissolved in DCM and filtered through silica-gel plug and washed with DCM to get product.

Methyl 3,5-dimethyl-4-sulfamoyl-1H-pyrrole-2-carboxylate (108)

Methyl 4-(chlorosulfonyl)-3,5-dimethyl-1H-pyrrole-2-carboxylate 107 (377.5 mg, 1.5 mmol) was taken in THF (15 mL) and was cooled to −10° C. To this was added solution of NH₃ in THF (5 mL) (prepared by purging Ammonia gas to THF at −20° C.). The reaction mass was warmed slowly to rt and was stirred for 2 h. THF was removed under vacuo to get residue. The residue was dissolved in ethyl acetate (100 mL) and was washed with water (50 mL×3) and dried over Na₂SO₄. The solvent was evaporated to get crude. The residue was purified by triturating with DCM and filtered to get the product.

3,5-Dimethyl-4-sulfamoyl-1H-pyrrole-2-carboxylic acid (109)

To the solution of methyl 3,5-dimethyl-4-sulfamoyl-1H-pyrrole-2-carboxylate 108 (255 mg, 1.1 mmol) in MeOH: H₂O (1:10) (11 mL) was added LiOH·H₂O (461.6 mg, 11 mmol). The reaction mass was stirred at rt for 12 h. MeOH was removed under vacuo and aq. layer was diluted with water (10 mL) and acidified to pH ~1 using 1 N HCl. The aqueous layer was extracted with ethyl acetate (50 mL×3). The combined organic layer was washed with water and with brine solution, dried over Na₂SO₄, and the solvent was evaporated to get the solid product which was used as such for next step without purification.

N-(4b-hydroxy-7-isopropyl-4-nitro-10-oxo-4b,10-dihydro-9bH-indeno[1,2-b]benzofuran-9b-yl)-3,5-dimethyl-4-sulfamoyl-1H-pyrrole-2-carboxamide (110)

3,5-Dimethyl-4-sulfamoyl-1H-pyrrole-2-carboxylic acid 109 (200 mg 0.91 mmol) was dissolved in DMF (9 mL) and the resulting solution was cooled to 0° C. EDCI (216.7 mg, 1.365 mmol), HOBT (184.5 mg, 1.365 mmol), and DIPEA (0.396 mL, 2.275 mmol) were added at 0° C. and the reaction mass was stirred for 30 min. 9b-amino-4b-hydroxy-7-isopropyl-4-nitro-4b,9b-dihydro-10H-indeno[1,2-b]benzofuran-10-one 37 (312 mg, 0.91 mmol) was then added and the reaction mixture was stirred at 30° C. for 15 h. The reaction was quenched with water (100 mL) and extracted with ethyl acetate (3×50 mL). The combined organic layer washed with brine solution and was dried over Na₂SO₄ and evaporated under vacuo The crude was purified by column chromatography (methanol: DCM) to get (110).

N-(1-amino-4b-hydroxy-7-isopropyl-10-oxo-4b,10-dihydro-9bH-indeno[1,2-b]benzofuran-9b-yl)-3,5-dimethyl-4-sulfamoyl-1H-pyrrole-2-carboxamide (111)

To a solution of N-(4b-hydroxy-7-isopropyl-4-nitro-10-oxo-4b,10-dihydro-9bH-indeno[1,2-b]benzofuran-9b-yl)-3,5-dimethyl-4-sulfamoyl-1H-pyrrole-2-carboxamide 110 (110 mg, 0.2 mmol) in EtOH-water mixture (1:1, 7 mL) was added Fe powder (33.5 mg, 0.6 mmol) and Conc HC (1 drop). The resulting solution was refluxed at 90° C. for 3 h. The hot reaction mass was filtered through CELITE pad and was washed with ethyl acetate. Organic layer was evaporated under vacuum. The residue obtained was dissolved in ethyl acetate (100 mL) and was washed with water (50 mL×2) then with brine solution. The combined organic layer was dried over Na₂SO₄ and the solvent was evaporated under vacuum to get crude. Crude was purified by silica gel column chromatography (methanol: DCM) to get product. (300 MHz, CD₃OD) δ 1.2 (dd, J=6.2 Hz, J=0.9 Hz, 6H), 2.44 (s, 3H), 2.49 (s, 3H), 2.84-2.87 (m, 1H), 6.70 (m, 2H), 6.89 (m 1H), 7.04 (m 1H), 7.48 (m, 2H). LCMS: 510.78 [M+1]⁺. LCMS: 511.5 [M+H]⁺.

Example 26: N-(1-amino-4b-hydroxy-7-((1R,2S)-2-methylcyclopropyl)-10-oxo-4b,10-dihydro-9bH-indeno[1,2-b]benzofuran-9b-yl)-3-methyl-5-(methylsulfonyl)-1H-pyrrole-2-carboxamide

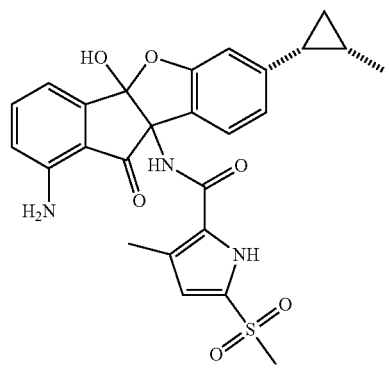 [SMILES: Cc1cc(S(C)(=O)=O)[nH]c1C(=O)NC12C(=O)c3c(N)cccc3C1(O)Oc1cc([C@@H]3C[C@@H]3C)ccc12]

This compound was prepared similar to Example 26 above. LCMS: 508.0 [M+H]⁺.

Example 27: N-(1-amino-4b-hydroxy-7-((1S,2R)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide

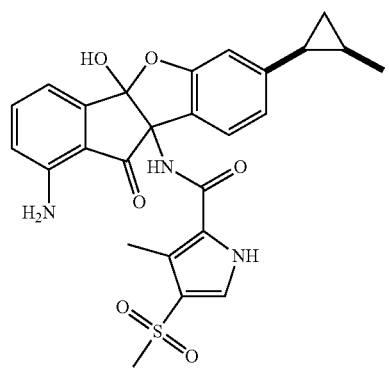 [SMILES: Cc1c(S(C)(=O)=O)c[nH]c1C(=O)NC12C(=O)c3c(N)cccc3C1(O)Oc1cc([C@H]3C[C@H]3C)ccc12]

This compound was prepared similar to Example 26 above. LCMS: 508.2 [M+H]⁺.

Example 28: N-((4bR,9bR)-1-amino-4b-hydroxy-7-((1S,2S)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide
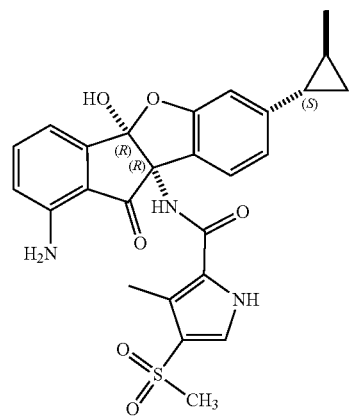
Scheme 22
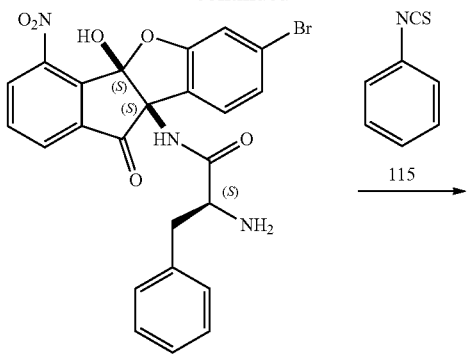
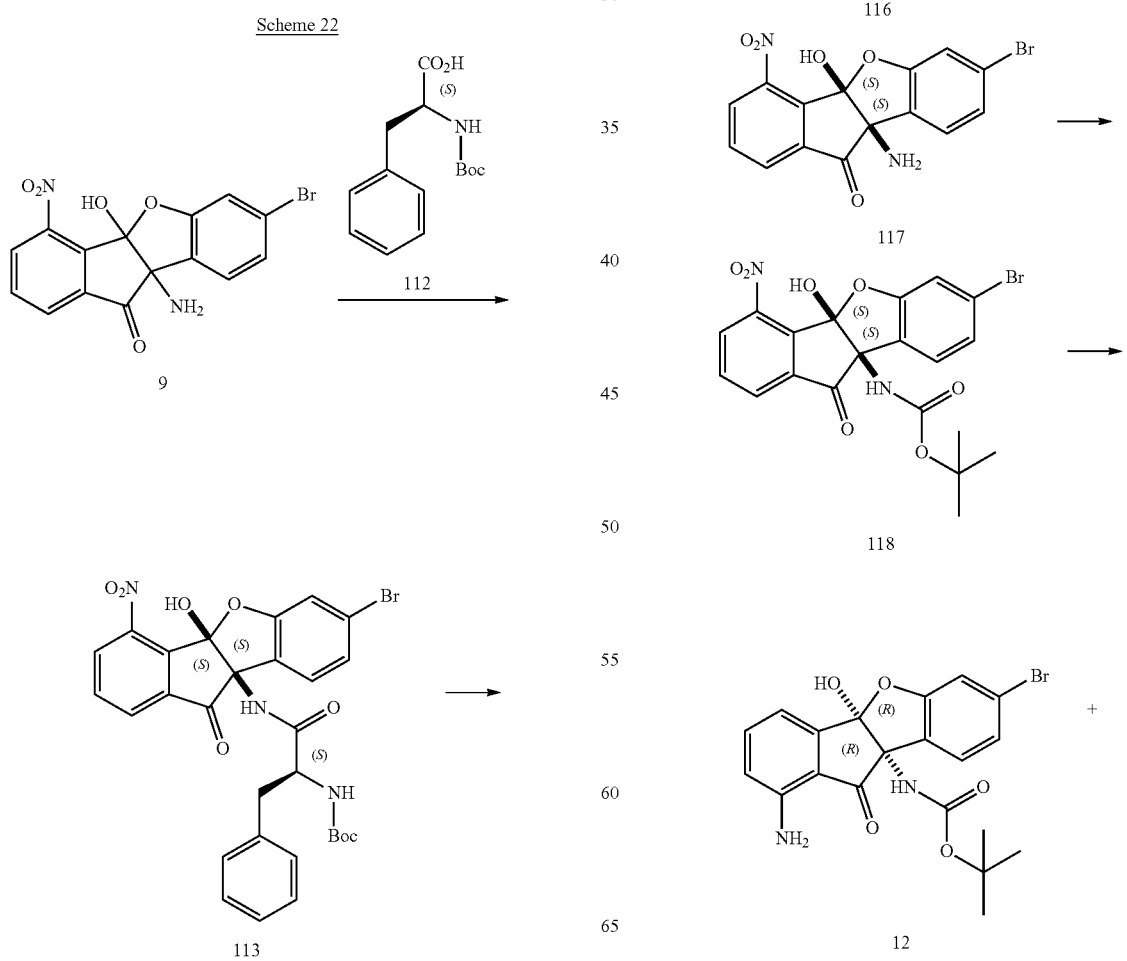

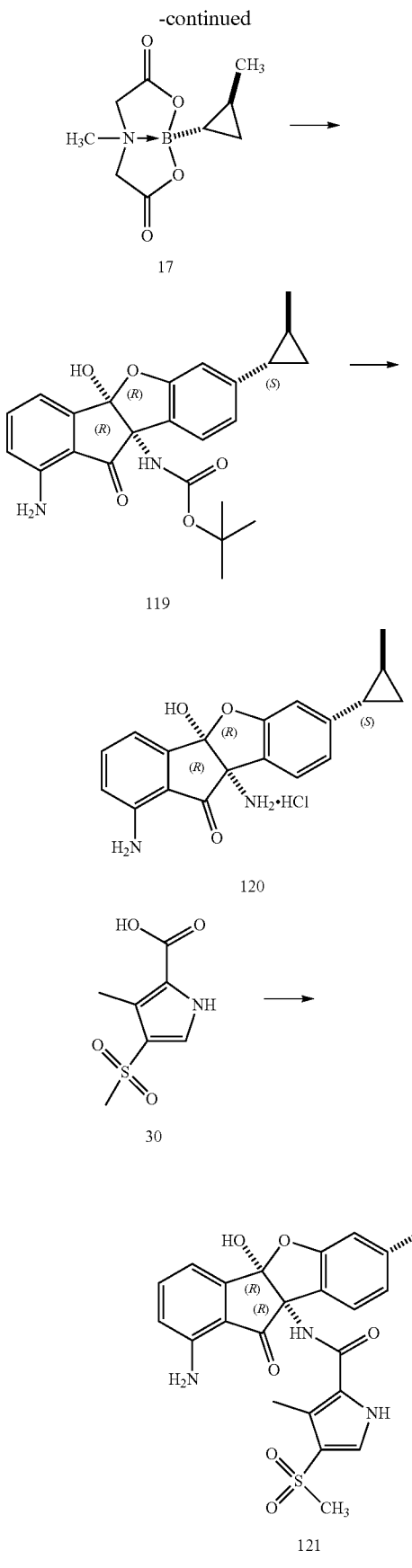

Tert-butyl ((S)-1-(((4bS,9bS)-7-bromo-4b-hydroxy-4-nitro-10-oxo-4b,10-dihydro-9bH-indeno[1,2-b]benzofuran-9b-yl)amino)-1-oxo-3-phenylpropan-2-yl)carbamate (113)

(Tert-butoxycarbonyl)-L-phenylalanine 112 (4.80 g, 16.4 mmol) was taken in DMF (110 mL, 0.15 M) and cooled to 0° C. Then this was charged with EDCI (4.73 g, 24.7 mmol) followed by HOBt (3.33 g, 24.7 mmol). This was stirred for next 20 mins and charged with 9b-amino-7-bromo-4b-hydroxy-4-nitro-4b,9b-dihydro-10H-indeno[1,2-b]benzofuran-10-one 9 (6.20 g, 16.4 mmol) followed by addition of DIPEA (8.6 mL, 49.3 mmol). This was stirred at 30° C. for next 24 hours. The reaction mixture was quenched with water and extracted with ethyl acetate. The organic layer was washed with water and with brine. The organic layer was dried over Na$_2$SO$_4$ and the solvent was evaporated to get crude. The crude was purified with silica-gel column chromatography to give product along with other isomer.

(S)-2-Amino-N-((4bS,9bS)-7-bromo-4b-hydroxy-4-nitro-10-oxo-4b,10-dihydro-9bH-indeno[1,2-b]benzofuran-9b-yl)-3-phenylpropanamide (114)

Tert-butyl ((S)-1-(((4bS,9bS)-7-bromo-4b-hydroxy-4-nitro-10-oxo-4b,10-dihydro-9bH-indeno[1,2-b]benzofuran-9b-yl)amino)-1-oxo-3-phenylpropan-2-yl)carbamate 113 (1.475 g, 2.36 mmol) was dissolved in DCM (47 mL). To the resulting solution was added HCl in Dioxane (5.9 mL 23.6 mmol) and reaction mass was stirred at r.t for 18 h. The reaction mass was evaporated to dryness, the residue was dissolved in water, and aqueous layer was basified with aq. NaHCO$_3$. The aqueous layer was extracted with ethyl acetate (150 mL×2) and the combined organic layer was washed with water (100 mL) then with brine solution. The combined organic layer was dried over Na$_2$SO$_4$ and the solvent was evaporated under vacuum to get crude product, which was used as such for next step without purification.

(S)—N-((4bS,9bS)-7-bromo-4b-hydroxy-4-nitro-10-oxo-4b,10-dihydro-9bH-indeno[1,2-b]benzofuran-9b-yl)-3-phenyl-2-(3-phenylthioureido)propanamide (116)

Isothiocyanatobenzene 115 (0.425 mL, 3.54 mmol) was added to solution of (S)-2-amino-N-((4bS,9bS)-7-bromo-4b-hydroxy-4-nitro-10-oxo-4b,10-dihydro-9bH-indeno[1,2-b]benzofuran-9b-yl)-3-phenylpropanamide 114 (1.25 g, 2.36 mmol) in DCM (24 mL) at 0° C. The reaction mass then warmed to rt and the resulting mixture was stirred for 24 h at 28° C. Reaction mass was evaporated to dryness to get crude. Crude was purified over short silica-gel column chromatography (ethyl acetate: hexane) to get the product.

(4bS,9bS)-9b-Amino-7-bromo-4b-hydroxy-4-nitro-4b,9b-dihydro-10H-indeno[1,2-b]benzofuran-10-one (117)

(S)—N-((4bS,9bS)-7-bromo-4b-hydroxy-4-nitro-10-oxo-4b,10-dihydro-9bH-indeno[1,2-b]benzofuran-9b-yl)-3-phenyl-2-(3-phenylthioureido)propanamide 116 (1.70 g, 2.58 mmol) was dissolved in DCM (260 mL). To this solution TFA (8.8 mL, 77.4 mmol) at rt. was added The reaction mass then warmed to 50° C. for 12 h. DCM was evaporated and the residue obtained was dissolved in water. The aqueous layer was basified by saturated solution of NaHCO$_3$ then the aqueous layer was extracted with ethyl acetate. Combined organic layer was dried over Na₂SO₄ and the solvent was evaporated to get crude. Crude was purified over silica-gel column chromatography (Ethyl acetate:Hexane) to get product.

Tert-butyl ((4bS,9bS)-7-bromo-4b-hydroxy-4-nitro-10-oxo-4b,10-dihydro-9bH-indeno[1,2-b]benzofuran-9b-yl)carbamate (118)

(4bS,9bS)-9b-Amino-7-bromo-4b-hydroxy-4-nitro-4b,9b-dihydro-10H-indeno[1,2-b]benzofuran-10-one 117 (472 mg, 1.25 mmol) was dissolved in THF (1.25 mL). To this Boc anhydride (546 mg, 2.5 mmol) was added followed by addition of iodine (32 mg, 0.125 mmol). The reaction mass was stirred at rt for 36 h. The reaction mass was evaporated to dryness. The residue was purified over silica gel column chromatography (ethyl acetate:Hexane) to get product.

Tert-butyl ((4bR,9bR)-1-amino-7-bromo-4b-hydroxy-10-oxo-4b,10-dihydro-9bH-indeno[1,2-b]benzofuran-9b-yl)carbamate (12)

Tert-butyl ((4bS,9bS)-7-bromo-4b-hydroxy-4-nitro-10-oxo-4b,10-dihydro-9bH-indeno[1,2-b]benzofuran-9b-yl)carbamate 118 (460 mg, 0.96 mmol) was dissolved in EtOH-water mixture (1:1, 10 mL). Fe powder (161 mg, 2.88 mmol) and Conc HCl (2 drops) were added. The clear solution was refluxed at 90° C. for 3 h. The hot reaction mass was filtered through CELITE pad and was washed with ethyl acetate. Organic layer was evaporated under vacuum. The residue obtained was dissolved in ethyl acetate (250 mL) and was washed with water (100 mL×2) and then with brine solution. The combined organic layer was dried over Na₂SO₄ and the solvent was evaporated under vaccuo to get crude. The crude was purified over silica gel column chromatography (ethyl acetate:Hexane) to get product.

Tert-butyl ((4bR,9bR)-1-amino-4b-hydroxy-7-((1S,2S)-2-methylcyclopropyl)-10-oxo-4b,10-dihydro-9bH-indeno[1,2-b]benzofuran-9b-yl)carbamate (119)

To a degassed solution of tert-butyl ((4bR,9bR)-1-amino-7-bromo-4b-hydroxy-10-oxo-4b,10-dihydro-9bH-indeno[1,2-b]benzofuran-9b-yl)carbamate 12 (326 mg, 0.73 mmol) in Toluene (12.5 mL), water (2.5 mL), Pd(OAc)₂ (16.4 mg 0.073 mmol), RuPhos (68 mg, 0.146 mmol), and K3PO₄ (620 mg, 2.92 mmol) were added. Then 6-methyl-2-((1S,2S)-2-methylcyclopropyl)-1,3,6,2-dioxazaborocane-4,8-dione 17 (231 mg, 1.095 mmol) was added. The resulting reaction mass was purged with N2 for 10 min then reaction mass was stirred at 100° C. for 1 h. The reaction mass was cooled to rt, and was diluted with ethyl acetate (100 mL). Organic layer was washed with water (50 mL×2), dried over Na₂SO₄, and the solvent was and evaporated to get crude. Crude was purified over silica-gel column chromatography (Ethyl acetate:Hexane) to get product.

(4bR,9bR)-1,9b-Diamino-4b-hydroxy-7-((1S,2S)-2-methylcyclopropyl)-4b,9b-dihydro-10H-indeno[1,2-b]benzofuran-10-one hydrochloride (120)

Tert-butyl ((4bR,9bR)-1-amino-4b-hydroxy-7-((1S,2S)-2-methylcyclopropyl)-10-oxo-4b,10-dihydro-9bH-indeno[1,2-b]benzofuran-9b-yl)carbamate 119 (250 mg 0.59 mmol) was dissolved in DCM (12 mL). To this solution HCl in dioxane (1.5 mL, 5.9 mmol) was added and reaction mass was stirred for 12 h. The reaction mass was evaporated to dryness to get product (crude), which was used as such for next step.

N-((4bR,9bR)-1-Amino-4b-hydroxy-7-((1S,2S)-2-methylcyclopropyl)-10-oxo-4b,10-dihydro-9bH-indeno[1,2-b]benzofuran-9b-yl)-3-methyl-4-(methylsulfonyl)-1H-pyrrole-2-carboxamide(121)

3-Methyl-4-(methylsulfonyl)-1H-pyrrole-2-carboxylic acid 30 (97.6 mg 0.48 mmol) was dissolved in DMF (8 mL). The resulting solution was cooled to 0° C. HATU (28.2 mg, 0.60 mmol) and DIPEA (0.210 mL, 1.2 mmol) were added at 0° C. and the reaction mass was stirred for 30 min. Then (4bR,9bR)-1,9b-diamino-4b-hydroxy-7-((1S,2S)-2-methylcyclopropyl)-4b,9b-dihydro-10H-indeno[1,2-b]benzofuran-10-one hydrochloride 120 (144 mg, 0.4 mmol) was added and reaction was stirred 30° C. for 15 h. The reaction was quenched with water (100 mL) and aqueous layer was extracted with ethyl acetate (2×100 mL). The combined organic layer washed with water and with brine solution, dried over Na₂SO₄, and the solvent was evaporated under vacuum. The crude was purified over silica gel column chromatography (MeOH:DCM) and then purified by preparative HPLC (ethanol:hexane) to get the product. (300 MHz, MeOD) δ 0.66-0.72 (m, 1H), 0.78-0.84 (m, 1H), 0.95-1.03 (m, 1H), 1.13 (d, J=6.0 Hz, 3H), 1.49-1.55 (m, 1H), 2.48 (s, 3H), 3.05 (s, 3H), 6.45 (s, 1H), 6.63-6.67 (m, 1H), 6.76 (d, J=8.1 Hz, 1H), 7.02 (d, J=7.2 Hz, 1H), 2.27 (d, J=8.1 Hz, 1H), 7.38 (s, 1H), 7.43-7.49 (m, 1H). LCMS: 508.1 [M+H]⁺.

Bioactivity of the Compounds of the Invention was Determined Using the Following Methods. Determination of Drug Efficacy Against Picornaviruses Using Cytopathic Effect (CPE) Inhibition Assay In the assay, HeLa (human cervical cancer cells), MRC-5 (human fetal lung fibroblast cells), and RD cells (derived from human rhabdomyosarcoma) were employed. For comparison, ribavirin (Riv), Pleconaril (pleco), and BTA-798 (BTA) were used as controls. Reagents were dissolved at a concentration of 10-40 mg/ml in 100% dimethyl sulfoxide (DMSO). Water-soluble reagents were dissolved in PBS (−) solution and stored at −20° C. On the day of the experiment, they were used in 3 fold to 5 fold concentrations in such a manner that the concentration of dimethyl sulfoxide in each well was between 0.5% and 1%.

Pharmaceutical efficacy was determined using a virus-induced cytopathic effect (CPE) inhibition assay. In this regard, after cells suitable for viruses were grown in 96-well plates, dilutions of viruses in DME supplemented with 2% FBS (DME/2% FBS) or MEM supplemented with 2% FBS (MEM/2% FBS) were inoculated in an amount of 100l with a concentration corresponding to 100 CCID50 (50% cell culture infective dose) into each well of the plates, and incubated for 30 min-1 hr at 33° C. or 37° C. to allow the viruses to adsorb onto the cells. The culture medium was removed before aliquots of drug dilutions with various concentrations were added in an amount of 100 µl to each well. While HRV (human rhinovirus) was grown at 33° C., the other viruses were incubated in a 37° C. CO₂ incubator for 2-3 days. Alternatively, the cells were cultured for 2-3 days without removal of the medium after they were added with 50 µl of each drug dilution having a 2-fold higher concentration and then with 50 µl of the virus dilution. Viruses were incubated in host HeLa cells at 37° C. for 2-3 days in DME/2% or MEM/2% FBS.

For HeLa cells, the drugs were measured for $EC_{50}$ (50% maximal effective concentration), which is the concentration of a drug inducing a response halfway between the baseline and maximum, using an MTT assay. With regard to RD and MRC-5 cells, CPE was determined using FDA (Fluorescein diacetate) or MTT. In order to determine the effect of drug toxicity on efficacy results, at the time of inoculation with the virus, mock-infection was also included. A virus-free medium was added to a cell culture, which was then subjected to the same treatment as the mock-infected cells inoculated with the virus. That is, the medium was removed after one hour of incubation, and dilutions of drugs in the medium were added once more. Following incubation for 2-3 days, the cells were observed under a microscope and the drugs were determined for $CC_{50}$ (50% cytotoxic concentration) at which 50% of the cells were killed, using an MTT assay in which counts of viable cells in mock-infected wells containing drugs were compared to those of viable cells in control wells containing no drugs. In an FDA hydrolysis assay, FDA was added to each well after removal of the medium, and incubated for 20-30 min before fluorescence intensity was measured using a spectrofluorometer to determine CPE in the same manner as in MTT.

That is, the survival rate (% survival) of mock-infected cells for cytotoxicity measurement was calculated using the Mathematical Formula 1 below:

Cell Drug=Survival by [$A$(Drug)–$A$(Background solution)/$A$(Cell control)–$A$(Background×100% Solution)]

While 100% cell survival means no cytotoxicity of the drug, the highest cytotoxicity is reflected by 0% cell survival. The 50% cytotoxic concentration was defined as the concentration required to reduce the cell number by 50%. This concentration of the drug is represented as CC50. Higher values mean lower cytotoxicity.

In addition, antiviral effects can be calculated using Mathematical Formula 2 below:

Antiviral Effect=[$A$(Drug/Virus)–$A$(Virus Control)/$A$(Cell control)–$A$(Virus Control)]

If the survival rate is 100%, its antiviral effect is 100% whereas if the survival rate is 0%, its antiviral effect is none. While the concentration of a drug at which the cell in a well infected with a virus can exhibit 50% survival rate is calculated as $EC_{50}$, the lower this value is, the more superior the antiviral effect is.

In Table 1 below are listed $LC_{50}$ concentrations that exhibit cytotoxicity against the compounds in some examples and $EC_{50}$ concentrations that exhibit activities against a number of rhinoviruses belonging to the picornaviruses.

Determination of Drug Effect Against Picornaviruses Using Multicycle Cytopathic Effect (CPE) Reduction Assay The multicycle CPE reduction assay was used to conduct determination of drug efficacy against picornaviruses. The antiviral activity of a compound was initially determined by the CPE reduction assay based on MIS [3-(4,5-dimethyl thiazol-2-yl)-5-(3-carboxy methoxy phenyl)-2-(4-sulfophenyl)-2H-tetrazolium.

Specifically, cells grown to confluence in 96-well plates were infected with 100 50% cell culture infected doses ($CCID_{50}$) of virus. After an adsorption period of 2 hrs at 37° C., the virus was removed and serial dilutions of the compounds were added. The cultures were further incubated at 37° C., for 3 days until complete CPE was observed in the infected and untreated virus control (VC). After removal of the medium, 90 µl of a culture medium and 10 µl of MTS-phenazine methosulfate (Promega, Leiden, The Netherlands) were added to each well. After an incubation period of 2 hrs at 37° C., the optical density (OD) of each well was read at 498 nm in a microplate reader.

The % CPE values for evaluating antiviral activity were calculated using Mathematical Formula 3 below:

% CPE=100×[OD (CC)–OD (Virus+Compound)/OD (CC)–OD (VC)]

The % CPE value for measuring cytotoxicity of a drug was calculated by Mathematical Formula 4 below:

% CPE=100×[OD (CC)–OD (Virus+Compound)/OD (CC)–OD (Blank)]

In Mathematical Formulae 3 and 4 above,

OD (CC) represents the OD of the background cell culture that is neither induced by a virus nor treated by chemical, OD (VC) represents the OD of the control cell culture that is induced by a virus but not treated by chemical, OD (Virus+Compound) represents the OD of the cell culture infected by a virus that has been treated with a concentrated compound, OD (Compound) represents the OD of the cell culture that has been treated with a concentrated compound only, and OD (Blank) represents the OD of the well to which only the cell culture has been added.

The effective concentration ($EC_{50}$) represents the concentration of a drug at which 50% of cells are allowed to survive by CPE of an induced virus, and the cytotoxicity concentration ($CC_{50}$) represents the concentration of a drug at which a compound has killed 50% of cells, and they were calculated by the logarithmic interpolation.

In Table 1 below are listed the toxicity concentrations ($CC_{50}$) and effective concentrations ($EC_{50}$) against various viruses for some compounds of the examples.

TABLE 1

Table of Bioactivity Data

| Example No. | HRV A16 CPE ($EC_{50}$ µM) | HRV A29 CPE ($EC_{50}$ µM) | HRV A1B_CPE ($EC_{50}$ µM) | HRV B14 CPE ($EC_{50}$ µM) | C15_C3 REPLICON ($EC_{50}$ µM) | CYTOTOX ($CC_{50}$ µM) |
|---|---|---|---|---|---|---|
| 1 | 0.228 | 0.071 |  | 0.016 | 3.995 | 34.660 |
| 2 | 0.092 |  |  | 0.016 | 0.853 | 27.341 |
| 3 | 0.057 | 0.020 | 0.033 | 0.016 | 4.813 | 32.278 |
| 4 | 0.056 |  |  | 0.016 | 2.394 | 8.581 |
| 5 | 0.072 | 0.039 | 0.036 | 0.016 | 1.354 | 19.163 |
| 6 | 0.046 |  |  | 0.016 | 1.184 | 19.124 |
| 7 | 0.065 |  |  |  | 1.622 | 12.041 |

TABLE 1-continued

Table of Bioactivity Data

| Example No. | HRV A16 CPE (EC$_{50}$ µM) | HRV A29 CPE (EC$_{50}$ µM) | HRV A1B_CPE (EC$_{50}$ µM) | HRV B14 CPE (EC$_{50}$ µM) | C15_C3 REPLICON (EC$_{50}$ µM) | CYTOTOX (CC$_{50}$ µM) |
|---|---|---|---|---|---|---|
| 8  | 0.068 | 0.035 | 0.031 | 0.016 | 5.335 | 34.980 |
| 9  | 0.020 |       |       | 0.016 | 1.092 | 25.587 |
| 10 | 0.661 |       |       | 0.016 | 0.632 | 29.159 |
| 11 | 0.023 |       |       | 0.016 | 2.542 | 12.090 |
| 13 | 0.027 | 0.050 | 0.016 | 0.016 | 0.682 | 32.081 |
| 14 | 0.023 | 0.030 | 0.016 | 0.016 | 0.516 | 21.881 |
| 15 | 0.213 |       |       | 0.016 | 0.264 | 45.237 |
| 16 | 0.199 | 0.104 |       | 0.016 | 1.820 | 37.727 |
| 17 | 0.070 | 0.018 | 0.016 | 0.016 | 1.357 | 24.530 |
| 18 | 0.050 | 0.016 | 0.018 |       | 1.651 | 31.819 |
| 19 | 0.022 | 0.046 | 0.016 |       | 0.876 | 48.293 |
| 21 | 0.026 | 0.074 | 0.070 | 0.016 | 2.911 | 37.334 |
| 22 | 0.063 | 0.023 | 0.041 | 0.016 | 1.887 | 34.930 |
| 23 | 0.071 |       |       | 0.016 | 0.633 | 22.399 |
| 24 | 0.039 | 0.037 | 0.016 | 0.016 | 0.340 | 28.384 |
| 25 | 0.140 |       |       | 0.016 | 2.039 | 26.958 |
| 26 | 0.093 | 0.274 | 0.170 | 0.016 | 8.366 | 37.134 |
| 27 | 0.084 | 0.079 | 0.020 | 0.016 | 0.705 | 40.427 |
| 28 | 0.160 | 0.045 | 0.037 | 0.016 | 1.846 | 19.813 |

As is indicated in Table 1 above, most of the compounds according to the present invention exhibit high CC$_{50}$ concentrations so are found to have low cytotoxicity. In addition, the compounds according to the present invention were mostly found to have high antiviral activities against a number of rhinoviruses (HRV).

Therefore, since the compounds in the example according to the present invention exhibit low cytotoxicity and high antiviral activities against various rhinoviruses, they may be usefully used for a pharmacological composition for preventing or treating diseases caused by the picornaviruses to which they belong.

Therefore, since the compounds in the examples according to the present invention have low cytotoxicity and exhibit antiviral activities against picornaviruses to which coxsackieviruses, polioviruses and rhinoviruses belong, they can be used effectively for prevention or treatment of the diseases caused by such viruses, for example, respiratory, cardiocirculatory, and nervous system diseases, including poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis and otitis media.

As the compounds expressed in Formulae according to the present invention that are in equilibria with each other have not only low cytotoxicity but also high antiviral activities against picornaviruses including coxsackieviruses, enteroviruses, echoviruses, polioviruses and rhinoviruses, they can be used effectively as pharmaceutical compositions for prevention or treatment of viral disease such as poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

The invention claimed is:

1. A compound of Formula (Ib), or a pharmaceutically acceptable salt thereof:

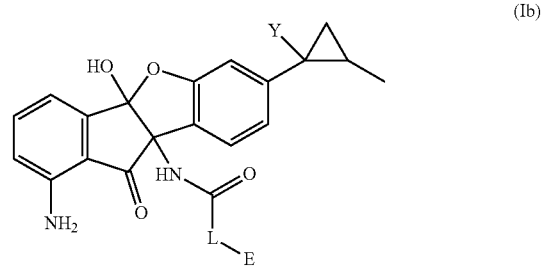

(Ib)

wherein Y is H or CH$_3$;
L is a bond or CH$_2$;
E is
a) —CH(CHOHCH$_3$)(NMe$_2$); or
b)

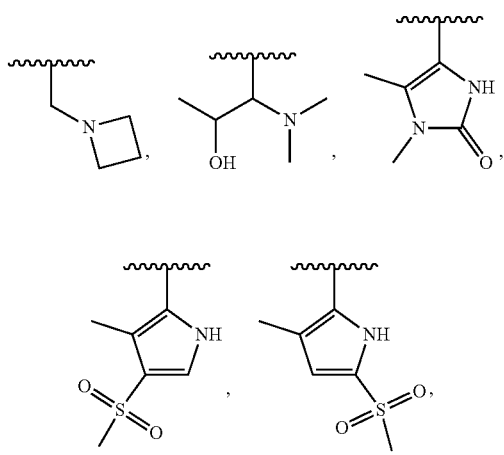

-continued

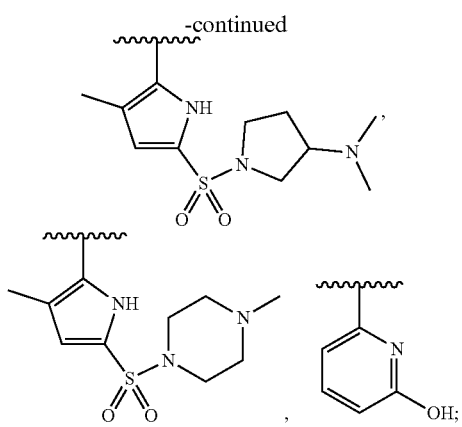

or a monocyclic 4-6 membered heterocyclyl containing one or two nitrogen atoms or a 5-6 membered heteroaryl containing one nitrogen atom.

2. A compound of Formula (Ic), or a pharmaceutically acceptable salt thereof:

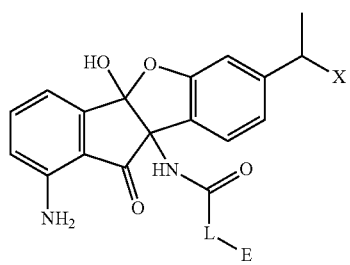

(Ic)

wherein X is cyclopropyl;
L is a bond or CH$_2$;
E is
   a) —CH(CHOHCH$_3$)(NMe$_2$); or
   b)

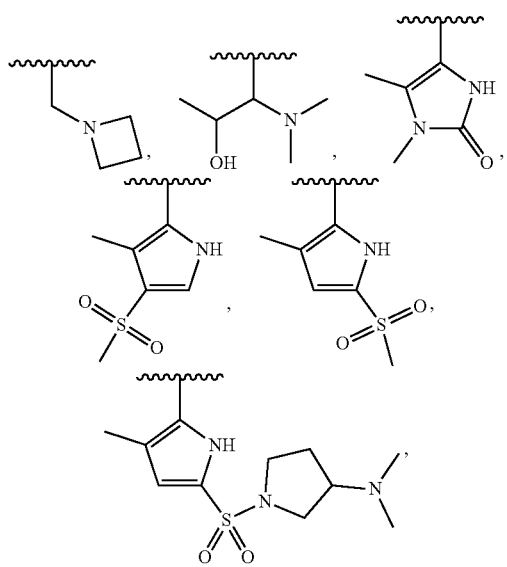

-continued

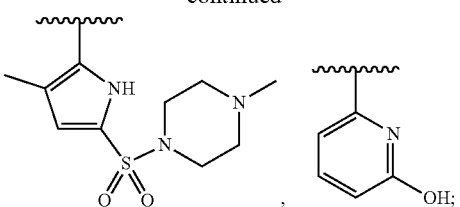

or a monocyclic 4-6 membered heterocyclyl containing one or two nitrogen atoms or a 5-6 membered heteroaryl containing one nitrogen atom.

3. A compound or a pharmaceutically acceptable salt thereof; selected from:

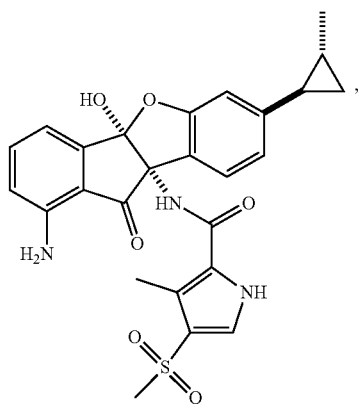

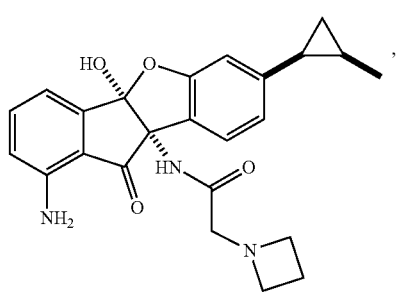

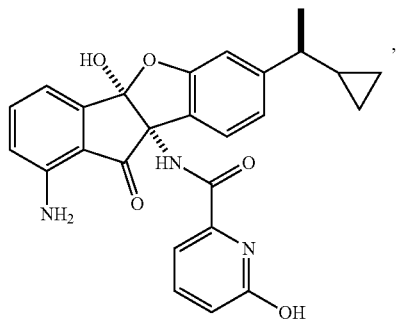

115
-continued
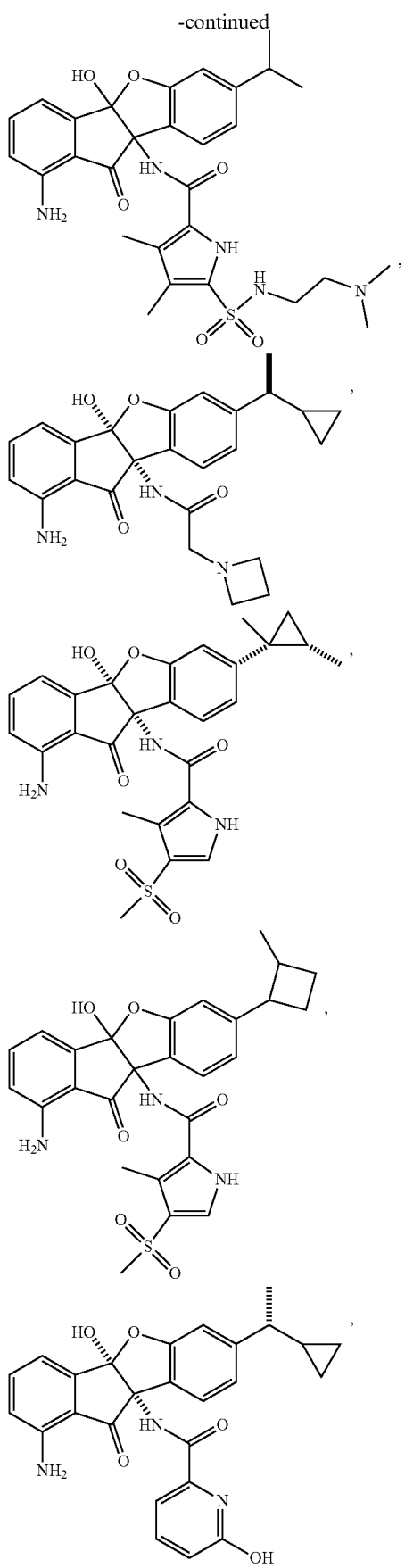
116
-continued
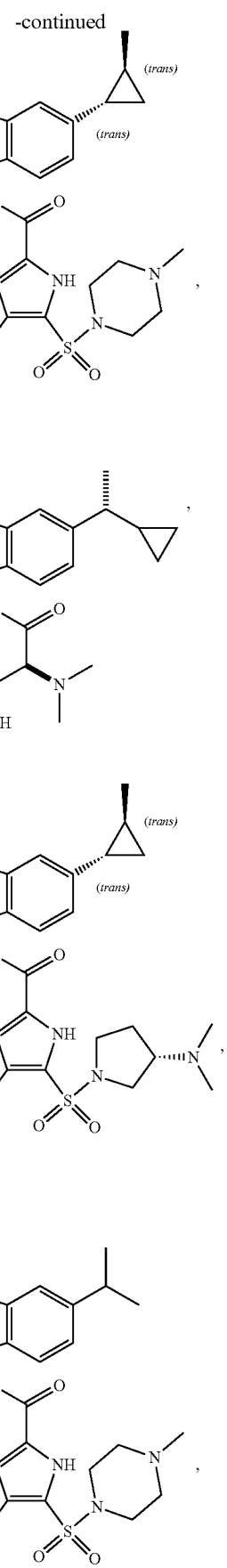

117
-continued
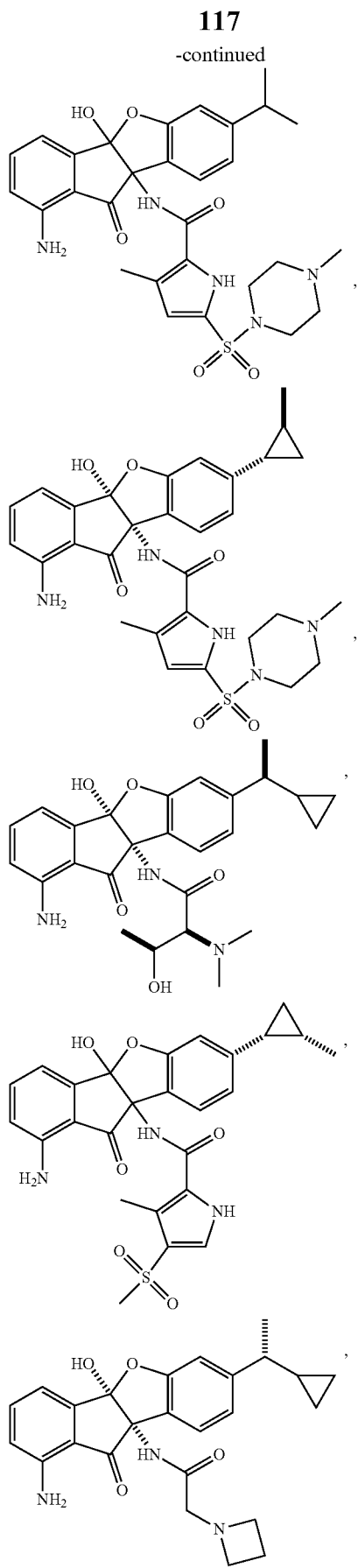
118
-continued
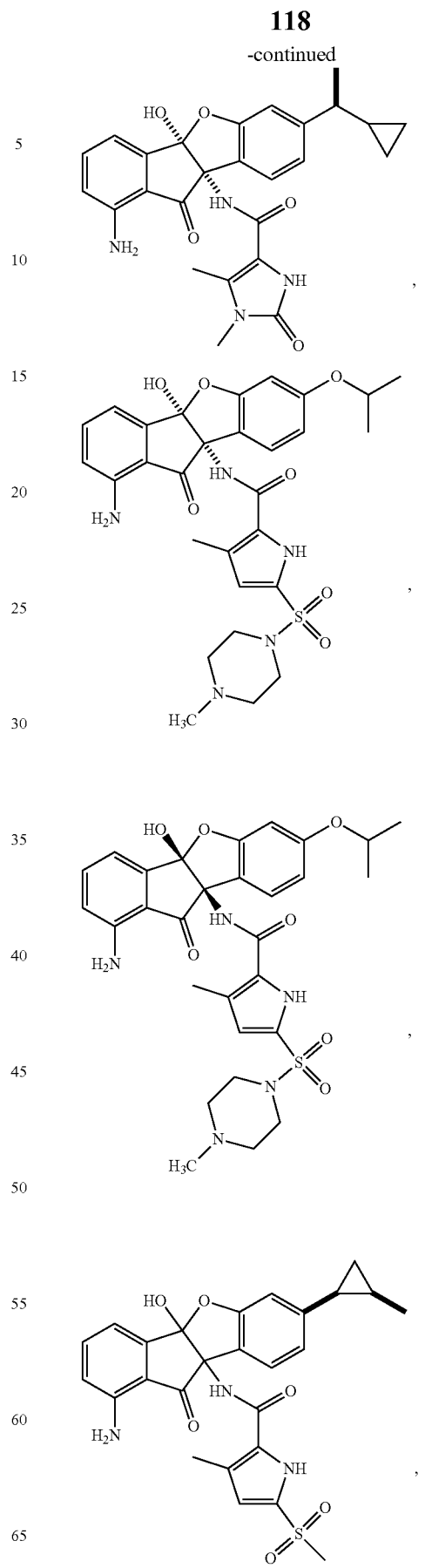

119
-continued
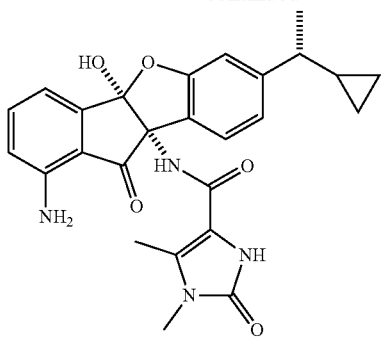
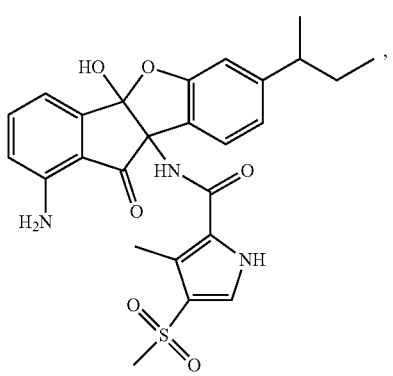
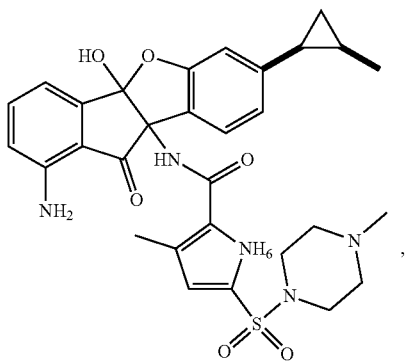
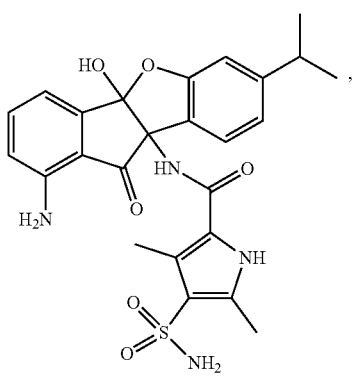
120
-continued
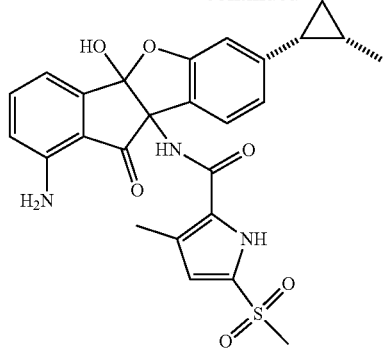
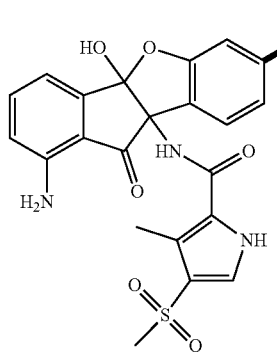, and
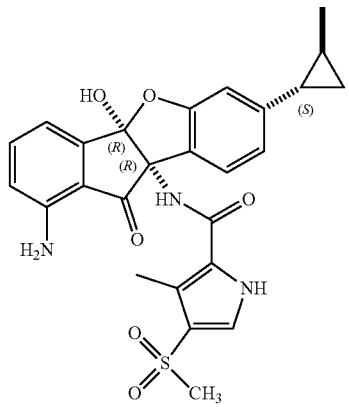
4. A compound, or a pharmaceutically acceptable salt thereof, selected from:
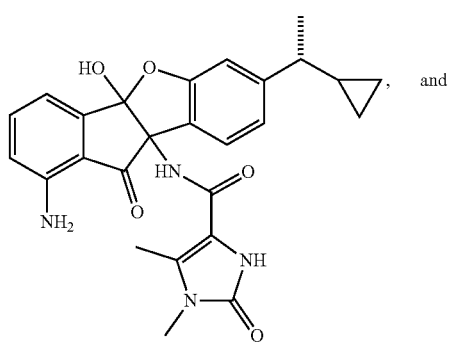, and -continued
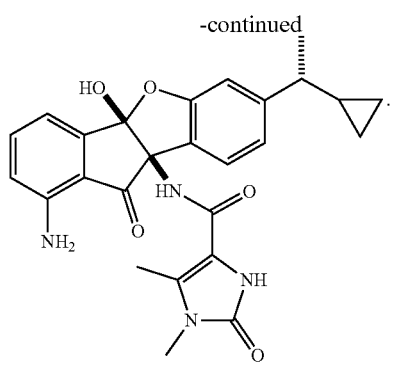
* * * * *